(12) United States Patent
Tseng et al.

(10) Patent No.: US 9,161,954 B2
(45) Date of Patent: *Oct. 20, 2015

(54) AMNIOTIC MEMBRANE PREPARATIONS AND PURIFIED COMPOSITIONS AND ANTI-ANGIOGENESIS TREATMENT

(71) Applicant: TissueTech, Inc., Miami, FL (US)

(72) Inventors: Scheffer Tseng, Pinecrest, FL (US); Hua He, Miami, FL (US); Wei Li, Shenzhen (CN)

(73) Assignee: TISSUETECH, INC., Doral, FL (US)

( * ) Notice: Subject to any disclaimer, the term of this patent is extended or adjusted under 35 U.S.C. 154(b) by 168 days.

This patent is subject to a terminal disclaimer.

(21) Appl. No.: 13/796,761

(22) Filed: Mar. 12, 2013

(65) Prior Publication Data
US 2013/0195992 A1 Aug. 1, 2013

Related U.S. Application Data

(63) Continuation of application No. 13/453,840, filed on Apr. 23, 2012, now Pat. No. 8,420,126, which is a continuation of application No. 11/535,924, filed on Sep. 27, 2006, now Pat. No. 8,187,639.

(60) Provisional application No. 60/720,760, filed on Sep. 27, 2005.

(51) Int. Cl.
| A61K 35/50 | (2015.01) |
| A61K 35/48 | (2015.01) |
| A61K 38/17 | (2006.01) |
| A61K 38/39 | (2006.01) |
| A61K 31/728 | (2006.01) |

(52) U.S. Cl.
CPC ............... *A61K 35/50* (2013.01); *A61K 31/728* (2013.01); *A61K 35/48* (2013.01); *A61K 38/17* (2013.01); *A61K 38/1709* (2013.01); *A61K 38/39* (2013.01)

(58) Field of Classification Search
CPC . A61K 35/50; A61K 38/1709; A61K 31/728; A61K 35/48; A61K 38/17; A61K 38/39
USPC ........................................................ 424/583
See application file for complete search history.

(56) References Cited

U.S. PATENT DOCUMENTS

| 3,598,122 A | 8/1971 | Zaffaroni |
| 3,598,123 A | 8/1971 | Zaffaroni |
| 3,710,795 A | 1/1973 | Higuchi et al. |
| 3,731,683 A | 5/1973 | Zaffaroni |
| 3,742,951 A | 7/1973 | Zaffaroni |
| 3,814,097 A | 6/1974 | Ganderton et al. |
| 3,921,636 A | 11/1975 | Zaffaroni |
| 3,972,995 A | 8/1976 | Tsuk et al. |
| 3,993,072 A | 11/1976 | Zaffaroni |
| 3,993,073 A | 11/1976 | Zaffaroni |
| 3,996,934 A | 12/1976 | Zaffaroni |
| 4,031,894 A | 6/1977 | Urquhart et al. |
| 4,060,084 A | 11/1977 | Chandrasekaran et al. |
| 4,069,307 A | 1/1978 | Higuchi et al. |
| 4,077,407 A | 3/1978 | Theeuwes et al. |
| 4,100,022 A | 7/1978 | Ogasa et al. |
| 4,120,649 A | 10/1978 | Schechter |
| 4,201,211 A | 5/1980 | Chandrasekaran et al. |
| 4,230,105 A | 10/1980 | Harwood |
| 4,292,299 A | 9/1981 | Suzuki et al. |
| 4,292,303 A | 9/1981 | Keith et al. |
| 4,305,502 A | 12/1981 | Gregory |
| 4,327,725 A | 5/1982 | Cortese et al. |
| 4,361,552 A | 11/1982 | Baur, Jr. |
| 4,476,116 A | 10/1984 | Anik |
| 4,599,084 A | 7/1986 | Nashef |
| 4,599,226 A | 7/1986 | Fox, Jr. et al. |
| 4,624,848 A | 11/1986 | Lee |
| 4,829,000 A | 5/1989 | Kleinman et al. |
| 4,871,549 A | 10/1989 | Ueda et al. |
| 4,968,509 A | 11/1990 | Radebaugh et al. |
| 4,997,425 A | 3/1991 | Shioya et al. |

(Continued)

FOREIGN PATENT DOCUMENTS

| EP | 0669138 | 8/1995 |
| EP | 1604695 | 12/2005 |

(Continued)

OTHER PUBLICATIONS

Bae et al., "Characterization of the Promoter Region of the Human Transforming Growth Factor-β Type II Receptor Gene," J. Biol. Chem. 270(49):29460-29468 (1995).

Bhutto et al., "Localization of Collagen XVIII and the Endostatin Portion of Collagen XVIII in Ages Human Control Eyes and Eyes with Age-Related Macular Degeneration," Invest. Ophthalmol. Vis. Sci. 45(5):1544-1552 (2004).

Border, W.A. and Ruoslahti, E., "Transforming Growth Factor-β in Disease: The Dark Side of Tissue Repair," J. Clin. Invest. 90:1-7 (1992).

Chen et al., "Recombinant Adenovirus Coexpressing Covalent Peptide/MHC Class II Complex and B7-1: In Vitro and In Vivo Activation of Myelin Basic Protein-Specific T Cells," J. Immunol. 167:1297-1305 (2001).

Chen et al., "Functions of hyaluronan in wound repair," Wound Rep. Reg. 7:79-89 (1999).

Day et al., "Hyaluronan cross-linking: a protective mechanism in inflammation?" Trends in Immunology 26(12):637-643 (2005).

(Continued)

*Primary Examiner* — Taeyoon Kim
(74) *Attorney, Agent, or Firm* — Wilson Sonsini Goodrich & Rosati

(57) ABSTRACT

Compositions having a combination of specific biological components have been found to exert a number of useful effects in mammalian cells, including modulating TGF β signaling, apoptosis, and proliferation of mammalian cells, as well as decreasing inflammation in mice. These components can be obtained commercially, or can be prepared from biological tissues such as placental tissues. Placental amniotic membrane (AM) preparations described herein include AM pieces, AM extracts, AM jelly, AM stroma, and mixtures of these compositions with additional components. The compositions can be used to treat various diseases, such as wound healing, inflammation and angiogenesis-related diseases.

12 Claims, 25 Drawing Sheets

(56) References Cited

U.S. PATENT DOCUMENTS

| | | |
|---|---|---|
| 5,002,071 A | 3/1991 | Harrell |
| 5,011,692 A | 4/1991 | Fujioka et al. |
| 5,017,381 A | 5/1991 | Maruyama et al. |
| 5,033,252 A | 7/1991 | Carter |
| 5,052,558 A | 10/1991 | Carter |
| 5,093,487 A | 3/1992 | Brown et al. |
| 5,116,817 A | 5/1992 | Anik |
| 5,135,915 A | 8/1992 | Czarniecki et al. |
| 5,192,744 A | 3/1993 | Bouck et al. |
| 5,229,135 A | 7/1993 | Philippon et al. |
| 5,260,068 A | 11/1993 | Chen |
| 5,260,069 A | 11/1993 | Chen |
| 5,294,446 A | 3/1994 | Schlameus et al. |
| 5,323,907 A | 6/1994 | Kalvelage |
| 5,336,168 A | 8/1994 | Sibalis |
| 5,352,668 A | 10/1994 | Burgeson et al. |
| 5,437,287 A | 8/1995 | Phillips et al. |
| 5,456,923 A | 10/1995 | Nakamichi et al. |
| 5,461,140 A | 10/1995 | Heller et al. |
| 5,508,040 A | 4/1996 | Chen |
| 5,516,527 A | 5/1996 | Curatolo |
| 5,567,441 A | 10/1996 | Chen |
| 5,622,721 A | 4/1997 | Dansereau et al. |
| 5,665,378 A | 9/1997 | Davis et al. |
| 5,686,105 A | 11/1997 | Kelm et al. |
| 5,700,410 A | 12/1997 | Nakamichi et al. |
| 5,837,280 A | 11/1998 | Kenealy et al. |
| 5,837,284 A | 11/1998 | Mehta et al. |
| 5,840,329 A | 11/1998 | Bai |
| 5,869,090 A | 2/1999 | Rosenbaum |
| 5,932,545 A | 8/1999 | Henkin et al. |
| 5,977,175 A | 11/1999 | Lin |
| 6,152,142 A | 11/2000 | Tseng |
| 6,326,019 B1 | 12/2001 | Tseng et al. |
| 6,391,452 B1 | 5/2002 | Antonsen et al. |
| 6,465,014 B1 | 10/2002 | Moroni et al. |
| 6,923,983 B2 | 8/2005 | Morgan et al. |
| 6,929,801 B2 | 8/2005 | Klose et al. |
| 6,932,983 B1 | 8/2005 | Straub et al. |
| 6,946,144 B1 | 9/2005 | Jordan |
| 7,494,802 B2 | 2/2009 | Tseng et al. |
| 8,153,162 B2 | 4/2012 | Tseng |
| 8,182,840 B2 | 5/2012 | Tseng |
| 8,182,841 B2 | 5/2012 | Tseng |
| 8,187,639 B2 | 5/2012 | Tseng |
| 8,420,126 B2 | 4/2013 | Tseng et al. |
| 8,440,235 B2 | 5/2013 | Tseng et al. |
| 8,455,009 B2 | 6/2013 | Tseng et al. |
| 8,460,714 B2 | 6/2013 | Tseng et al. |
| 2001/0041684 A1 | 11/2001 | Lezdey |
| 2004/0048796 A1 | 3/2004 | Hariri et al. |
| 2004/0057938 A1 | 3/2004 | Ghinelli |
| 2004/0126323 A1 | 7/2004 | Shevchuk et al. |
| 2004/0181240 A1 | 9/2004 | Tseng et al. |
| 2007/0071740 A1 | 3/2007 | Tseng et al. |
| 2007/0071828 A1 | 3/2007 | Tseng et al. |
| 2007/0231401 A1 | 10/2007 | Tseng et al. |
| 2008/0069895 A1 | 3/2008 | Liu et al. |
| 2008/0102135 A1 | 5/2008 | Ollivier |
| 2008/0108045 A1 | 5/2008 | Ghinelli |
| 2008/0193554 A1 | 8/2008 | Dua et al. |
| 2008/0299087 A1 | 12/2008 | Tseng et al. |
| 2009/0130162 A2 | 5/2009 | Pathak et al. |
| 2009/0226499 A1 | 9/2009 | Wisniewski et al. |
| 2010/0047214 A1 | 2/2010 | Abramson et al. |
| 2010/0104539 A1 | 4/2010 | Daniel et al. |
| 2012/0083445 A1 | 4/2012 | Tseng et al. |
| 2012/0141595 A1 | 6/2012 | Tseng et al. |
| 2012/0207848 A1 | 8/2012 | Tseng |
| 2012/0207849 A1 | 8/2012 | Tseng |
| 2012/0269880 A1 | 10/2012 | Tseng et al. |
| 2012/0328690 A1 | 12/2012 | Tseng et al. |
| 2013/0156863 A1 | 6/2013 | Tseng et al. |
| 2013/0195993 A1 | 8/2013 | Tseng et al. |
| 2013/0195994 A1 | 8/2013 | Tseng et al. |
| 2013/0280344 A1 | 10/2013 | Tseng et al. |
| 2013/0344163 A1 | 12/2013 | Tseng et al. |
| 2014/0112998 A1 | 4/2014 | Tseng et al. |
| 2014/0147511 A1 | 5/2014 | Tseng et al. |

FOREIGN PATENT DOCUMENTS

| | | |
|---|---|---|
| JP | H01256967 A | 10/1989 |
| KR | 2001-098716 A | 11/2001 |
| WO | WO98-37903 | 9/1998 |
| WO | WO03-077794 A2 | 9/2003 |
| WO | WO2004-026244 | 1/2004 |
| WO | WO2004-060388 | 7/2004 |
| WO | WO2005-060988 A1 | 7/2005 |
| WO | WO2006-094247 A2 | 9/2006 |
| WO | WO2007-038686 | 4/2007 |
| WO | WO2011-031489 | 3/2011 |
| WO | WO-2012149486 A1 | 11/2012 |
| WO | WO-2014011813 A1 | 1/2014 |

OTHER PUBLICATIONS

Derynk, R. and Feng, X., "TGF-β receptor signaling," Biochem. Biophys. Acta. 1333:F105-F150 (1997).

EP 06804232.4 Search Report mailed May 10, 2010.

Fortunato et al., "Interleukin-10 and transforming growth factor-β inhibit amniochorion tumor necrosis factor-α production by contrasting mechanisms of action: Therapeutic implications in prematurity," Am. J. Obstet. Gynecol. 177(4):803-809 (1997).

Fortunato et al., "Interleukin-10 inhibition of interleukin-6 in human amniochorionic membrane: Transcriptional regulation," Am. J. Obstet. Gynecol. 175:1057-1065 (1996).

Fortunato et al., "The effect of transforming growth factor and interleukin-10 on interleukin-8 release by human amniochorion may regulate histologic chorioamnionitis," Am. J. Obstet. Gynecol. 179(3):794-799 (1998).

Fries et al., "Inter-α-inhibitor, hyaluronan and inflammation," Acta Biochim. Polonica 50(3):735-742 (2003).

Gabbiani, G., "The myofibroblast in wound healing and fibrocontractive diseases," J. Pathol. 200:500-503 (2003).

Grande, J.P., "Role of Transforming Growth Factor-β in Tissue Injury and Repair," Proc. Soc. Exp. Biol. Med. 214:27-40 (1997).

Guo, Carbopol® Polymers for Pharmaceutical Drug Delivery Applications. Drug Delivery Technology 3(6):1-4 (2003).

Hales et al., "TGF-β-1 induces lens cells to accumulate α-smooth muscle actin, a marker for subcapsular cataracts," Curr. Eye Res. 13:885-890 (1994).

Hanada et al., "Regulation of cytokine signaling and inflammation," Cytokine & Growth Factor Reviews 13(4-5):413-421 (2002).

Hao et al., "Identification of Antiangiogenic and Antiinflammatory Proteins in Human Amniotic Membrane," Cornea 19(3):348-352 (2000).

He et al., "A simplified system for generating recombinant adenoviruses," PNAS USA 95:2509-2514 (1998).

He et al., "Biochemical Characterization and Function of Complexes Formed by Hyaluronan and the Heavy Chains of Inter-a-inhibitor (HC-HA) Purified from Extracts of Human Amniotic Membrane," J. Biol. Chem. 284(30):20136-20146 (2009).

Heiligenhaus et al., "Improvement of HSV-1 Necrotizing Keratitis with Amniotic Membrane Transplantation," Invest. Ophthalmol. Vis. Sci. 42(9):1969-1974 (2001).

Howes et al., "Receptor for Advanced Glycation End Products and Age-Related Macular Degeneration," Invest. Ophthal. Vis. Sci. 45(10):3713-3720 (2004).

Jester et al., "Corneal Stromal Wound Healing in Refractive Surgery: the Role of Myofibroblasts," Prog. Retin. Eye Res. 18(3):311-356 (1999).

Jester et al., "Induction of α-Smooth Muscle Actin Expression and Myofibroblast Transformation in Cultured Cornea Keratocytes," Cornea 15(5):505-516 (1996).

Keelan et al., "Activin A Exerts both Pro- and —Anti-inflammatory Effects on Human Term Gestational Tissues," Placenta 31:38-43 (2000).

(56) References Cited

OTHER PUBLICATIONS

Kopp et al., "Abrogation of Transforming Growth Factor-beta Signaling by SMAD7 Inhibits Collagen Gel Contraction of Human Dermal Fibroblasts," J. Biol. Chem. 280(22):21570-21576 (2005).

Lawrence, D.A., "Transforming Growth Factor-β: a general review," Eur. Cytokine Netw. 7:363-374 (1996).

Lee, H.G. and Cowman, M.K., "An Agarose Gel Electrophoretic Method for Analysis of Hyaluronan Molecular Weight Distribution," Anal. Biochem. 219:278-287 (1994).

Lee, S. and Tseng, S., "Amniotic Membrane Transplantation for Persistent Epithelial Defects with Ulceration," Am. J. Ophthalmol. 123:303-312 (1997).

Lee, S. B. et al., "Suppression of TGF-β signaling in both normal conjuctival fibroblasts and pterygial body fibroblasts by amniotic membrane," Curr. Eye Res. 20(4):325-334 (2000).

Li, et al. "An Experimental Study of the Effects of Human Amniotic Membrane on Human Retinal Pigment Epithelial Cell Proliferation in vitro." Acta Acadamiae Medicinae Militaris Tertia, 2003, vol. 25, No. 5, pp. 407-409 (with English Abstract).

Lieberman et al., Pharmaceutical Dosage Forms, 2 Ed. vol. 1, pp. 209-214 (1990).

Liu et al., "Biocompatibility and stability of disulfide-corsslinked hyaluronan films," Biomaterials 26(23):4737-4746 (2005).

Logan, A. et al., "Decorin Attenuates Gliotic Scar Formation in the Rat Cerebral Hemisphere," Exp. Neurol. 159:504-510 (1999).

Marek, A. et al., "TGF-β—(transforming growth factor-β) in chronic inflammatory conditions-a new diagnostic and prognostic marker?" Med. Sci. Monitl 8(7):RA145-RA151 (2002).

Massague, J. and Chen, Y., "Controlling TGF-β signaling," Genes and Development 14:627-644 (2000).

Milner et al., "TSG-6: a multifunctional protein associated with inflammation," J. Cell Sci. 116(10):1863-1873 (2003).

Moller-Pedersen. T. et al., "Neutralizing antibody to TGF-β modulates stromal fibrosis but not regression of photoablative effect following PRK," Curr. Eye Res. 17:736-747 (1998).

Monteleone et al., "SMAD7 in TGF-b-mediated negative regulation of gut inflammation," Trends in Immunology 25(10):513-517 (2004).

Mukhopadhyay et al., "Two distinct populations of tumor necrosis factor-stimulated gene-6 protein in the extracellular matrix of expanded mouse cumulus cell-oocyte complexes," Archives of Biochemistry and Biophysics 394(2): 173-181 (2001).

Na, B. et al., "Analysis of Human Amniotic Membrane Components as Proteinase Inhibitors for Development of Therapeutic Agent for Recalcitrant Keratitis," Trophoblast Res. 13:453-466 (1999).

Nakao et al., "SMAD7: a new key player in TGF-b-associated disease," Trends in Molecular Medicine 8(8):361-363 (2002).

Neumann et al., "High molecular weight hyaluronic acid inhibits advanced glycation endproduct-induced NF-kB activation and cytokine expression," FEBS Ltrs. 453:283-287(1999).

Oikawa, J. et al., "Inhibition of Angiogenesis by 15-Deoxyspergualin," J. Antibiotics 44(9):1033-1035 (1991).

Ochsner et al., "Decreased expression of tumor necrosis factor-alpha-stimulated gene 6 in cumulus cells of the cyclooxygenase2 and EP2 null mice," Endocrinology 144: 1008-1019 (2003).

PCT/US06/37906 IPRP dated Apr. 1, 2008.

PCT/US06/37906 WO Search Report and Written Opinion dated Jul. 11, 2007.

PCT/US10/032452 International Search Report mailed Dec. 27, 2010.

PCT/US10/032452 WO IPRP and Written Opinion dated Oct. 25, 2011.

PCT/US10/46675 IPRP dated Feb. 28, 2012.

PCT/US10/46675 Search Report and Written Opinion dated May 30, 2011.

Petraglia, F. et al., "Inhibin and Activin in Human Fetal Membranes: Evidence of a Local Effect on Prostaglandin Release," J. Clin. Endocrinol. Metab. 77(2):542-548 (1993).

Prabhasawat, P. et al., "Comparison of Conjunctival Autografts, Amniotic Membrane Grafts, and Primary Closure for Pterygium Excision," Ophthalmology 104:974-985 (1997).

Riley, S. et al., "Production of inhibin forms by the fetal membranes, decidua, placenta and fetus at parturition," Hum. Reprod. 15:578-583 (2000).

Romero, R. et al., "The natural interleukin-1 receptor antagonist in the fetal, maternal, and amniotic fluid compartments: The effect of gestational age, fetal gender, and intrauterine infection," Am. J. Obstet. Gynecol. 171:912-921 (1994).

Ronnov-Jessen, L. et al., "Induction of α-Smooth Muscle Actin by Transforming Growth Factor-β1 in Quiescent Human Breast Gland Fibroblasts," Lab. Invest. 68:696-707 (1993).

Rovere, et al., "The long pentraxin PTX3 binds to apoptotic cells and regulates their clearance by antigen-presenting dendritic cells," Blood 96(13):4300-4306 (2000).

Rugg, et al, "Characterization of complexes formed between TSG-6 and inter-alpha-inhibitor that act as intermediates in the covalent transfer of heavy chains onto hyaluronan," J Biol Chem, 280(27):25674-25686 (2005).

Sanggaard, et al, "The transfer of heavy chains from bikunin proteins to hyaluronan requires both TSG-6 and HC2," J Biol Chem, 283(27):18530-18537 (2008).

Serini, G. et al., "The Fibronectin Domain ED-A Is Crucial for Myofibroblastic Phenotype Induction by Transforming Growth Factor-β1," J. Cell. Biol. 142:873-881 (1998).

Shah, M. et al., "Control of scarring in adult wounds by neutralising antibody to transforming growth factor β," Lancet 339:213-214 (1992).

Singh et al., Encyclopedia of Pharmaceutical Technology, $2^{nd}$ ed., pp. 751-753 (2002).

Solomon et al., "Suppression of Interleukin 1a and interleukin 1b in human limbal epithelial cells cultured on the amniotic membrane stromal matrix," Br. J. Ophthalmol 85:444-449 (2001).

Travis et al., "Hyaluronan Enhances Contraction of Collagen by Smooth Muscle B Cells and Adventitial Fibroblasts Role of CD44 and Implications for Constrictive Remodeling," Cir. Res. 88:77-83 (2001).

Tseng, S. et al., "How Does Amniotic Membrane Work?" Ocular Surface J. 2(3):177-187 (2004).

Tseng, S. et al., "Amniotic Membrane Transplantation With or Without Limbal Allografts for Corneal Surface Reconstruction in Patients With Limbal Stem Cell Deficiency," Arch. Ophthalmol. 116:431-441 (1998).

Tseng, S. et al., "Suppression of Transforming Growth Factor-Beta Isoforms, TGF-β Receptor Type II, and Myofibroblast Differentiation in Cultured Human Corneal and Limbal Fibroblasts by Amniotic Membrane Matrix," J. Cell Physiol., 179:325-335 (1999).

U.S. Appl. No. 11/528,902 Notice of Allowance mailed Mar. 7, 2012.
U.S. Appl. No. 11/528,902 Office Action mailed Jan. 27, 2011.
U.S. Appl. No. 11/528,902 Office Action mailed Dec. 16, 2009.
U.S. Appl. No. 11/528,902 Office Action mailed Apr. 2, 2009.
U.S. Appl. No. 11/528,902 Office Action mailed Sep. 8, 2010.
U.S. Appl. No. 11/528,980 Notice of Allowance mailed Feb. 23, 2012.
U.S. Appl. No. 11/528,980 Office Action mailed Jan. 10, 2011.
U.S. Appl. No. 11/528,980 Office Action mailed Oct. 15, 2010.
U.S. Appl. No. 11/528,980 Office Action mailed Nov. 13, 2008.
U.S. Appl. No. 11/528,980 Office Action mailed Aug. 11, 2009.
U.S. Appl. No. 11/529,658 Notice of Allowance mailed Mar. 8, 2012.
U.S. Appl. No. 11/529,658 Office Action mailed Jan. 27, 2011.
U.S. Appl. No. 11/529,658 Office Action mailed Dec. 16, 2009.
U.S. Appl. No. 11/529,658 Office Action mailed Apr. 3, 2009.
U.S. Appl. No. 11/529,658 Office Action mailed Sep. 3, 2010.
U.S. Appl. No. 11/535,924 Notice of Allowance mailed Mar. 20, 2012.
U.S. Appl. No. 11/535,924 Office Action mailed Jan. 31, 2011.
U.S. Appl. No. 11/535,924 Office Action mailed Dec. 16, 2009.
U.S. Appl. No. 11/535,924 Office Action mailed Mar. 31, 2009.
U.S. Appl. No. 11/535,924 Office Action mailed Sep. 8, 2010.
U.S. Appl. No. 13/453,840 Office Action mailed Aug. 21, 2012.

Verbeek, M. et al., "Induction of alpha-smooth muscle actin expression in cultured human brain pericytes by transforming growth factor-beta 1," Am. J. Pathol. 144:372-382 (1994).

(56) References Cited

OTHER PUBLICATIONS

Yamaguchi, Y. et al., "Negative regulation of transforming growth factor-β by the proteoglycan decorin," Nature 346(6281):281-284 (1990).
Azuara-Blanco et al. Amniotic Membrane Transplantation for Ocular Surface Reconstruction. Invest. Ophthalmol. Vis. Sci. 39(4):S428 (1998).
Azuara-Blanco et al. Amniotic Membrane Transplantation for Ocular Surface Reconstruction. Br. J. Ophthalmol. 83(4):399-402 (1999).
Badawy et al. Evaluation of Tissue Healing and Adhesion Formation After an Intraabdominal Amniotic Membrane Graft in the Rat. J. Reproductive Med. 34:198 (1989).
Barton et al. Amniotic Membrane Transplantation in Glaucoma Surgery. Invest Ophthalmol Vis Sci 38:S473 (1997).
Budenz et al. Amniotic Membrane Transplantation for Repair of Leaking Glaucoma Filtering Blebs. Am. J. Ophthalmol. 130:580-588 (2000).
Chen et al. Amniotic Membrane Transplantation for Severe Neurotrophic Corneal Ulcers. Br. J. Ophthalmol. 84:826-833 (2000).
Cho et al. Conjunctival Epithelial Cells Cultured on Human Amniotic Membrane Fail to Transdifferentiate into Corneal Epithelial-type Cells. Cornea, 18:216-224 (1999).
Cho et al. Conjunctival Epithelial Cells Cultured on Human Amniotic Membrane Do Not Transdifferentiate into Corneal Epithelial Type Cells. Invest. Ophthalmol. Vis. Sci. 39(4):S428 (1998).
Choi et al. Effect of the Application of Human Amniotic Membrane on Rabbit Corneal wound Healing After Excimer Laser Photorefractive Keratectomy. Cornea, 17:389-395 (1998).
Colon et al. Transfer of Inter-α-inhibitor Heavy Chains to Hyaluronan by Surface-linked Hyaluronan-TSG-6 Complexes. J. Biol. Chem. 2009. 284:2320-2331.
Derotth. Plastic Repair of Conjunctival Defects with Fetal Membranes. Archives of Ophthalmology 23:522-525 (1940).
Dua et al. Amniotic Membrane Transplantation. Br. J. Ophthalmol. 83:748-752 (1999).
Franch et al. Human Amniotic Membrane Transplantation. Invest. Ophthalmol. Vis. Sci. 39(4):S90 (1998).
Fujishima et al. Trabeculectomy With the Use of Amniotic Membrane for Uncontrolled Glaucoma, Ophthalmic. Surg. Lasers 29:428-431 (1998).
Fukuda et al. Differential Distribution of Subchains of the Basement Membrane Components Type IV Collagen and Laminin Among the Amniotic Membrane, Cornea, and Conjunctiva. Cornea 18:73-79 (1999).
Kim et al. Temporary Amniotic Membrane Graft Promotes Healing and Inhibits Protease Activity in Corneal Wound Induced by Alkali Burn in Rabbits. Invest. Ophthalmol. Vis. Sci. 39(4):S90 (1998).
Kim et al. Amniotic Membrane Patching Promotes Healing and Inhibits Protease Activity on Wound Healing Following Acute Corneal Alkali Burns. Exp. Eye Res. 70:329-337 (1998).
Kim et al. Clinical Uses of Human Amniotic Membrane for Ocular Surface Diseases. In: Advances in Corneal Research, Lass, J.H. ed. (NY: Plenum Press), pp. 117-134 (1997).
Kim et al. The Effects on Inhibition of Corneal Neovascularization After Human Amniotic Membrane Transplantation in Severely Damaged Rabbit Corneas. Korean J. Ophthalmol. 9:32-46 (1995).
Kim et al. Transplantation of Preserved Human Amniotic Membrane for Surface Reconstruction in Severely Damaged Rabbit Corneas. Cornea 15:473-84 (1995).
Klen. Influence of Ionizing Sterilization on the Permeability of Human Chorio-Amniotic, Dermo-Epidermal and Fascial Grafts. Res. Exp. Med. 167(1):15-21 (1976).
Koizumi et al. Amniotic Membrane as a Substrate for Cultivating Limbal Corneal Epithelial Cells for Autologus Transplantation in Rabbits. Cornea, 19:65-71 (2000).
Koizumi et al. Cultivation of Corneal Epithelial Cells on Intact and Denuded Human Amniotic Membrane. Invest. Ophthalmol. Vis. Sci. 41:2506-2513 (2000).
Koizumi et al. Growth Factor mRNA and Protein in Preserved Human Amniotic Membrane. Curr. Eye Res. 20:173-177 (2000).
Kruse et al. Cryoperserved Human Amniotic Membrane for Ocular Surface Reconstruction. Graefe's Arch. Clin. Exp. Ophthalmol. 238:68-75 (2000).
Kruse et al. Multilayer Amniotic Membrane Transplantation for Reconstruction of Deep Corneal Ulcers. Ophthalmology 106:1504-1511 (1999).
Ma et al. Amniotic Membrane Graft for Primary Pterygium: Comparison with Conjuctival Autograft and Topical Mitomycin C Treatment. Br. J. Ophthalmol. 84:973-978 (2000).
Meller. Conjunctival Epithelial Cell Differentiation on Amniotic Membrane. Invest. Ophthalmol. Vis. Sci. 40:878-886 (1999).
Meller et al. Amniotic Membrane Transplantation for Acute Chemical or Thermal Burns. Ophthalmology. 107:980-990 (2000).
Meller et al. Amniotic Membrane Transplantation for Symptomatic Conjunctivochalasis Refractory to Medical Treatments. Cornea 19:796-803 (2000).
Meller et al. In Vitro Conjunctival Epithelial Differentiation on Preserved Human Amniotic Membrane. Invest. Ophthalmol. Vis. Sci. 39(4):S428 (1998).
Na et al. Analysis of Human Amniotic Membrane Components as Proteinase Inhibitors for Development of Therapeutic Agent of Recalcitrant Keratitis. Invest. Ophthalmol. Vis. Sci. 39(4):S90 (1998).
Park et al. Modulation of Acute Inflammation and Keratocyte Death by Suturing, Blood and Amniotic Membrane in PRK. Invest. Ophthalmol. Vis. Sci. 41:2906-2914 (2000).
Park et al. Temperature Cooling Reduces Keratocyte Death in Excimer Laser Ablated Corneal and Skin Wounds. Invest. Ophthalmol. Vis. Sci. 39(4):S449 (1998).
PCT/US98/03665 International Search Report mailed Jun. 23, 1998.
PCT/US2011/042679 International Preliminary Report on Patentability mailed Jan. 8, 2013.
PCT/US2011/042679 International Search Report and Written Opinion mailed Mar. 9, 2012.
PCT/US2012/041685 International Search Report and Written Opinion mailed Aug. 14, 2012.
PCT/US2012/041685 International Preliminary Report on Patentability mailed Dec. 10, 2013.
PCT/US2012/035678 International Search Report and Written Opinion mailed Oct. 1, 2012.
PCT/US2012/035678 International Preliminary Report on Patentability mailed Oct. 29, 2013.
Pires et al. Amniotic Membrane Transplantation or Limbal Conjuctival Autograft for Limbal Stem Cell Deficiency Induced by 5-fluorouracil in Glaucoma Surgeries. Cornea 19:284-287 (2000).
Pires et al. Amniotic Membrane Transplantation for Symptomatic Bullous Keratopathy. Arch. Ophthalmol. 117(10):1291-1297 (1999).
Prabhasawat et al. Impression Cytology Study of Epithelial Phenotype of Ocular Surfaces Reconstructed by Preserved Human Amniotic Membrane. Arch Ophthalmol. 115:1360-1367 (Nov. 1997).
Rodriguez-Ares et al. Repair of Scleral Perforation with Preserved Scleral and Amniotic Membrane in Marfan's Syndrome. Ophthalmic Surg. Lasers 30(6):485-487 (1999).
Sato et al. Role of Growth Factors for Ocular Surface Reconstruction After Amniotic Membrane Transplantation. Invest. Ophthalmol. Vis. Sci. 39(4):S428 (1998).
Shimazaki et al. Amniotic Membrane Transplantation for Ocular Surface Reconstruction in Patients with Chemical and Thermal Burns. Ophthalmology. 104(12):2068-2076 (1997).
Shimazaki et al. Transplantation of Amniotic Membrane and Limbal Autograft for Patients with Recurrent Pterygium Associated with Symblepharon. Br. J. Ophthalmol. 82(3):235-240 (1998).
Sorsby Amniotic Membrane Grafts in Burns. In: Modern Trends in Ophthalmology. Sorsby, A. ed. (NY: Paul B. Hoeber, Inc.), pp. 504-510 (1947).
Sorsby et al. Amniotic Membrane Grafts in Caustic Burns of the Eye (Burns of the Second Degree). Br. J. Ophthalmology 30:337-345 (1946).
Sorsby et al. Further Experience with Amniotic Membrane Grafts in Caustic Burns of the Eye. Br. J. Ophthalmology 31:409-18 (1947).

(56) References Cited

OTHER PUBLICATIONS

Taylor et al. Rate of Re-Epithelialization Following Amniotic Membrane Transplantation. Invest. Ophthalmol. Vis. Sci. 39(4):S1038 (1998).
Trelford. The Amnion in Surgery, Past and Present. Am J. Obstet. Gynecol 134:833 (1979).
Tsai. Corneal Surfaces Reconstruction by Amniotic Membrane with Cultivated Autologous Limbo-Corneal Epithelium. Invest. Ophthalmol. Vis. Sci. 39(4):S429 (1998).
Tsai et al. Reconstruction of Damaged Corneas by Transplantation of Autologous Limbal Epithelial Cells. N. Eng. J. Med. 343:86-93 (2000).
Tseng et al. Down-regulation of TGF-.beta.1, .beta.2, .beta.3 and TGF-.beta. Receptor II Expression in Human Corneal Fibroblasts by Amniotic Membrane. Invest. Ophthalmol. Vis. Sci. 39(4):S428 (1998).
Tseng et al. Amniotic Membrane Transplantation for Conjunctival Surface Reconstruction. Am. J. Ophthalmol. 124:765-774 (Dec. 1997).
Tsubota et al. Surgical Reconstruction of the Ocular Surface in Advanced Ocular Cicatricial Pemphigoid and Stevens-Johnson Syndrome. Am J. Ophthalmology 122:38-52 (1996).
U.S. Appl. No. 09/027,109 Notice of Allowance mailed Jul. 5, 2000.
U.S. Appl. No. 09/027,109 Office Action mailed Dec. 7, 1999.
U.S. Appl. No. 09/027,109 Office Action mailed Jun. 5, 2000.
U.S. Appl. No. 13/262,725 Office Action mailed Jul. 17, 2014.
U.S. Appl. No. 13/802,264 Office Action mailed Nov. 28, 2014.
U.S. Appl. No. 13/322,896 Office Action mailed Oct. 22, 2014.
Wang et al. Corneal Haze is Reduced by Amniotic Membrane Matrix in Excimer Laser Photoablation in Rabbits. Invest Ophthalmol Vis Sci 38:S405 (1997).
Yokomori et al. Advantages and Pitfalls of Amnion Inversion Repair for the Treatment of Large Unruptured Omphalocele: Results of 22 Cases. Journal of Pediatric Surgery 23:882-884 (1992).
Tan et al. Structural and Biological Comparison of Cryopreserved and Fresh Amniotic membrane Tissues. Journal Biomaterial and Tissue Engineering 4:379-388 (2014).
Cooke et al. Comparison of cryopreserved amniotic membrane and umbilical cord tissue with dehydrated amniotic membrane/chorion tissue. J Wound Care 23(10):465-474 (2014).
Diaz-Prado et al. Potential use of the human amniotic membrane as a scaffold in human articular cartilage repair. Cell Tissue Bank 11:183-195 (2010).
Hatano et al. Transplantation of amniotic membrane and limbal autograft in the treatment of recurrent pterygium. Clinical Ophthalmology 50(6):1101-1104 (1996) (English Abstract).
Hori. Amniotic Membrane Transplantation and Immune Reaction. Folia Ophthalmologica Japonica 56(9):722-727 (2005) (English Abstract).
Jadin et al. Characterization of a Novel Recombinant Hyaluronan Binding Protein for Tissue Hyaluronan Detection. Journal of Histochemistry & Cytochemistry 62(9):672-683 (2014).
PCT/US2013/049983 International Preliminary Report on Patentability dated Jan. 22, 2015.
PCT/US2013/049983 International Search Report and Written Opinion dated Nov. 29, 2013.
Sakurai et al. Characterization of the Role of PTX2 in Enhancing the Anti-angiogenci Action of HC.HA Purified From the Chorion. Arvo Annual Meeting Abstract Search and Program Planner. 2011:4881 (May 2011).
Tseng et al. Amniotic Membrane Transplantation with or without Limbal Transplantation for Corneal Surface Reconstruction in Patients with Limbal Stem Cell Deficiency. Arch Ophthalmol. 124(6):765-774 (Apr. 1998).
U.S. Appl. No. 13/262,725 Office Action dated Feb. 25, 2015.
U.S. Appl. No. 13/802,204 Office Action dated Feb. 26, 2015.
U.S. Appl. No. 13/802,359 Office Action dated Dec. 10, 2014.
U.S. Appl. No. 13/802,447 Office Action dated Dec. 15, 2014.

P Value Comparison on Two Sides

|       | PL        | FRO/P    | FRO/F     | FRE/P     | FRE/F |
|-------|-----------|----------|-----------|-----------|-------|
| PL    | X         | x        | x         | x         | x     |
| FRO/P | 0.007692  |          | x         | x         | x     |
| FRO/F | 0.007268  | 0.30195  | x         | x         | x     |
| FRE/P | 0.012165  | 0.024442 | 0.2375045 |           | x     |
| FRE/F | 0.500177  | 0.115462 | 0.1283315 | 0.14812627 | x     |

AMNIOTIC MEMBRANE PREPARATIONS AND PURIFIED COMPOSITIONS AND ANTI-ANGIOGENESIS TREATMENT

CROSS-REFERENCE

This application is a continuation application and claims the benefit under 35 U.S.C. §120 of U.S. application Ser. No. 13/453,840 filed on Apr. 23, 2012, which is a continuation of U.S. application Ser. No. 11/535,924 filed on Sep. 27, 2006, which issued as U.S. Pat. No. 8,187,639 on May 29, 2012, which claims the benefit of U.S. Provisional Application No. 60/720,760, filed Sep. 27, 2005, all of which are incorporated herein by reference in their entirety.

STATEMENT AS TO FEDERALLY SPONSORED RESEARCH

The invention was made with United States government support under grant number R01 EY06819 awarded by the National Institutes of Health. The United States government may have certain rights in the invention.

FIELD OF THE INVENTION

The invention relates generally to the fields of biology and pharmaceuticals. More particularly, the inventions relates to compositions and methods for modulating cellular and pathological processing using a combination of compounds that can be found in amniotic membrane preparations.

BACKGROUND OF THE INVENTION

The placenta is a temporary organ that surrounds the fetus during gestation. The placenta allows for transport of gases and nutrients, and also provides other metabolic and endocrine functions. The placenta is composed of several tissue types. The umbilical cord connects the placenta to the fetus, and transports oxygen to the fetus. The umbilical cord has two arteries and a vein. Wharton's jelly, a specialized gelatinous connective tissue material, surrounds the umbilical cord to protect it from damage during fetal movement and development. The outer "shell" of the placenta is known as the "chorion." Much of the placental disc is composed of chorionic villi, which are extensions of the chorionic villous tree. Through these structures, fetal nutrition exchange occurs. The amniotic membrane (AM) is an avascular membranous sac that is filled with amniotic fluid. This membrane is the innermost membrane surrounding a fetus in the amniotic cavity. This tissue consists of an epithelial layer and a subadjacent avascular stromal layer.

SUMMARY OF THE INVENTION

Described herein are purified compositions and amniotic membrane preparations (that is, compositions that are prepared from amniotic membrane materials, including the amniotic membrane, amniotic stroma and amniotic jelly). In some embodiments, at least one component of the purified compositions are obtained from amniotic membrane preparations. Also described herein are purified compositions in which at least one component of the purified composition is obtained from human placenta and chorion. Also described herein are methods for preparing any of the aforementioned purified compositions and preparations. Also described herein are methods for storing and preserving any of the aforementioned purified compositions and preparations. Also described herein are methods for using any of the aforementioned purified compositions and preparations, including preservative methods, cell culture methods, tissue culture methods, therapeutic methods, prophylactic methods and cosmetic methods.

Various AM preparations exert a number of physiologically significant effects in mammalian cells and intact mammalian tissues. Such effects include suppressing TGF β signaling, increasing apoptosis of macrophages, decreasing cellular proliferation of, decreasing cellular migration of, and increasing apoptosis of vascular endothelial cells, protecting corneal and limbal epithelial cells and keratocytes from apoptosis induced by storage or by dispase treatment, and decreasing inflammation in tissues. In addition to pieces of intact AM, other preparations described herein include pieces of AM stroma, processed (e.g., ground or pulverized) AM or AM stroma, and various extracts of intact AM and AM stroma. AM extracts can be in liquid or lyophilized powder form. The compositions also include thickened or gel forms of AM extracts which can be made by mixing the AM extracts with a thickener such as one or more extra cellular matrix components (ECM). A large number of ECM components are known such as collagen, hyaluronic acid (HA), and fibrin.

In some embodiments, a method for inhibiting angiogenesis in a subject is provided, by providing an effective amount of an angiogenesis inhibition composition to a subject in need of angiogenesis inhibition, where the composition comprises at least one component prepared from human amniotic material selected from a human amniotic membrane, a human amniotic jelly, a human amniotic stroma, or a combination thereof extracted from an amniotic membrane. The component can be extracted from human amniotic material. The human amniotic material can be, for example, human amniotic stroma. The composition can comprise, for example, cross-linked high molecular weight hyaluronan (HA), Tumor necrosis factor-stimulated gene 6 (TSG-6), Pentraxin (PTX-3), and Thrombospondin (TSP-1). The extraction procedure can involve, for example, obtaining a frozen or previously-frozen human placenta, thawing the placenta and isolating the human amniotic material from the thawed placenta, homogenizing the human amniotic material in a suitable buffer, optionally lyophilizing the homogenate to a powder, and admixing the homogenate or the powder with a pharmaceutically acceptable carrier for a non-solid dosage form or an extended release solid dosage form. In certain embodiments, the preparation procedure can substitute the step of lyophilizing the homogenate with the step of centrifuging the homogenate, isolating the supernatant from the centrifuged homogenate, and optionally lyophilizing the supernatant to a powder. The subject can be, for example, a human with cancer or age-related macular degeneration. The composition can be in the form of a non-solid dosage form or an extended release solid dosage form. The composition have, for example, the following properties: induces apoptosis of endothelial cells involved in vascular formation, prevents migration of endothelial cells involved in vascular formation, and prevents tube formation of endothelial cells involved in vascular formation.

Although preparations, materials, and methods similar or equivalent to those described herein can be used in the practice or testing of the present invention, suitable preparations, methods and materials are described herein. All publications mentioned herein are incorporated by reference in their entirety. In the case of conflict, the present specification, including definitions will control. In addition, the particular embodiments discussed below are illustrative only and not intended to be limiting.

Certain Definitions

The term "acceptable" with respect to a formulation, composition or ingredient, as used herein, means having no persistent detrimental effect on the general health of the subject being treated.

"Antioxidants" include, for example, butylated hydroxytoluene (BHT), sodium ascorbate, ascorbic acid, sodium metabisulfite and tocopherol. In certain embodiments, antioxidants enhance chemical stability where required.

"Binders" impart cohesive qualities and include, e.g., alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crosspovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, and the like.

The term "carrier," as used herein, refers to relatively non-toxic chemical compounds or agents that facilitate the incorporation of a compound into cells or tissues.

"Carrier materials" include any commonly used excipients in pharmaceutics and should be selected on the basis of compatibility with compounds disclosed herein, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" may include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins1999).

The terms "co-administration" or the like, as used herein, are meant to encompass administration of the selected therapeutic agents to a single patient, and are intended to include treatment regimens in which the agents are administered by the same or different route of administration or at the same or different time.

The term "delayed release" as used herein refers to the delivery so that the release can be accomplished at some generally predictable location more distal to that which would have been accomplished if there had been no delayed release alterations.

"Dispersing agents," and/or "viscosity modulating agents" include materials that control the diffusion and homogeneity of a drug through liquid media or a granulation method or blend method. In some embodiments, these agents also facilitate the effectiveness of a coating or eroding matrix. Exemplary diffusion facilitators/dispersing agents include, e.g., hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizcers such as cellulose or triethyl cellulose can also be used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution. In certain embodiments, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

An "enteric coating" is a substance that remains substantially intact in the stomach but dissolves and releases the drug in the small intestine or colon. Generally, the enteric coating comprises a polymeric material that prevents release in the low pH environment of the stomach but that ionizes at a higher pH, typically a pH of 6 to 7, and thus dissolves sufficiently in the small intestine or colon to release the active agent therein.

"Filling agents" include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition including a compound as disclosed herein required to provide a clinically significant decrease in disease symptoms without undue adverse side effects. An appropriate "effective amount" in any individual case may be determined using techniques, such as a dose escalation study. The term "therapeutically effective amount" includes, for example, a prophylactically effective amount. An "effective amount" of a compound disclosed herein, is an amount effective to achieve a desired pharmacologic effect or therapeutic improvement without undue adverse side effects. It is understood that "an effect amount" or "a therapeutically effective amount" can vary from subject to subject, due to variation in metabolism of the composition, age, weight, general condition of the subject, the condition being treated, the severity of the condition being treated, and the judgment of the prescribing physician.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The terms "kit" and "article of manufacture" are used as synonyms.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

As used herein, the term "modulator" refers to a compound that alters an activity of a molecule. For example, a modulator can cause an increase or decrease in the magnitude of a certain activity of a molecule compared to the magnitude of the activity in the absence of the modulator. In certain embodiments, a modulator is an inhibitor, which decreases the magnitude of one or more activities of a molecule. In certain embodiments, an inhibitor completely prevents one or more activities of a molecule. In certain embodiments, a modulator is an activator, which increases the magnitude of at least one activity of a molecule. In certain embodiments the presence of a modulator results in an activity that does not occur in the absence of the modulator.

The term "non water-soluble diluent" represents compounds typically used in the formulation of pharmaceuticals, such as calcium phosphate, calcium sulfate, starches, modified starches and microcrystalline cellulose, and microcellulose (e.g., having a density of about 0.45 g/cm$^3$, e.g., Avicel, powdered cellulose), and talc.

By "pharmaceutically acceptable," as used herein, refers to a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "pharmaceutical combination" as used herein, means a product that results from the mixing or combining of more than one active ingredient and includes both fixed and non-fixed combinations of the active ingredients. The term "fixed combination" means that the active ingredients, e.g., the AM preparations and purified compositions described herein and a co-agent, are both administered to a patient simultaneously in the form of a single entity or dosage. The term "non-fixed combination" means that the active ingredients, e.g., the AM preparations and purified compositions described herein and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g., the administration of three or more active ingredients.

"Plasticizers" are compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. In some embodiments, plasticizers can also function as dispersing agents or wetting agents.

The term "polypeptide" or "protein" as used herein can be the full length polypeptide, or a fragment or segment of a polypeptide, and can encompass a stretch of amino acid residues of at least about 8 amino acids, generally at least 10 amino acids, more generally at least 20 amino acids, often at least 30 amino acids, more often at least 50 amino acids or more of the full length polypeptide.

"Solubilizers" include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

"Stabilizers" include compounds such as any antioxidation agents, buffers, acids, preservatives and the like.

"Substantially pure" or "purified" when used in the context of a biological material, amniotic material and/or a protein context typically means that the material is isolated from other contaminating proteins, nucleic acids, and other biologicals derived from the original source organism. Purity, or "isolation" may be assayed by standard methods, and will ordinarily be at least about 10% pure, more ordinarily at least about 20% pure, generally at least about 30% pure, and more generally at least about 40% pure; in further embodiments at least about 50% pure, or more often at least about 60% pure; in still other embodiments, at least about 95% pure.

"Suspending agents" include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

"Surfactants" include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants may be included to enhance physical stability or for other purposes.

As used herein, the term "subject" is used to mean an animal, preferably a mammal, including a human or non-human. The terms patient and subject may be used interchangeably.

The terms "treat," "treating" or "treatment," as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

"Wetting agents" include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 24D is a bar graph quantitating the cell migration that occurred in FIGS. 24A, 24B, and 24C.

DETAILED DESCRIPTION OF THE INVENTION

Compositions

Figures 1A, 1B:
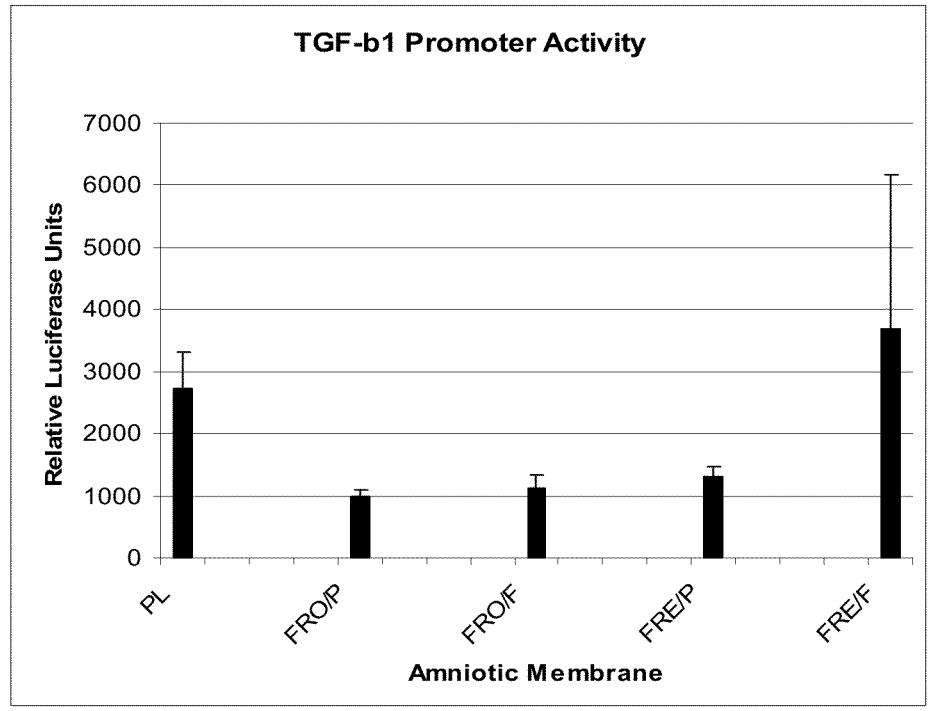
FIG. 1A is a non-limiting example of a bar graph showing the suppression of TGF-$\beta$1 promoter activity by various AM Extracts. PL: plastic control. FRO/P: frozen amniotic membrane, placental portion. FRO/F: frozen amniotic membrane, fetal portion. FRE/P: Fresh amniotic membrane, placental portion. FRE/F: Fresh amniotic membrane, fetal portion.
FIG. 1B is a table comparing the P values of the various placental preparations.

Described herein are purified compositions that exert a number of physiologically significant effects in mammalian cells and intact mammalian tissues. The purified compositions comprise at least four components:
Cross-linked high molecular weight hyaluronan (HA);
Tumor necrosis factor-stimulated gene 6 (TSG-6);
Pentraxin (PTX-3); and
Thrombospondin (TSP-1).

Additional components may also be included in purified compositions that have these four components, including: Smad7.

Any or all of the components of the purified compositions described herein can be prepared from a human amniotic material, including human amniotic jelly preparations and extracts (as described herein), human amniotic membrane preparations and extracts (as described herein), and human amniotic stroma preparations and extracts (as described herein).

Together, these four components (with or without Smad7) can suppress TGF β promoter activity; increase apoptosis in macrophages; decrease proliferation, decrease migration, and increase apoptosis of human vascular endothelial cells; decrease viability of human fibroblasts; decrease inflammation; and prevent apoptosis of epithelial cells exposed to storage and injury.

Hyaluronic acid (HA) is a natural sugar found in the synovial joint fluid, the vitreous humor of the eye, the cartilage, blood vessels, extra-cellular matrix, skin, and umbilical cord. The cross-linking of HA can be through a covalent bound to another molecule, such as a protein. For example, HA can be covalently bound to the heavy chain of inter-α-trypsin inhibitor. The ratio of protein to HA in the AM preparations and purified compositions described herein can be less than about 200:1, less than about 100:1, less than about 50:1, or less than about 10:1.

TSG-6 is a hyaluronan binding protein that plays a role in extracellular matrix remodeling, cell proliferation, and leucocyte migration. TSG-6 can form a complex with the serine protease inhibitor inter-α-inhibitor. PTX-3 (Pentraxins) are $Ca^{2+}$ dependent ligand binding proteins that have a pentameric discoid structure and are present in plasma. TSP-1 (Thrombospondin I) is a homotrimeric glycoprotein having a potent anti-angiogenic and other biological activities. TSP-1 is secreted into the extracellular matrix by a variety of cell types.

These components can be obtained from any suitable source. For example, at least one of the components can be obtained from human tissues, such as amniotic membrane, amniotic jelly, amniotic stroma, or a combination thereof. At least one of the components can be obtained from commercial sources. At least one of the components can be isolated from a transgenic organism. The protein sequences can have a similarity of at least 90%, 93%, 95%, 97%, 99% or 99.5% to the human protein sequence. The components can be purified, substantially purified, partially purified, or can also be present in crude extracts. The components can also be prepared from mammalian amniotic membrane tissues, as each of the four components is present in amniotic membrane tissues.

In additional aspects, the protein Smad7 is also present in the composition. The Smad7 can be obtained from any suitable source, such as from amniotic membrane, from a commercial source, isolated from a transgenic organism. The Smad7 protein can be purified, substantially purified, partially purified, or can be present in a crude extract.

AM Preparations Derived from Placental Material

In some aspects, at least one of the components HA, TSG-6, PTX-3, TSP-1, optionally Smad7 can be obtained from preparations of amniotic membrane. Alternatively, crude amniotic membrane preparations containing the combination of HA, TSG-6, PTX-3, TSP-1 and optionally Smad7 can be prepared. Exemplary methods of preparing various AM preparations are described herein.

Human placental material can be obtained, for example, from sources such as Bio-Tissue, Inc. (Miami, Fla.) and Baptist Hospital (Miami, Fla.) (under IRB approval). The tissue is typically obtained in either a fresh or frozen state. The tissue can be washed to remove excess storage buffer, blood, or contaminants. The excess liquid can be removed, for example, using a brief centrifugation step, or by other means. The tissue can be frozen, using, for example, liquid nitrogen or other cooling means, to facilitate the subsequent homogenization. The source of the AM tissue can be a human. However, other sources of AM tissue, such as bovine or porcine AM tissue, can be used.

The AM can be used to prepare the composition. AM preparations can include components or portions purified from or extracted from intact AM, AM stromal matrix, HA, AM jelly, and inter-alpha trypsin inhibitor (HA-ITI)). If desired, certain components of the AM preparation can be isolated from the preparation at any time during the process. For example, an extract enriched for a specific protein or set of AM proteins can be isolated from the preparation. After homogenization of the tissue, the larger particles can be separated out, or they can be left in the preparation. The preparation can be dried, if desired. An exemplary preparation method is described in Example 1.

The compositions can also be obtained from AM jelly. AM jelly can be obtained from the fresh AM tissue, or can be obtained before or after the freezing process. The AM jelly can be frozen, and can also be freeze-ground following the procedure for AM preparations as described herein. The jelly can be centrifuged, and can also be lyophilized.

In additional embodiments, a composition made substantially from the stromal layer is prepared. To prepare this composition, the stromal layer is separated from the layer of fresh, frozen, thawed, or otherwise treated AM membrane. The stromal removal can occur, for example, by enzymatic methods, mechanical methods, or by other means. The stromal layer material can be fresh or frozen. The stromal material can be ground or freeze-ground following the procedure for AM preparations as described herein. If desired, the stromal matrix material can be centrifuged, and can also be lyophilized.

The tissue can be frozen prior to the grinding process. The freezing step can occur by any suitable cooling process. For example, the tissue can be flash-frozen using liquid nitrogen. Alternatively, the material can be placed in an isopropanol/dry ice bath or can be flash-frozen in other coolants. Commercially available quick freezing processes can be used. Additionally, the material can be placed in a freezer and allowed to equilibrate to the storage temperature more slowly, rather than being flash-frozen. The tissue can be stored at any desired temperature. For example, −20° C. or −80° C. or other temperatures can be used for storage.

Pulverizing the tissue while frozen, rather than grinding the tissue prior to freezing, is one optional method for preparing the tissue. Alternatively, fresh, partially thawed, or thawed tissue can be used in the grinding step. The tissue (fresh, frozen, or thawed) can then be sliced into pieces of a desired size with a suitable device, such as a scalpel, then ground to fine particles using a BioPulverizer (Biospec Products, Inc., Bartlesville, Okla.) or other suitable devices, and homogenized with a homogenization device such as a Tissue Tearor (Biospec Products, Inc., Dremel, Wis., in a suitable solution. Exemplary solutions include but are not limited to phosphate buffered saline (PBS), DMEM, NaCl solution, and water. The pH of the solution can be adjusted as needed. In some embodiments, the pH range is from about 5.5 or 6.0 to about 8.5. In some embodiments, the frozen tissue is ground in a solution having a pH of between about 6.3, about 6.6, or about 7.0 to about 7.4, about 7.6, or about 7.8.

Any suitable buffer or liquid can be used to prepare the formulations. Example 2 examines the use of various extraction buffers (high salt, low salt, PBS, etc.) on total protein content and HA in the preparation (Table X). Example 2 further examines the levels of the specific proteins TSG-6 (FIG. 14), PTX-3 (FIG. 18), TSP-1 (FIG. 19), and Smad7 (FIG. 20) using several extraction methods.

The homogenate can then be mixed at any suitable speed, temperature, or other parameters. The mixing can occur, for example, at a temperature range of from about 1° C., or 3° C., to about 6° C., 10° C., 15° C., or 20° C. In some embodiments, the mixing occurs at about 4° C. The homogenate can be mixed, for example, from less than about 1 minute, 10 minutes, or 20 minutes to about 1, 2, 3 or more hours.

The homogenate can then be centrifuged to remove any remaining large particulates, if desired. The centrifugation can be performed using any suitable range of time, temperature, protein concentration, buffers, and speed as desired. The centrifugation can occur, for example, at a range of about 1,000, 5,000, or 10,000×g to about 20,000×g. In some embodiments, the centrifugation occurs at about 15,000×g. The centrifugation can occur for a duration of from less than 1 minute, 5 minutes, 10 minutes, 20 minutes, to about 40 minutes, 60 minutes, 1.5 hours, or more. The supernatant can then be collected and stored in aliquots at −80° C. The total protein can be quantitated, if desired, using any suitable commercial protein analysis kit, such as a BCA assay (Pierce, Rockford, Ill.). Example 2, Table X, and FIG. 13 describe the analysis of AM preparations after low speed or high speed centrifugation.

For biochemical characterization and purification, the above solutions can be supplemented with protease inhibitors. An exemplary mixture of protease inhibitors is the following: 1 µg/ml aprotinin, 1 µg/ml leupeptin, 1 µg/ml pepstatin A, and 1 mM PMSF. Typically, however, a protease inhibitor is not added to the preparation if it is to be added to live cells or tissues.

The formulation can be tested to confirm the presence of specific components or proteins. For example, the formulation can be tested for the presence of molecules including but not limited to HA, TSG-6, PTX-3, TSP-1, Smad7, and the like. The formulation can also be tested to confirm the absence of pathogens at any point during the preparation process.

AM preparations can be in a liquid, suspension, or lyophilized powder (e.g., ground or pulverized), or other forms. Antimicrobial agents such as antibiotics or anti-fungal agents may be added. Other substances can be added to the compositions to stabilize and/or preserve the compositions. The material can be packaged and stored, for example, at room temperature, or for example, at −20° C. or −80° C. prior to use.

In some embodiments, the preparation is present as a dry powder formulation. A dry powder formulation can be stored in a smaller volume, and may not require the same low temperature storage requirements to keep the formulation from degrading over time. A dry powder formulation can be stored and reconstituted prior to use. The dry powder formulation can be prepared, for example, by preparing the freeze-ground AM tissue as described herein, then removing at least a portion of the water in the composition. The excess water can be removed from the preparation by any suitable means. An exemplary method of removing the water is by use of lyophilization using a commercially available lyophilizer or freeze-dryer. Suitable equipment can be found, for example, through Virtis, Gardiner, N.Y.; FTS Systems, Stone Ridge, N.Y.; and SpeedVac (Savant Instruments Inc., Farmingdale, N.Y.). The amount of water that is removed can be from about 5%, 10%, 20%, 30% to about 60, 70, 80, 90, 95 or 99% or more. In some embodiments, substantially all of the excess water is removed. The lyophilized powder can then be stored. The storage temperature can vary from less than about −196° C.-80° C., −50° C., or −20° C. to more than about 23° C. If desired, the powder can be characterized (weight, protein content, etc) prior to storage.

The lyophilized powder can be reconstituted in a suitable solution or buffer prior to use. Exemplary solutions include but are not limited to PBS, DMEM, and BSS. The pH of the solution can be adjusted as needed. The concentration of the AM can be varied as needed. In some procedures a more concentrated preparation is useful, whereas in other procedures, a solution with a low concentration of AM is useful. Additional compounds can be added to the composition. Exemplary compounds that can be added to the reconstituted formulation include but are not limited to pH modifiers, buffers, collagen, HA, antibiotics, surfactants, stabilizers, proteins, and the like. The lyophilized AM powder can also be added to a prepared cream, ointment or lotion to result in the desired concentration.

Additional components can be added to the composition as desired. In some embodiments, water soluble or powdered AM preparations can be mixed with an ECM component such as collagen, fibrin, or HA.

Collagen is a major structural protein found in the body. It provides support for tissues, connects tissue to bone, and provides the structure of the body. When the body is in the healing process, collagen plays a role in helping to build a cellular structure. Hyaluronic acid is a natural sugar found in the synovial joint fluid, the vitreous humor of the eye, the cartilage, blood vessels, extra-cellular matrix, skin, and umbilical cord. Fibrin is a protein involved in the clotting of blood.

Water-soluble AM preparation can be mixed with collagen, fibrin or with HA. Similarly, lyophilized powder AM preparation can be mixed with collagen, fibrin or HA. Collagen, fibrin and HA can be are suitable delivery vehicles, as AM preparations mixed with collagen or HA were shown to exert a suppressive effect upon TGF β promoter activity. Although AM preparations were mixed with collagen gel and HA gel in the experiments described herein, any soluble forms (e.g., liquid) of collagen and HA or other ECM components (e.g., fibrin) can be used. The collagen, fibrin or HA can be derived from any suitable source organism. When collagen, fibrin or HA are added, the ratio of these compounds to AM can be varied as desired. For example, a ratio of AM to collagen (or fibrin or HA) of less than about 0.001:1, 0.01:1, 0.05:1, or 0.1:1, to about 1:1, 1.5:1, 2:1, 5:1, 10:1, 100:1 or 1000:1 or more can be used.

Collagen gel can be prepared, for example, by diluting the stock solution (4 mg/ml) with 0.1N acetic acid and by mixing it with appropriate volume ratios of 20×DMEM or suitable buffer, and 1 N NaOH, as described in Example 1. The collagen in the preparation can be present, for example, at a range of from less than about 2 mg/ml to more than about 4 mg/ml.

Various dilutions of high MW HA can be prepared, for example, by diluting commercially prepared HA (Healon™ (10 mg HA/ml) (Pharmacia, LaJolla, Calif.) in DMEM or suitable buffer. Lyophilized powder and water-soluble forms of AM preparations can be diluted in a solution such as PBS, DMEM, or other solutions into the desired collagen concentration. The HA in the preparation can be present, for example, at a range of from less than about 2 µg/ml to more than about 129 µg/ml.

The following procedures represent illustrative methods for preparing the amniotic preparations and purified compositions described and used herein.

Preparation of Preserved Human AM:

Human placenta was collected at elective cesarean delivery (Heiligenhaus et al., Invest Ophthalmol Vis Sci. 42:1969-1974, 2001, Lee and Tseng, Am J. Ophthalmol. 123:303-312, 1997, Prabhasawat et al., Ophthalmology, 104:974-985, 1997, Tseng et al., Arch Ophthalmol. 116:431-441, 1998). The AM was flattened onto nitrocellulose paper (Hybond N+, Amersham, England), with the epithelium surface up. The AM samples were stored at −80° C. in DMEM/glycerol 1:2 (v/v) until use.

Amniotic Membrane Extract Preparations

Fresh and frozen human placentas were obtained from Bio-Tissue, Bio-tissue, Inc. (Miami, Fla.). The entire procedure for preparation of total human AM extracts (AME) was carried out aseptically so as to be used for subsequent cell culture-based experiments. The AM was sliced into small pieces to fit into the barrel of a BioPulverizer (Biospec Products, Inc., Bartlesville, Okla.), frozen in the liquid nitrogen, pulverized into a fine powder, and weighed. Cold 1× PBS buffer, pH 7.4, containing protease inhibitors (protease inhibitor cocktail, P8340, Sigma, and supplemented with 1 mM PMSF) and phosphatase inhibitors (50 mM sodium fluoride and 0.2 mM sodium vanadate) was added to the powder at 1:1 (ml/g). The mixture was kept on ice and homogenized with a Tissue Tearor (Biospec Products, Inc., Dremel, Wis.) 5 times, 1 minute each, with a 2 minute cooling interval. These water-soluble extracts were designated as "Total" AM extracts (AME).

Total AM extracts were divided into two 50 ml conical centrifuge tubes. One was centrifuged at high speed (HS, 48,000×g) and the other one was centrifuged at a low speed (LS, 15,000×g) at 4° C. Aliquots of the HS and LS supernatant were transferred to sterile 1.5 ml Eppendorf tubes and were designated as AM/HS, AM/LS, respectively. Desired AM/HS samples were frozen at −20° C. for 1 h before lyophilization. The samples then were placed in the chamber of FreeZone (Labconco, Kansas City, Mo.) with holes on the cap. Samples were lyophilized at −50° C. at a vacuum of 0.85 mBar for 5 hours. Before use, the samples were reconstituted with the sterile distilled $H_2O$ to the same volume. The same method was also used to prepare extracts from AM jelly, which was easily scraped from the adherent material on the AM stroma.

Total Soluble Human Amniotic Membrane and Amniotic Membrane Jelly Extract Preparations Frozen human placenta material was obtained from Bio-Tissue, Bio-tissue, Inc. (Miami, Fla.). The entire procedure for preparation of total human AM extracts (AME) was carried out aseptically so as to be used for subsequent cell culture-based experiments. The AM was sliced into small pieces to fit into the barrel of a BioPulverizer (Biospec Products, Inc., Bartlesville, Okla.), frozen in the liquid nitrogen, pulverized into a fine powder, and weighed. Cold 1× PBS buffer, pH 7.4, containing protease inhibitors (protease inhibitor cocktail, P8340, Sigma, and supplemented with 1 mM PMSF) and phosphatase inhibitors (50 mM sodium fluoride and 0.2 mM sodium vanadate) was added to the powder at 1:1 (ml/g). The mixture was kept on ice and homogenized with a Tissue Tearor (Biospec Products, Inc., Dremel, Wis.) 5 times, 1 minute each, with a 2 minute cooling interval. These water-soluble extracts were designated as "Total" AM extracts (AME).

The total water-soluble extract was mixed for 1 hr at 4° C., subsequently fractionated by two different speeds of centrifugation at 4° C. for 30 min, i.e., 15000×g and 48000×g, and the resultant supernatant was designated as L and H, respectively. Each supernatant was divided into aliquots and stored at −80° C. This method was also used to prepare extracts from AM jelly, which was easily scraped from the adherent material on the AM stroma.

Total Soluble Human Amniotic Membrane and Amniotic Membrane Jelly Extracts by Different Buffers and Fractionation Methods In examining preparations in different extraction buffers, the powder as prepared from above was weighed and mixed with Buffer A (Isotonic Low salt): 100 mM Tris-HCl, pH 7.6, 150 mM NaCl, 4 mM EDTA, 1% Triton X-100 at the wet weight (g) of AM to the buffer (ml) at 1:1 ratio by stirring at 4° C. for 1 hr. After centrifugation at 48000×g, the resultant pellet was subsequently extracted by Buffer B (high salt): 100 mM Tris-HCl, pH 7.6, 1M NaCl, 4 mM EDTA, 1% Triton X-100 by stirring at 4° C. for 1 hr. Again after centrifugation at 48000×g, the pellet was finally extracted by Buffer C (4 M guanidine hydrochloride): 100 mM sodium acetate, pH 5.8, 4 M guanidine hydrochloride, 4 mM EDTA, 1% Triton X-100 by stirring at 4° C. for 24 hr. All the above three buffers were supplemented with the following protease and phosphatase inhibitors: 1 µg/ml aprotinin, 1 µg/ml leupeptins, 1 µg/ml pepstatin A, 0.5 mM PMSF, 50 µM sodium fluoride and 0.2 µM sodium vanadate. The resultant supernatants, designated as Extract A, B, and C, respectively, were dialyzed against the dialysis buffer (50 mM Tris-HCl, pH7.5, 0.15 M NaCl) supplemented with 0.5 mM PMSF at 4° C. for 6 hr and dialysis buffer was changed twice, each with 500× (the volume ratio-dialysis buffer:samples). After dialysis, the volume of each sample was measured and adjusted to the same volume with the dialysis buffer. The same method was also used to prepare extracts from AM jelly, which was the adherent material on the AM stroma that could be easily scraped off.

Preparation of Total Soluble Human Amniotic Membrane Extracts in PBS

The entire procedure for preparation of total soluble human AM extracts (T) was carried out aseptically so as to be used for subsequent cell culture-based experiments. Frozen human placenta was obtained from Bio-tissue, Inc. (Miami, Fla.), from which AM was retrieved. AM was sliced into small pieces to fit into the barrel of a BioPulverizer (Biospec Products, Inc., Bartlesville, Okla.), frozen in the liquid nitrogen, and then pulverized into a fine powder. The powder was weighed and mixed with cold PBS buffer (prepared by adding distilled $H_2O$ to 1×PBS, pH7.4, from 10 × PBS, cat#70011-044, Invitrogen, Carlsbad, Calif.) with protease inhibitors (protease inhibitor cocktail, P8340, Sigma, and supplemented with 1 mM PMSF) and phosphatase inhibitors (50 mM sodium fluoride and 0.2 mM sodium vanadate) at 1:1 (ml/g). The mixture was kept in the ice and homogenized with a Tissue Tearor (Biospec Products, Inc., Dremel, Wis.) for 5 times, 1 min each with a 2 min interval cooling. This water-soluble extract was designated as "Total" (T). The total water-soluble extract was mixed for 1 hr at 4° C., centrifuged at 4° C. for 30 min at 48000×g. The supernatant was divided into aliquots and stored at −80° C.

Preparation of Water-Soluble AM Stromal Extracts

Using aseptic techniques, frozen human AM obtained from Bio-Tissue, Inc. (Miami, Fla.) was briefly washed 2-3 times with HBSS to remove the original storage medium. The AM stroma was scraped by spatula, frozen in the air phase of liquid nitrogen and grounded to fine particles by BioPulverizer (Biospec Products, Inc., Bartlesville, Okla.) followed by homogenization on ice with Tissue Tearor (Biospec Products, Inc., Dremel, Wis.) in PBS, pH 7.4, for 1 min. The homogenate was mixed by rotation for 1 h and centrifuged at 14,000×g for 30 min at 4° C. The supernatant in PBS was then collected, and stored in aliquots at −80° C. The protein concentration was determined by BCA assay. This water-soluble protein extract, designated as amniotic stromal extract (ASE), was used for experiments described herein.

AM Stromal Extract Preparation

The complete procedure for preparation of protein extracts was carried out aspectically. Frozen human AM obtained from Bio-Tissue (Miami, Fla.) was briefly washed 2-3 times with HBSS (Invitrogen, Carlsbad, Calif.) to remove the storage medium. AM stroma was scraped from the stromal side of the AM by spatula for AM stroma extract preparation. Human placenta as well as chorion obtained from Baptist Hospital (Miami, Fla.) was rinsed 3 times with HBSS to remove blood. To prepare the water-soluble protein extract, total AM, scraped AM stroma, stroma-removed AM, placenta, and chorion were each frozen in the air phase of liquid nitrogen and each ground to fine particles using a BioPulverizer (Biospec Products, Inc., Bartlesville, Okla.) followed by homogenization on ice with Tissue Tearor (Biospec Products, Inc., Dremel, Wis.) in PBS (pH 7.4) for 1 min. Each homogenate was mixed for 1 hour and centrifuged at 14,000 g for 30 min at 40° C. Each supernatant (in PBS) was then collected and stored in aliquots (0.5 ml) at 80° C. A BCA assay (Pierce, Rockford, Ill.) was used to quantitate the total protein in different extracts.

Preparing Water-Soluble and Lyophilized Powder Forms of Human AM Extracts

In a typical procedure for preparing human AM extracts, the entire procedure is carried out aseptically. Unless otherwise noted, the AM extracts can be handled at room temperature during the steps of the procedure. First, fresh or frozen human AM is obtained, preferably from Bio-Tissue, Inc. (Miami, Fla.). Frozen AM is briefly washed 2-3 times with HBSS (Invitrogen, Carlsbad, Calif.) to remove the storage medium. Fresh human placenta or chorion is rinsed 3 times with HBSS to remove blood.

To prepare the water-soluble form of AM extracts, the AM (e.g., AM stroma, stroma-removed AM, placenta, chorion) is transferred to a sterile 50 ml centrifuge tube and centrifuged at 4° C. for 5 min at 5000×g to remove the excess fluid. The AM is weighed, transferred to a 100 mm or 150 mm sterile Petri dish, and frozen in the air phase of a liquid nitrogen container for 20 min to facilitate the subsequent homogenization. The frozen AM is then sliced into small pieces with a disposable scalpel or ground to fine particles using a BioPulverizer (Biospec Products, Inc., Bartlesville, Okla.) or other suitable device, and homogenized with Tissue Tearor (Biospec Products, Inc., Dremel, Wis.), or other suitable device, in phosphate buffered saline (PBS) or DMEM without phenol red (Invitrogen, Carlsbad, Calif.) at neutral pH. For biochemical characterization and purification, the above solutions are supplemented with the following proteinase inhibitors: 1 µg/ml aprotinin, 1 µg/ml leupeptin, 1 µg/ml pepstatin A, and 1 mM PMSF. However, if the extract is to be directly added to cell culture, no protease inhibitor is added. The homogenate is mixed at 4° C. for 30 min and centrifuged at 15,000×g for 30 min. The supernatant (i.e., AM extract) is collected and stored in aliquots (0.5 ml) at −80° C. A BCA assay (Pierce, Rockford, Ill.) is used to quantitate the total protein in each AM extract.

To prepare the lyophilized powder form of AM extracts, frozen AM is ground to fine particles using a BioPulverizer (Biospec Products, Inc., Bartlesville, Okla.), or other suitable device, and further homogenized as described herein. Aliquots of approximately 0.5 ml are lyophilized by SpeedVac (Savant Instruments Inc., Farmingdale, N.Y.) at 4° C. for 4 h to decrease the weight from 280 mg to 32 mg (~89% reduction). The lyophilized powder is weighed and stored at −80° C. Before use, the lyophilized powder can be reconstituted in a suitable buffer.

To prepare AM stromal extracts, the AM stroma is scraped from the stromal surface of intact total AM leaving the basement membrane and the amniotic epithelium intact, and the frozen AM stroma is ground using a BioPulverizer as described herein. The stroma is extracted with PBS (e.g., 1.4 mg/ml) at a neutral pH at 4° C. for 30 min and centrifuged at 15,000×g for 30 min. The supernatant is collected and stored in aliquots (0.5 ml) at −80° C. A BCA assay (Pierce, Rockford, Ill.) is used to quantitate the total protein in the AM stromal extract.

Methods involving conventional molecular biology techniques are described herein. Such techniques are generally known in the art and are described in detail in methodology treatises such as Molecular Cloning: A Laboratory Manual, 3$^{rd}$ ed., vol. 1-3, ed. Sambrook et al., Cold Spring Harbor Laboratory Press, Cold Spring Harbor, N.Y., 2001; and Current Protocols in Molecular Biology, ed. Ausubel et al., Greene Publishing and Wiley-Interscience, New York, 2003 (with periodic updates). Various techniques for culturing animal cells are known in the art and are described in Culture of Animal Cells: A Manual of Basic Technique, 4$^{th}$ ed., R. Ian Freshney, Wiley-Liss, Hoboken, N.J., 2000, and Animal Cell Culture Techniques (Springer Lab Manual), M. Clynos, Springer-Verlag, New York, N.Y., 1998. Methods involving protein analysis and purification are also known in the art and are described in Protein Analysis and Purification: Benchtop Techniques, 2$^{nd}$ ed., Ian M. Rosenberg, Birkhauser, New York, N.Y., 2004.

Pharmaceutical Compositions

AM preparations can be formulated for administration purposes as a non-solid dosage form, for example, by combining with a delivery vehicle to create compositions such as solutions, drops, suspensions, pastes, sprays, ointments, oils, emulsions, aerosols, a coated bandage, a patch, creams, lotions, gels, and the like. The formulation used will depend upon the particular application. Gels are useful for administering the compositions because they allow better retention of the active ingredient at the site of introduction, allowing the active ingredient to exert its effect for a longer period of time before clearance of the active ingredient. Alternatively, AM preparations can be formulated as extended-release solid dosage forms (including oral dosage forms). A description of exemplary pharmaceutically acceptable carriers or vehicles and diluents, as well as pharmaceutical formulations, is provided herein and can also be found in Remington's Pharmaceutical Sciences, a standard text in this field, and in USP/NF.

Pharmaceutical compositions may be formulated in a conventional manner using one or more physiologically acceptable carriers including excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art. A summary of pharmaceutical compositions described herein may be found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins; 1999), herein incorporated by reference in their entirety.

In certain embodiments, the compositions include a pharmaceutically acceptable diluent(s), excipient(s), or carrier(s). In addition, the AM preparations and purified compositions described herein can be administered as pharmaceutical compositions in which AM preparations and purified compositions described herein are mixed with other active ingredients, as in combination therapy. In some embodiments, the pharmaceutical compositions may include other medicinal or pharmaceutical agents, carriers, adjuvants, such as preserving, stabilizing, wetting or emulsifying agents, solution promoters, salts for regulating the osmotic pressure, and/or buffers. In addition, the pharmaceutical compositions can also contain other therapeutically valuable substances.

A pharmaceutical composition, as used herein, refers to a mixture of a AM preparations and purified compositions described herein with other chemical components, such as carriers, stabilizers, diluents, dispersing agents, suspending agents, thickening agents, and/or excipients. The pharmaceutical composition facilitates administration of the compound to an organism. In practicing the methods of treatment or use provided herein, therapeutically effective amounts of AM preparations and purified compositions described herein are administered in a pharmaceutical composition to a mammal having a disease, disorder, or condition to be treated. In some embodiments, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

Topical Formulations

Formulations of the AM preparations and purified compositions described herein include those suitable for topical administration. The formulations may conveniently be presented in unit dosage form and may be prepared by any methods well known in the art of pharmacy. The amount of active ingredients which can be combined with a carrier material to produce a single dosage form will vary depending upon the host being treated, the particular mode of administration.

Suspensions may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Typical compositions described herein include a wide variety of physical forms. These include, but are not limited to, solutions, lotions, creams, oils, gels, sticks, sprays, ointments, balms, shampoo, and pastes. Generally, such carrier systems can be described as being solutions, emulsions, gels, solids, and aerosols. The compositions may be applied topically to the skin, or may be applied in the form of a transdermal delivery device, such as a microneedle, a patch, bandage, or gauze pad known in the art.

The ointments, pastes, creams and gels may contain, in addition to the AM preparations and purified compositions described herein, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the AM preparations and purified compositions described herein, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Solvents are generally employed in the preparation of suitable topical compositions. Such solvents can either be aqueous or organic based. The solvent must be capable of having dispersed or dissolved therein the active ingredients while not being irritating to the animal being treated. Water forms the basis for all aqueous solvents, while suitable organic solvents include propylene glycol, butylene glycol, polyethylene glycol, polypropylene glycol, glycerol, 1,2,4-butanetriol, sorbitol esters, 1,2,6-hexanetriol, ethanol, isopropanol, butanediol, and mixtures thereof. Solvents can be included in the overall composition in amounts ranging from 0.1% to 99% and preferably from 2.0% to 75%. In some embodiments, the compositions are produced in the form of an emollient-containing composition. A wide variety of suitable emollients are known and may be used herein.

In some embodiments, the compositions are formulated as lotions containing from about 0.01% to 10% of the AM preparations and purified compositions described herein. In other embodiments, the compositions are formulated in a solution carrier system as a cream. A cream composition would preferably comprise from about 0.1% to 15% and preferably from 1% to 5% of the AM preparations and purified compositions described herein. Lotions and creams can be formulated as emulsions as well as solutions. The compositions may also be administered in liquid form, including in the form of liposomes suspended in liquid, as in the different type of sprays available in this industry.

In other embodiments, the active ingredients are formulated as ointments. Suitable ointments may comprise simple bases of animal or vegetable oils, or semi-solid hydrocarbons (oleaginous). Suitable ointments may also comprise absorption ointment bases which absorb water to form emulsions. Ointment carriers may also be water soluble. An ointment may comprise from 1% to 99% of an emollient plus to about 0.1% to 99% of a thickening agent.

The proportion of the AM preparations and purified compositions described herein in the compositions can vary from between about 0.01 wt. % to about 100 wt. %, more preferably from about 0.1 wt. % to about 99.9 wt. %, and especially from about 1.0 wt. % to about 99.0 wt. %.

"Carriers" or "vehicles" preferably refer to carrier materials suitable for topical administration and include any such materials known in the art, such as any liquid, gel solvent, liquid diluent, solubilizer, or the like, which is non-toxic, and which does not interact with other components of the composition in a deleterious manner. Examples of suitable carriers for use herein include water, silicone, liquid sugars, waxes, oils, petroleum jelly, and a variety of other materials.

In some embodiments, the carrier or vehicle includes one or more solvents, oils, surfactants, humectants, thickening agents, antioxidants, chelating agents, buffers, and preservatives.

Examples of solvents include $C_2$-$C_{10}$ alcohols, such as hexanol, cyclohexanol, benzyl alcohol, 1,2-butanediol, glycerol, and amyl alcohol; $C_5$-$C_{10}$ hydrocarbons such as n-hexane, cyclohexane, and ethylbenzene; $C_4$-$C_{10}$ aldehydes and ketones, such as heptylaldehyde, cyclohexanone, and benzylaldehyde; $C_4$-$C_{10}$ esters, such as amyl acetate and benzyl propionate; ethereal oils, such as oil of eucalyptus, oil of rue, cumin oil, limonene, thymol, and 1-pinene; halogenated hydrocarbons having 2-8 carbon atoms, such as 1-chlorohexane, 1-bromohexane, and chlorocyclohexane.

Examples of oils comprise fats and oils such as olive oil and hydrogenated oils; waxes such as beeswax and lanolin; hydrocarbons such as liquid paraffin, ceresin, and squalane; fatty acids such as stearic acid and oleic acid; alcohols such as cetyl alcohol, stearyl alcohol, lanolin alcohol, and hexadecanol; and esters such as isopropyl myristate, isopropyl palmitate and butyl stearate.

Examples of surfactants include anionic surfactants such as sodium stearate, sodium cetyl sulfate, polyoxyethylene laurylether phosphate, sodium N-acyl glutamate; cationic surfactants such as stearyldimethylbenzylammonium chloride and stearyltrimethylammonium chloride; ampholytic surfactants such as alkylaminoethylglycine hydrochloride solutions and lecithin; and nonionic surfactants such as glycerin monostearate, sorbitan monostearate, sucrose fatty acid esters, propylene glycol monostearate, polyoxyethylene oleylether, polyethylene glycol monostearate, polyoxyethylene sorbitan monopalmitate, polyoxyethylene coconut fatty acid monoethanolamide, polyoxypropylene glycol (e.g., the materials sold under the trademark "Pluronic"), polyoxyethylene castor oil, and polyoxyethylene lanolin.

Examples of humectants include glycerin, 1,3-butylene glycol, and propylene glycol; examples of thickening agents include xanthan gum, hydroxypropyl cellulose, hydroxypropyl methyl cellulose, polyethylene glycol and sodium carboxymethyl cellulose; examples of antioxidants comprise butylated hydroxytoluene, butylated hydroxyanisole, propyl gallate, citric acid and ethoxyquin; examples of chelating agents include disodium edetate and ethanehydroxy diphosphate; examples of buffers comprise citric acid, sodium citrate, boric acid, borax, and disodium hydrogen phosphate; and examples of preservatives are methyl parahydroxybenzoate, ethyl parahydroxybenzoate, dehydroacetic acid, salicylic acid and benzoic acid.

In certain embodiments, the carrier/vehicle is composed of the foregoing materials to achieve a controlled occlusion of the skin, thereby resulting in optimal enhancement of biologically active moiety penetration across the skin with minimal skin irritation. In certain embodiments, the carrier/vehicle may include a dispersing agent that aids in maintaining a particulate phase of the active ingredients dispersed in the continuous phase. In other embodiments, non-ionic excipients, such as lauric alcohol, propylene glycol monolaurate, myristyl lactate, lauryl lactate, or the like, facilitate dispersion.

The rate of biologically active moiety delivery across a dermal surface can be increased by transdermal delivery enhancers. Suitable transdermal delivery enhancers include proton-accepting solvents such as dimethylsulfoxide and dimethylacetamide. Other suitable transdermal delivery enhancers include 2-pyrrolidine, N,N-diethyl-m-toluamide, 1-dodecylazacycloheptan-2-one, N,N-dimethylformamide, N-methyl-2-pyrrolidine, terpenes, surfactants, and calcium thioglycolate.

Suitable dermal penetration enhancers include 1-5 carbon fatty acid esters of para-aminobenzoic acid, isopropyl palmitate, isopropyl myristate, ethanol, isobutyl alcohol, isobutyl alcohol, stearyl alcohol, glycerol, 2-pyrrolidone, urea, propylene glycol, oleic acid, palmitic acid, dimethyl sulfoxide, N,N-dimethyl acetamide, N,N-dimethyl formamide, 2-pyrrolidone, 1-methyl-2-pyrrolidone, 5-methyl-2-pyrrolidone, 1,5-dimethyl-2-pyrrolidone, 1-ethyl-2-pyrrolidone, 2-pyrrolidone-5-carboxylic acid, N,N-dimethyl-m-toluamide, urea, ethyl acetate, 1-dodecylazacycloheptan-2-one, oleic acid, imidazoline, butylurea, and pyrrolidone carboxylic acid esters.

Wetting agents, emulsifiers, surfactants, and lubricants, such as sodium lauryl sulfate and magnesium stearate, as well as coloring agents, release agents, coating agents, sweetening, flavoring, and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

As appropriate compositions for topical application there may be cited all compositions usually employed for topically administering therapeutics, e.g., creams, jellies, dressings, shampoos, tinctures, pastes, ointments, salves, powders, liquid or semiliquid formulations, and the like. Application of said compositions may be by aerosol, e.g., with a propellant such as nitrogen carbon dioxide, a freon, or without a propellant such as a pump spray, drops, lotions, or a semisolid such as a thickened composition which can be applied by a swab. In particular compositions, semisolid compositions such as salves, creams, pastes, jellies, ointments, and the like will conveniently be used.

Ophthalmic Formulations

The AM preparations and purified compositions described herein can be administered in a variety of ways, including all forms of local delivery to the eye. Additionally, the AM preparations and purified compositions described herein can be administered systemically, such as orally or intravenously. The AM preparations and purified compositions described herein can be administered topically to the eye and can be formulated into a variety of topically administrable ophthalmic compositions, such as solutions, suspensions, gels or ointments. Thus, "ophthalmic administration" encompasses, but is not limited to, intraocular injection, subretinal injection, intravitreal injection, periocular administration, subconjuctival injections, retrobulbar injections, intracameral injections (including into the anterior or vitreous chamber), sub-Tenon's injections or implants, ophthalmic solutions, ophthalmic suspensions, ophthalmic ointments, ocular implants and ocular inserts, intraocular solutions, use of iontophoresis, incorporation in surgical irrigating solutions, and packs (by way of example only, a saturated cotton pledget inserted in the fornix).

A composition comprising the AM preparations and purified compositions described herein can illustratively take the form of a liquid where the agents are present in solution, in suspension or both. Typically when the composition is administered as a solution or suspension a first portion of the agent is present in solution and a second portion of the agent is present in particulate form, in suspension in a liquid matrix. In some embodiments, a liquid composition may include a gel formulation. In other embodiments, the liquid composition is aqueous. Alternatively, the composition can take the form of an ointment.

Useful compositions can be an aqueous solution, suspension or solution/suspension, which can be presented in the form of eye drops. A desired dosage can be administered via a known number of drops into the eye. For example, for a drop volume of 25 µl, administration of 1-6 drops will deliver 25-150 µl of the composition. Aqueous compositions typically contain from about 0.01% to about 50%, more typically about 0.1% to about 20%, still more typically about 0.2% to about 10%, and most typically about 0.5% to about 5%, weight/volume of the AM preparations and purified compositions described herein.

Typically, aqueous compositions have ophthalmically acceptable pH and osmolality. "Ophthalmically acceptable" with respect to a formulation, composition or ingredient typically means having no persistent detrimental effect on the treated eye or the functioning thereof, or on the general health of the subject being treated. Transient effects such as minor irritation or a "stinging" sensation are common with topical ophthalmic administration of agents and consistent with the formulation, composition or ingredient in question being "ophthalmically acceptable."

Useful aqueous suspension can also contain one or more polymers as suspending agents. Useful polymers include water-soluble polymers such as cellulosic polymers, e.g., hydroxypropyl methylcellulose, and water-insoluble polymers such as cross-linked carboxyl-containing polymers. Useful compositions can also comprise an ophthalmically acceptable mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

Useful compositions may also include ophthalmically acceptable solubilizing agents to aid in the solubility of components of the AM preparations and purified compositions described herein. The term "solubilizing agent" generally includes agents that result in formation of a micellar solution or a true solution of the agent. Certain ophthalmically acceptable nonionic surfactants, for example polysorbate 80, can be useful as solubilizing agents, as can ophthalmically acceptable glycols, polyglycols, e.g., polyethylene glycol 400, and glycol ethers.

Useful compositions may also include one or more ophthalmically acceptable pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an ophthalmically acceptable range.

Useful compositions may also include one or more ophthalmically acceptable salts in an amount required to bring osmolality of the composition into an ophthalmically acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other useful compositions may also include one or more ophthalmically acceptable preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other useful compositions may include one or more ophthalmically acceptable surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other useful compositions may include one or more antioxidants to enhance chemical stability where required. Suitable antioxidants include, by way of example only, ascorbic acid and sodium metabisulfite.

Aqueous suspension compositions can be packaged in single-dose non-reclosable containers. Alternatively, multiple-dose reclosable containers can be used, in which case it is typical to include a preservative in the composition.

The ophthalmic composition may also take the form of a solid article that can be inserted between the eye and eyelid or in the conjunctival sac, where it releases the AM preparations and purified compositions described herein. Release is to the lacrimal fluid that bathes the surface of the cornea, or directly to the cornea itself, with which the solid article is generally in intimate contact. Solid articles suitable for implantation in the eye in such fashion are generally composed primarily of polymers and can be biodegradable or non-biodegradable.

Injectable Formulations

Formulations suitable for intramuscular, subcutaneous, or intravenous injection may include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants. Formulations suitable for subcutaneous injection may also contain additives such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

For intravenous injections, AM preparations and purified compositions described herein may be formulated in aqueous solutions, in physiologically compatible buffers such as Hank's solution, Ringer's solution, physiological saline buffer, or other suitable solutions. For transmucosal administration, penetrants appropriate to the barrier to be permeated are used in the formulation. Such penetrants are generally known in the art. For other parenteral injections, appropriate formulations may include aqueous or nonaqueous solutions, preferably with physiologically compatible buffers or excipients. Such excipients are generally known in the art.

Parenteral injections may involve bolus injection or continuous infusion. Formulations for injection may be presented in unit dosage form, e.g., in ampoules or in multi dose containers, with an added preservative. The pharmaceutical composition described herein may be in a form suitable for parenteral injection as a sterile suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

Transdermal Formulations

Transdermal formulations described herein may be administered using a variety of devices which have been described in the art. For example, such devices include, but are not limited to, U.S. Pat. Nos. 3,598,122, 3,598,123, 3,710,795, 3,731,683, 3,742,951, 3,814,097, 3,921,636, 3,972,995, 3,993,072, 3,993,073, 3,996,934, 4,031,894, 4,060,084, 4,069,307, 4,077,407, 4,201,211, 4,230,105, 4,292,299, 4,292,303, 5,336,168, 5,665,378, 5,837,280, 5,869,090, 6,923,983, 6,929,801 and 6,946,144, each of which is specifically incorporated by reference in its entirety.

The transdermal dosage forms described herein may incorporate certain pharmaceutically acceptable excipients which are conventional in the art. In one embodiments, the transdermal formulations described herein include at least three components: (1) a formulation as described herein; (2) a penetration enhancer; and (3) an aqueous adjuvant. In addition, transdermal formulations can include additional components such as, but not limited to, gelling agents, creams and ointment bases, and the like. In some embodiments, the transdermal formulation can further include a woven or non-woven backing material to enhance absorption and prevent the removal of the transdermal formulation from the skin. In other embodiments, the transdermal formulations described herein can maintain a saturated or supersaturated state to promote diffusion into the skin.

Formulations suitable for transdermal administration of AM preparations and purified compositions described herein may employ transdermal delivery devices and transdermal delivery patches and can be lipophilic emulsions or buffered, aqueous solutions, dissolved and/or dispersed in a polymer or an adhesive. Such patches may be constructed for continuous, pulsatile, or on demand delivery of pharmaceutical agents. Still further, transdermal delivery of the AM preparations and purified compositions described herein can be accomplished by means of iontophoretic patches and the like. Additionally, transdermal patches can provide controlled delivery of the composition. The rate of absorption can be slowed by using rate-controlling membranes or by trapping the compound within a polymer matrix or gel. Conversely, absorption enhancers can be used to increase absorption. An absorption enhancer or carrier can include absorbable pharmaceutically acceptable solvents to assist passage through the skin. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

Solid Oral Dosage Forms

The pharmaceutical solid dosage forms described herein can include one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other aspects, using standard coating procedures, such as those described in *Remington's Pharmaceutical Sciences,* 20th Edition (2000).

Compressed tablets are solid dosage forms prepared by compacting the bulk blend of the formulations described herein. In various embodiments, compressed tablets which are designed to dissolve in the mouth will include one or more flavoring agents. In other embodiments, the compressed tablets will include a film surrounding the final compressed tablet. In some embodiments, the film coating can provide a delayed release of the composition from the formulation. In other embodiments, the film coating aids in patient compliance (e.g., Opadry® coatings or sugar coating). Film coatings including Opadry® typically range from about 1% to about 3% of the tablet weight. In other embodiments, the compressed tablets include one or more excipients.

A capsule may be prepared, for example, by placing the bulk blend of the formulation of the composition described herein, inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule may be swallowed whole or the capsule may be opened and the contents sprinkled on food prior to eating. In some embodiments, the therapeutic dose is split into multiple (e.g., two, three, or four) capsules. In some embodiments, the entire dose of the formulation is delivered in a capsule form.

In various embodiments, the particles of the composition and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In another aspect, dosage forms may include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

The pharmaceutical solid dosage forms including AM preparations and purified compositions described herein can be further formulated to provide a controlled release of the composition. Controlled release refers to the release of the composition from a dosage form in which it is incorporated according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. Such release rates can provide therapeutically effective levels of agent for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

In some embodiments, the solid dosage forms described herein can be formulated as enteric coated delayed release oral dosage forms, i.e., as an oral dosage form of a pharmaceutical composition as described herein which utilizes an enteric coating to affect release in the small intestine of the gastrointestinal tract. The enteric coated dosage form may be a compressed or molded or extruded tablet/mold (coated or uncoated) containing granules, powder, pellets, beads or particles of the active ingredient and/or other composition components, which are themselves coated or uncoated. The enteric coated oral dosage form may also be a capsule (coated or uncoated) containing pellets, beads or granules of the solid carrier or the composition, which are themselves coated or uncoated.

In other embodiments, the formulations described herein are delivered using a pulsatile dosage form. A pulsatile dosage form is capable of providing one or more immediate release pulses at predetermined time points after a controlled lag time or at specific sites. Pulsatile dosage forms may be administered using a variety of pulsatile formulations known in the art. For example, such formulations include, but are not limited to, those described in U.S. Pat. Nos. 5,011,692, 5,017,381, 5,229,135, and 5,840,329, each of which is specifically incorporated by reference. Other pulsatile release dosage forms suitable for use with the present formulations include, but are not limited to, for example, U.S. Pat. Nos. 4,871,549, 5,260,068, 5,260,069, 5,508,040, 5,567,441 and 5,837,284, all of which are specifically incorporated by reference.

Many other types of controlled release systems known to those of ordinary skill in the art and are suitable for use with the formulations described herein. Examples of such delivery systems include, e.g., polymer-based systems, such as polylactic and polyglycolic acid, plyanhydrides and polycaprolactone; porous matrices, nonpolymer-based systems that are lipids, including sterols, such as cholesterol, cholesterol esters and fatty acids, or neutral fats, such as mono-, di- and triglycerides; hydrogel release systems; silastic systems; peptide-based systems; wax coatings, bioerodible dosage forms, compressed tablets using conventional binders and the like. See, e.g., Liberman et al., *Pharmaceutical Dosage Forms*, 2 Ed., Vol. 1, pp. 209-214 (1990); Singh et al., *Encyclopedia of Pharmaceutical Technology*, $2^{nd}$ Ed., pp. 751-753 (2002); U.S. Pat. Nos. 4,327,725, 4,624,848, 4,968,509, 5,461,140, 5,456,923, 5,516,527, 5,622,721, 5,686,105, 5,700,410, 5,977,175, 6,465,014 and 6,932,983, each of which is specifically incorporated by reference.

In some embodiments, pharmaceutical formulations are provided that include particles of the compositions described herein and at least one dispersing agent or suspending agent for administration to a subject. The formulations may be a powder and/or granules for suspension, and upon admixture with water, a substantially uniform suspension is obtained.

The aqueous suspensions and dispersions described herein can remain in a homogenous state, as defined in The USP Pharmacists' Pharmacopeia (2005 edition, chapter 905), for at least 4 hours. The homogeneity should be determined by a sampling method consistent with regard to determining homogeneity of the entire composition. In one embodiment, an aqueous suspension can be re-suspended into a homogenous suspension by physical agitation lasting less than 1 minute. In another embodiment, an aqueous suspension can be re-suspended into a homogenous suspension by physical agitation lasting less than 45 seconds. In yet another embodiment, an aqueous suspension can be re-suspended into a homogenous suspension by physical agitation lasting less than 30 seconds. In still another embodiment, no agitation is necessary to maintain a homogeneous aqueous dispersion.

Suitable viscosity enhancing agents for the aqueous suspensions or dispersions described herein include, but are not limited to, methyl cellulose, xanthan gum, carboxymethyl cellulose, hydroxypropyl cellulose, hydroxypropylmethyl cellulose, Plasdon® S-630, carbomer, polyvinyl alcohol, alginates, acacia, chitosans and combinations thereof. The concentration of the viscosity enhancing agent will depend upon the agent selected and the viscosity desired.

In addition to the additives listed above, the liquid formulations can also include inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, sodium lauryl sulfate, sodium doccusate, cholesterol, cholesterol esters, taurocholic acid, phosphotidylcholine, oils, such as cottonseed oil, groundnut oil, corn germ oil, olive oil, castor oil, and sesame oil, glycerol, tetrahydrofurfuryl alcohol, polyethylene glycols, fatty acid esters of sorbitan, or mixtures of these substances, and the like.

It is to be appreciated that there is overlap between the above-listed additives used in the aqueous dispersions or suspensions described herein, since a given additive is often classified differently by different practitioners in the field, or is commonly used for any of several different functions. Thus, the above-listed additives should be taken as merely exemplary, and not limiting, of the types of additives that can be included in formulations described herein. The amounts of such additives can be readily determined by one skilled in the art, according to the particular properties desired.

Intranasal Formulations

Intranasal formulations are known in the art and are described in, for example, U.S. Pat. Nos. 4,476,116, 5,116,817 and 6,391,452, each of which is specifically incorporated by reference. Formulations can be prepared according to these and other techniques well-known in the art are prepared as solutions in saline, employing benzyl alcohol or other suitable preservatives, fluorocarbons, and/or other solubilizing or dispersing agents known in the art. See, for example, Ansel, H. C. et al., Pharmaceutical Dosage Forms and Drug Delivery Systems, Sixth Ed. (1995). These compositions and formulations can be prepared with suitable nontoxic pharmaceutically acceptable ingredients. These ingredients are known to those skilled in the preparation of nasal dosage forms and some of these can be found in REMINGTON: THE SCIENCE AND PRACTICE OF PHARMACY, 21st edition, 2005, a standard reference in the field. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents may also be present.

For administration by inhalation, the compositions described herein may be in a form as an aerosol, a mist or a powder. Pharmaceutical compositions described herein are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, such as, by way of example only, gelatin for use in an inhaler or insufflator may be formulated containing a powder mix of the AM preparations and purified compositions described herein and a suitable powder base such as lactose or starch.

Other Formulations

The AM preparations and purified compositions described herein may also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

Methods of Dosing and Treatment Regimens

The compositions can be administered by any suitable technique. Typically, the compositions will be administered directly to a target site (e.g., ocular surface, skin). The administration of formulations to the ocular surface is well known in the art. If delivery of AM preparations to the skin is desired, topical administration can be used. An injectable composition is also envisioned. Administration can also be parenteral (e.g., subcutaneous). Other methods of delivery, e.g., liposomal delivery, diffusion from a device impregnated with the composition, and microemulsion-based transdermal delivery in both cosmetic and pharmaceutical applications, are known in the art.

The compositions containing the AM preparations and purified compositions described herein can be administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician. It is considered well within the skill of the art for one to determine such therapeutically effective amounts by routine experimentation (including, but not limited to, a dose escalation clinical trial).

In prophylactic applications, compositions containing the AM preparations and purified compositions described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. It is considered well within the skill of the art for one to determine such prophylactically effective amounts by routine experimentation (e.g., a dose escalation clinical trial). When used in a patient, effective amounts for this use will depend on the severity and course of the disease, disorder or condition, previous therapy, the patient's health status and response to the drugs, and the judgment of the treating physician.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the compounds may be given continuously; alternatively, the dose of drug being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday may be from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

The amount of a given agent that will correspond to such an amount will vary depending upon factors such as the particular compound, disease or condition and its severity, the identity (e.g., weight) of the subject or host in need of treatment, but can nevertheless be routinely determined in a manner known in the art according to the particular circumstances surrounding the case, including, e.g., the specific agent being administered, the route of administration, the condition being treated, and the subject or host being treated. In general, however, doses employed for adult human treatment will typically be in the range of 0.02-5000 mg per day, preferably 1-1500 mg per day. The desired dose may conveniently be presented in a single dose or as divided doses administered simultaneously (or over a short period of time) or at appropriate intervals, for example as two, three, four or more sub-doses per day.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi dose containers, with an added preservative.

The daily dosages appropriate for the AM preparations and purified compositions described herein are from about 0.01 to 2.5 mg/kg per body weight. An indicated daily dosage in the larger mammal, including, but not limited to, humans, is in the range from about 0.5 mg to about 100 mg, conveniently administered in divided doses, including, but not limited to, up to four times a day or in extended release form. Suitable unit dosage forms for oral administration include from about 1 to 50 mg active ingredient. The foregoing ranges are merely suggestive, as the number of variables in regard to an individual treatment regime is large, and considerable excursions from these recommended values are not uncommon. Such dosages may be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

Combination Treatments

The compositions and methods described herein may also be used in conjunction with other well known therapeutic reagents that are selected for their particular usefulness against the condition that is being treated. In general, the compositions described herein and, in embodiments where combinational therapy is employed, other agents do not have to be administered in the same pharmaceutical composition, and may, because of different physical and chemical characteristics, have to be administered by different routes. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The particular choice of compounds used will depend upon the diagnosis of the attending physicians and their judgment of the condition of the patient and the appropriate treatment protocol. The compounds may be administered concurrently (e.g., simultaneously, essentially simultaneously or within the same treatment protocol) or sequentially, depending upon the nature of the disease, disorder, or condition, the condition of the patient, and the actual choice of compounds used. The determination of the order of administration, and the number of repetitions of administration of each therapeutic agent during a treatment protocol, is well within the knowledge of the skilled physician after evaluation of the disease being treated and the condition of the patient.

It is known to those of skill in the art that therapeutically-effective dosages can vary when the drugs are used in treatment combinations. Methods for experimentally determining therapeutically-effective dosages of drugs and other agents for use in combination treatment regimens are described in the literature. For example, the use of metronomic dosing, i.e., providing more frequent, lower doses in order to minimize toxic side effects, has been described extensively in the literature. Combination treatment further includes periodic treatments that start and stop at various times to assist with the clinical management of the patient.

For combination therapies described herein, dosages of the co-administered compounds will of course vary depending on the type of co-drug employed, on the specific drug employed, on the disease or condition being treated and so forth. In addition, when co-administered with one or more biologically active agents, the compound provided herein may be administered either simultaneously with the biologically active agent(s), or sequentially. If administered sequentially, the attending physician will decide on the appropriate sequence of administering protein in combination with the biologically active agent(s).

In any case, the multiple therapeutic agents may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents; the use of multiple therapeutic combinations are also envisioned.

It is understood that the dosage regimen to treat, prevent, or ameliorate the condition(s) for which relief is sought, can be modified in accordance with a variety of factors. These factors include the disorder from which the subject suffers, as well as the age, weight, sex, diet, and medical condition of the subject. Thus, the dosage regimen actually employed can vary widely and therefore can deviate from the dosage regimens set forth herein.

The pharmaceutical agents which make up the combination therapy disclosed herein may be a combined dosage form or in separate dosage forms intended for substantially simultaneous administration. The pharmaceutical agents that make up the combination therapy may also be administered sequentially, with either therapeutic compound being administered by a regimen calling for two-step administration. The two-step administration regimen may call for sequential administration of the active agents or spaced-apart administration of the separate active agents. The time period between the multiple administration steps may range from, a few minutes to several hours, depending upon the properties of each pharmaceutical agent, such as potency, solubility, bioavailability, plasma half-life and kinetic profile of the pharmaceutical agent. Circadian variation of the target molecule concentration may also determine the optimal dose interval.

In addition, the AM preparations and purified compositions described herein also may be used in combination with procedures that may provide additional or synergistic benefit to the patient. By way of example only, patients are expected to find therapeutic and/or prophylactic benefit in the methods described herein, wherein pharmaceutical composition of a compound disclosed herein and/or combinations with other therapeutics are combined with genetic testing to determine whether that individual is a carrier of a mutant gene that is known to be correlated with certain diseases or conditions.

The AM preparations and purified compositions described herein and combination therapies can be administered before, during or after the occurrence of a disease or condition, and the timing of administering the composition containing a compound can vary. Thus, for example, the compounds can be used as a prophylactic and can be administered continuously to subjects with a propensity to develop conditions or diseases in order to prevent the occurrence of the disease or condition. The compounds and compositions can be administered to a subject during or as soon as possible after the onset of the symptoms. The administration of the compounds can be initiated within the first 48 hours of the onset of the symptoms, preferably within the first 48 hours of the onset of the symptoms, more preferably within the first 6 hours of the onset of the symptoms, and most preferably within 3 hours of the onset of the symptoms. The initial administration can be via any route practical, such as, for example, an intravenous injection, a bolus injection, infusion over 5 minutes to about 5 hours, a pill, a capsule, transdermal patch, buccal delivery, and the like, or combination thereof. A compound is preferably administered as soon as is practicable after the onset of a disease or condition is detected or suspected, and for a length of time necessary for the treatment of the disease, such as, for example, from about 1 month to about 3 months. The length of treatment can vary for each subject, and the length can be determined using the known criteria. For example, the compound or a formulation containing the compound can be administered for at least 2 weeks, preferably about 1 month to about 5 years, and more preferably from about 1 month to about 3 years.

Kits/Articles of Manufacture

For use in the therapeutic applications described herein, kits and articles of manufacture are also described herein. Such kits can include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. The containers can be formed from a variety of materials such as glass or plastic.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease, disorder, or condition.

For example, the container(s) can include one or more AM preparations and purified compositions described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprising a compound with an identifying description or label or instructions relating to its use in the methods described herein.

A kit will typically may include one or more additional containers, each with one or more of various materials (such as reagents, optionally in concentrated form, and/or devices) desirable from a commercial and user standpoint for use of the AM preparations and purified compositions described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

In certain embodiments, the pharmaceutical compositions can be presented in a pack or dispenser device which can contain one or more unit dosage forms containing a compound provided herein. The pack can for example contain metal or plastic foil, such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions containing a compound provided herein formulated in a compatible pharmaceutical carrier can also be prepared, placed in an appropriate container, and labeled for treatment of an indicated condition.

Methods of Treatment

The AM preparations and purified compositions described herein have many uses including research and clinical applications. Based on the results described herein, the AM preparations and purified compositions described herein can be applied to tissues or cells to achieve a desired modulation of physiology. AM preparations and purified compositions described herein can further be added to cell cultures or tissue cultures to achieve a desired effect (as described herein).

AM Preparations and Purified Compositions Described Herein Suppress TGF Promoter Activity The anti-scarring, anti-inflammatory, and anti-angiogenic activities of AM preparations and purified compositions described herein is demonstrated by the suppression of TGF-$\beta$1 promoter activity as shown herein. The fetal portion of the frozen amniotic membrane has a significantly higher anti-scarring effect than that of fresh amniotic membrane; the placental portion of the frozen amniotic membrane also has a significantly higher anti-scarring effect than the fresh amniotic membrane (Example 1). Therefore, the frozen AM, either the placental or fetal portion, showed more potent suppressive effects in TGF-$\beta$ than the fresh AM. This suppressive effect mediated by total AM extract obtained from frozen AM was dose-dependent over a range of 0.4 to 125 µg/ml. Furthermore, such a suppressive effect could not be substituted by high MW HA alone (exceeding 100× of equivalent AM extract), and was lost after digestion with hyaluronidase, suggesting that it was mediated by a complex between HA-I$\alpha$I. Centrifugation at low or high speed did not affect the suppressive effect significantly. However, subsequent lyophilization and reconstitution produced a more potent suppressive effect. Additionally, the overall suppressive effect of AM was more potent than that of AM jelly.

TGF-$\beta$ is the prototypic cytokine that is involved in tissue inflammation, in addition to wound healing and scar formation. See Border, et al., J. Clin. Invest., 90:1-7 (1992); Grande, Proc. Soc. Exp. Biol. Med., 214:27-40 (1997); Jester, et al., Prog. Retin. Eye Res., 18(3):311-356 (1999); and Marek, et al., Med. Sci. Monit., 8(7):RA145-151 (2002). Mammalian cells express three different TGF-$\beta$s: TGF-$\beta$1, TGF-$\beta$2, and TGF-$\beta$3. TGF-$\beta$ is the most potent cytokine promoting myofibroblast differentiation by up-regulating expression of $\alpha$-SMA, integrin $\alpha$5$\beta$1, and EDA domain-containing fibronectin (Fn) in a number of cell types, including fibroblasts. See Tseng, et al., Ocular Surface J., 2(3):177-187 (2004); Ronnov-Jessen, et al., Lab. Invest., 68:696-707 (1993); Verbeek, et al., Am. J. Pathol., 144:372-82 (1994); Hales, et al., Curr. Eye Res., 13:885-90 (1994); Jester, et al., Cornea, 15:505-16 (1996); Serini, et al., J. Cell. Biol., 142: 873-81 (1998); Grande, Proc. Soc. Exp. Biol. Med., 214(1): 27-40 (1997); and Jester, et al., Prog. Retin. Eye. Res., 18:311-56 (1999). TGF-$\beta$ also up-regulates the expression of such matrix components as collagens and proteoglycans, down-regulates proteinase and matrix metalloproteinases, and up-regulates their inhibitors. Collectively, these actions result in increased cell-matrix interactions and adhesiveness, as well as deposition and formation of scar tissue. See Tseng, et al., Ocular Surface J., 2(3):177-187 (2004); Grande, Proc. Soc. Exp. Biol. Med., 214(1):27-40 (1997); Jester, et al., Prog. Retin. Eye. Res., 18:311-56 (1999); and Lawrence, Eur. Cytokine Netw., 7:363-74 (1996).

TGF-$\beta$s exert their actions via binding with TGF-beta receptors (TGF-$\beta$Rs) on the cell membrane. In human cells, there are three TGF-$\beta$Rs, namely TGF-$\beta$R type I (TGF-$\beta$RI), type II (TGF-$\beta$RII), and type III (TGF-($\beta$RIII). TGF-$\beta$s, serving as ligands, bind with a serine, threonine kinase receptor complex made of TGF-$\beta$RI and TGF-$\beta$RII; such a binding is facilitated by TGF-$\beta$RIII, which is not a serine, threonine kinase receptor. See Tseng, et al., Ocular Surface J., 2(3):177-187 (2004); and Massague, et al., Genes and Development., 14:627-44 (2000). Binding with TGF-$\beta$RII activates TGF-$\beta$RI, which is responsible for direct phosphorylation of a family of effector proteins known as Smads, which modulate transcription of a number of target genes, including those described herein, participating in scar formation. See Tseng, et al., Ocular Surface J., 2(3):177-187 (2004); Massague, et al., Genes and Development., 14:627-44 (2000); and Derynck, et al., Biochem. Biophys. Acta., 1333:F105-F150 (1997).

Suppression of TGF-$\beta$ can be achieved by neutralizing antibodies to TGF-$\beta$ and agents that intercede the signaling mediated by TGF-$\beta$ such as decorin. See Shahi, et al., Lancet, 339:213-214 (1992); Petroll, et al., Curr. Eye Res., 1739:736-747 (1998); Yamaguchi, et al., Nature, 346(6281):281-284 (1990); and Logan, et al., Exp. Neurol., 159:504-510 (1999). Most of the literature has shown suppression of TGF-β being achieved at the level of modulating the TGF-β activation, binding with its receptor, or its signal transduction. It has been shown that amniotic membrane can achieve such an inhibition at the level of transcription, i.e., to turn off transcription of TGF-β genes. In particular, amniotic membrane has been shown to suppress TGF-β signaling in human corneal and limbal fibroblasts, and human conjunctival and pterygium body fibroblasts. See Tseng, et al., J Cell Physiol., 179:325-335 (1999); and Lee, et al., Curr. Eye Res., 20(4):325-334 (2000).

Application of the AM preparations and purified compositions described herein can be used to lower the production or activity of TGF-β. Several types of AM compositions, such as AME (total human AM extract), the AME supernatant after centrifugation, AM jelly, and AM stroma were prepared as detailed in Example 1. The effect of various buffers, such as PBS, low salt buffer, high salt buffer, and guanidine HCl on TGF-β activity was examined. Additionally, the effect of various freeze-grinding procedures on TGF-β activity was examined.

Figure 3:
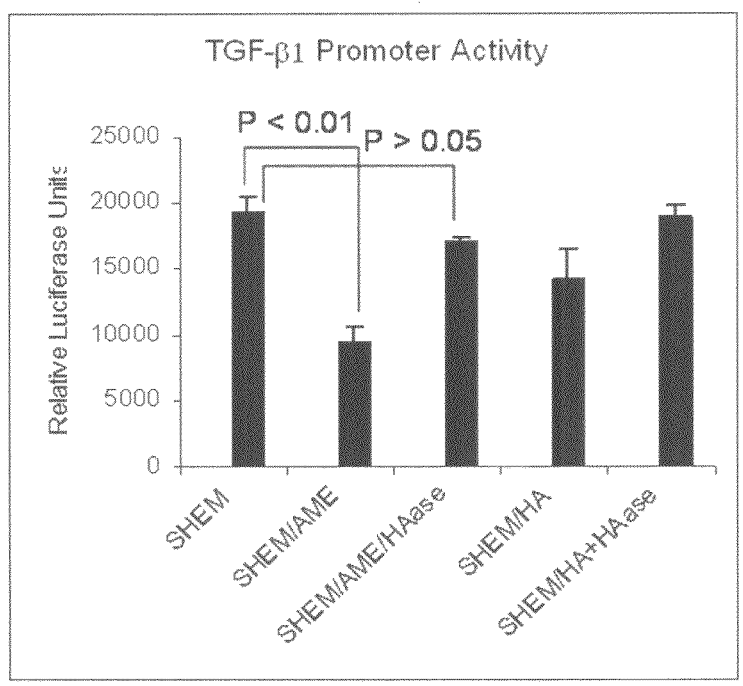
FIG. 3 is a non-limiting example of a bar graph showing the effect of various AM extract preparations on the suppression of TGF-$\beta$1 promoter activity.
Figure 4:
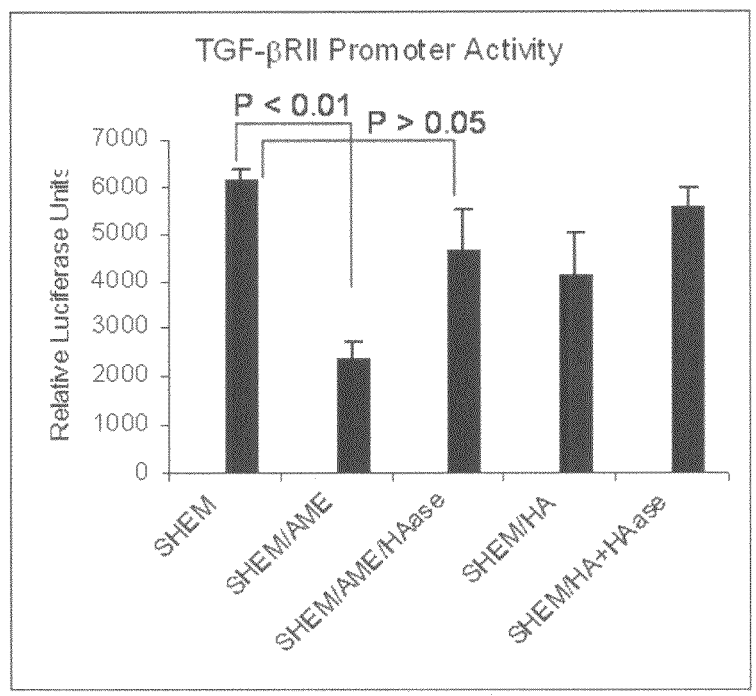
FIG. 4 is a non-limiting example of a bar graph showing the effect of various AM extract preparations on the suppression of TGF-$\beta$RII promoter activity.
Figure 5:
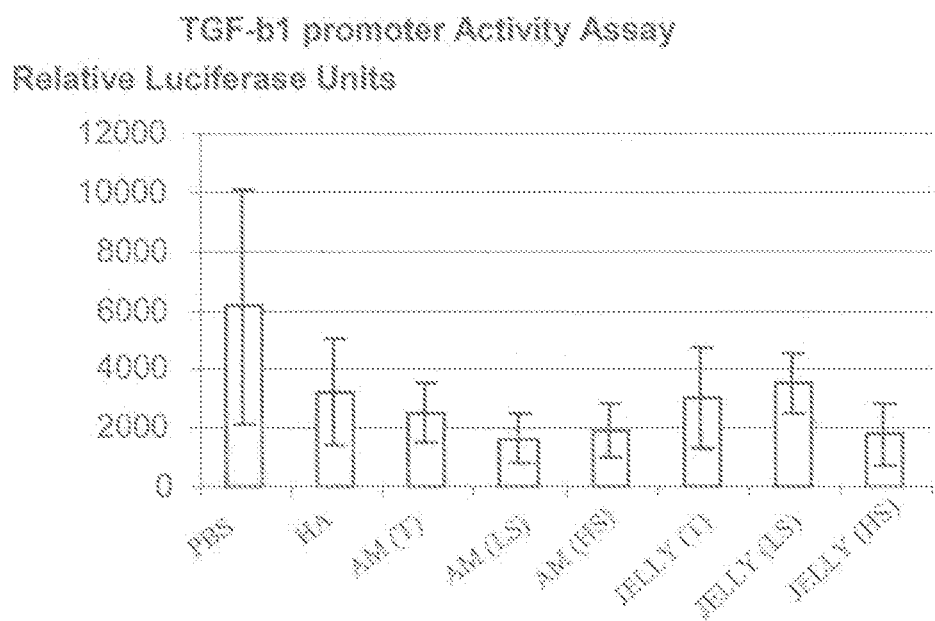
FIG. 5 is a non-limiting example of a bar graph demonstrating that soluble AME and jelly extracts derived after centrifugation do not alter the suppressive effect on TGF-$\beta$ Promoter Activities. HA, AM (Total (T), Low Speed (LS), High speed (HS)) and Jelly (Total (T), Low Speed (LS), High Speed (HS)) showed suppression of TGF-$\beta$1 promoter activation compared to the PBS control when normalized with beta-galatosidase activity.
Figure 6:
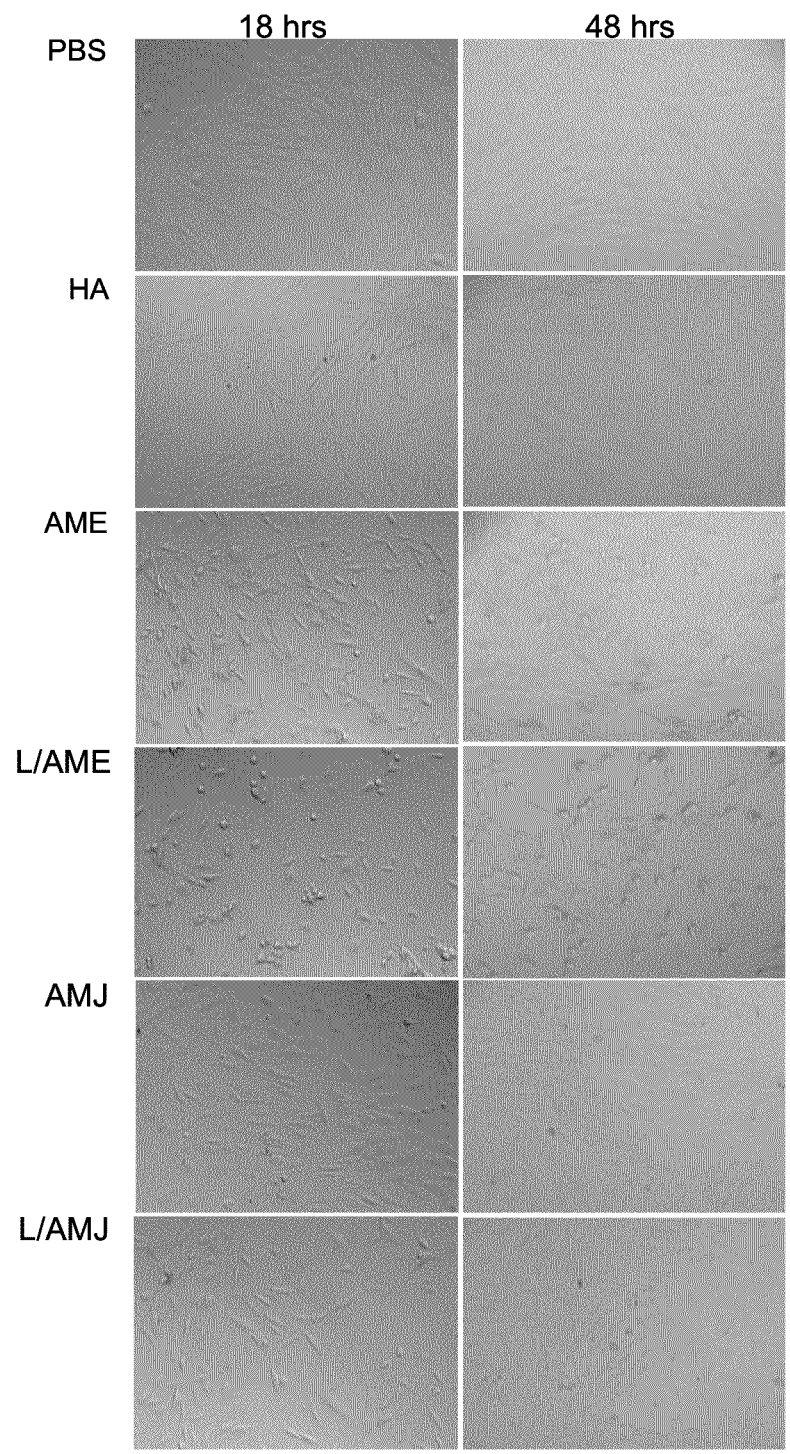
FIG. 6 is a non-limiting example of a set of microscopic images of human corneal fibroblasts showing cell morphology changes either 18 or 48 hours after treatment with various compounds. PBS: the PBS control; HA: hyaluronic acid; AME: amniotic membrane extract; L/AME: lyophilized amniotic membrane extract; AMJ: amniotic membrane jelly; L/AMJ: lyophilized amniotic membrane jelly.
Figure 8:
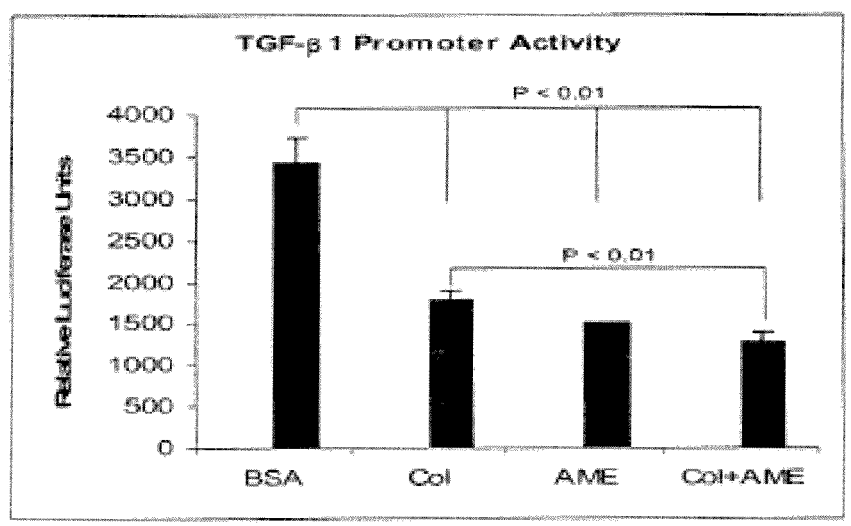
FIG. 8 is a non-limiting example of a bar graph showing the effect of the addition of collagen gel (Col), AM extract AME, or collagen gel mixed with AM extract (Col+AME) on the suppression of TGF-$\beta$ promoter activity. BSA was used as a control.
Figure 9:
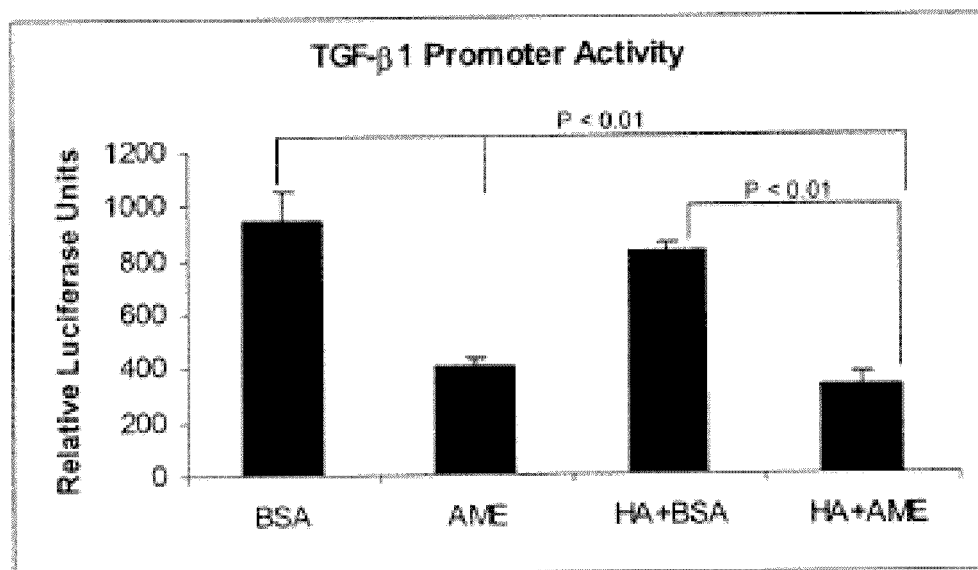
FIG. 9 is a non-limiting example of a bar graph comparing the effect of treatment with AME, HA, or HA+AME, compared to a control assay with BSA alone, on the suppression of TGF$\beta$1 activity. The promoter activity is displayed as relative luciferase units (RLU).

The suppression of TGF-β activity was lost after hyaluronidase digestion, demonstrating that the suppressive effect may be mediated by a HA-related complex (FIG. 3). The suppressive effect was not recovered by addition of HA. The centrifugation step did not alter the suppression of TGF-β activity, in either AME or AM jelly extracts (FIG. 5). Lyophilization enhanced the suppression of TGF-β activity of both AME and jelly extract (FIG. 6). FIG. 8 and FIG. 9 demonstrate that collagen and HA, when added to AME, can enhance the suppression of TGF-β activity. Accordingly, addition of collagen and HA to the AM-based compositions may be useful to treat various diseases involving TGF-13.

As shown herein, TGF-β is downregulated by the disclosed compositions. Accordingly, the compositions described herein can be used to treat diseases related to TGF-β is downregulation, such as angiogenesis, wound healing, and tissue inflammation.

AM Preparations and Purified Compositions Described Herein can Prevent Apoptosis The AM preparations and purified compositions described herein can be used to prevent, lessen, or treat apoptosis in tissues. In some embodiments, the AM preparations and purified compositions described herein can decrease or prevent apoptosis in tissues that have been injured. This anti-apoptotic effect demonstrates that the compositions can be used to prolong the life of organs being stored prior to transplant. The compositions can also be used to treat or prevent damage during and after surgical procedures. Example 3 demonstrates the anti-apoptotic effect of AM extract using a murine model of eye damage. Mouse eyes were collected and damaged either by enzymatic treatment or by mechanical injury, AM extract was administered, and the effect on cellular damage was determined, using an assay that measures apoptotic damage to the nucleus. Incubation with AM extract was found to decrease the levels of apoptosis.

Because of the anti-apoptotic effects exerted by AM preparation, AM preparations and compositions are expected to be useful for preserving tissues (e.g., cornea) before transplantation. The addition of AM preparations to tissues that are being stored can be helpful in lessening cellular damage due to the storage process. For example, the AM preparations and purified compositions described herein can be used to decrease the amount of degradation that occurs in a tissue that is being stored prior to transplantation or surgical procedures. The AM preparations and purified compositions described herein can be added to the storage medium, with or without collagen and/or HA. Stored tissues such as eyes, organs, skin, and the like can benefit from the decreased cellular apoptosis that occurs when an AM composition is added.

Once a donor tissue is harvested, it is typically stored in a storage medium until transplantation. The compositions can be added to the storage medium to prevent cellular apoptosis. For example, the compositions can be added to storage media for preserving limbal epithelial stem cells. Similarly, AM preparation-containing compositions can be added to cell culture medium or digestion medium to prevent cellular (e.g., keratocyte) apoptosis. Because studies described herein show that incubation of AM preparation during dispase digestion (a treatment which mimics surgical and pathological insults such as excimer ablation in PRK and recurrent corneal erosion, respectively) significantly reduced apoptosis of both epithelial cells and keratocytes, the compositions can also be administered to an eye receiving mechanical scraping or excimer laser photoablation to attempt to reduce keratocyte apoptosis, and hence reduce corneal haze. As another example, AM preparation-containing formulations can also be used in surgical conditions or diseases such as recurrent corneal erosion or keratoconus where the basement membrane is dissolved to reduce the keratocyte apoptosis.

Treatment and Prevention of Angiogenesis-Related Diseases

Figure 21:
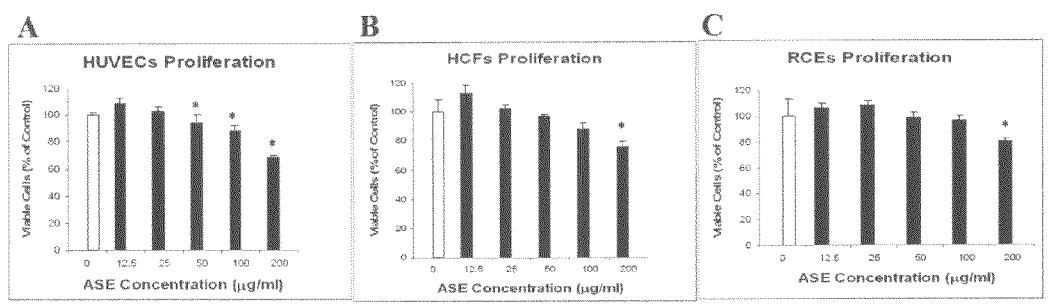
FIG. 21A through 21C is a non-limiting example of a bar graphs demonstrating that ASE preferentially inhibited HUVEC cells. A: Measurement of viable HUVEC cells. B: Measurement of viable HCF cells. C: Measurement of viable RCE cells.
Figure 22:
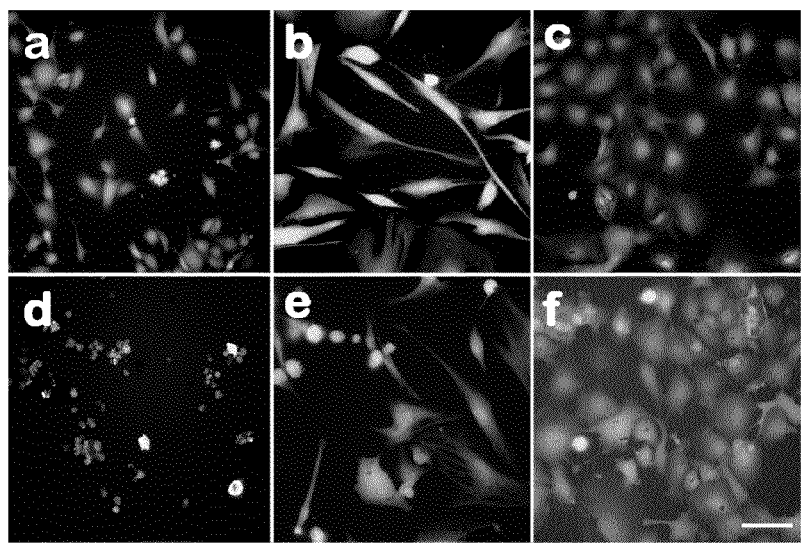
FIG. 22 is a non-limiting example of microscopic images of HUVEC cells. The results showed that HUVEC cells were alive in control without addition of ASE (FIG. 22Aa) but showed pronounced cell death after ASE treatment (FIG. 22Ad). In contrast, both HCF and RCE cells did not reveal any notable cell death in cultures without (FIG. 22Ab and FIG. 22Ac, respectively) or with (FIG. 22Ae and FIG. 22A, respectively) ASE treatment. Hoechst-33342 staining showed that ASE-treated HUVECs had 61.6±7.7% of condensed and fragmented nuclei (FIG. 22Bd), which was significantly higher than 3.1±1.8% of the control without ASE treatment (FIG. 22Ba, also see FIG. 21C, p<0.001). In contrast, there was no obvious apoptosis in either HCFs or RCEs without (FIG. 22Bb and FIG. 22Bc, respectively) or with (FIG. 22Be and FIG. 22Bf, respectively) ASE treatment.
Figure 22:
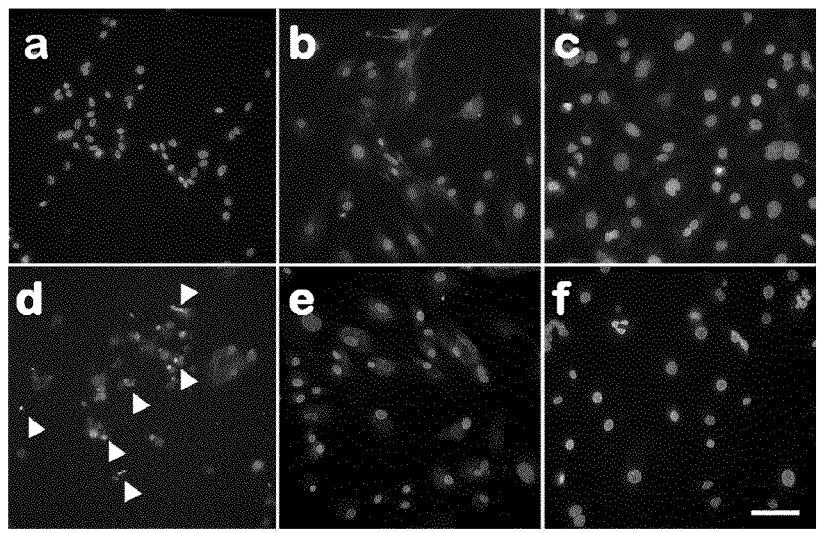
Figure 24:
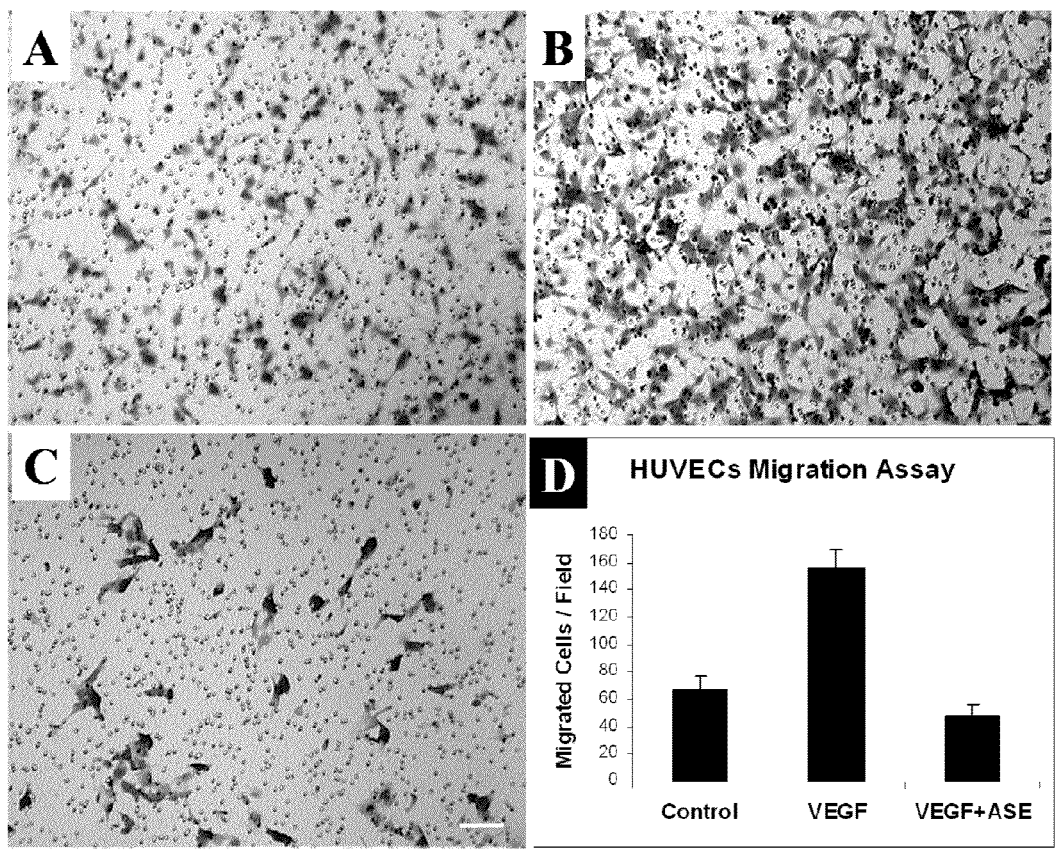
FIG. 24 is a non-limiting example showing the effect of ASE on the inhibition HUVEC migration stimulated by VEGF. A: Control (no VEGF or ASE). B: Addition of VEGF increased cell migration. C: Addition of VEGF and 200 µg/ml ASE. The addition of the ASE retarded the VEGF-induced migration.
Figure 25:
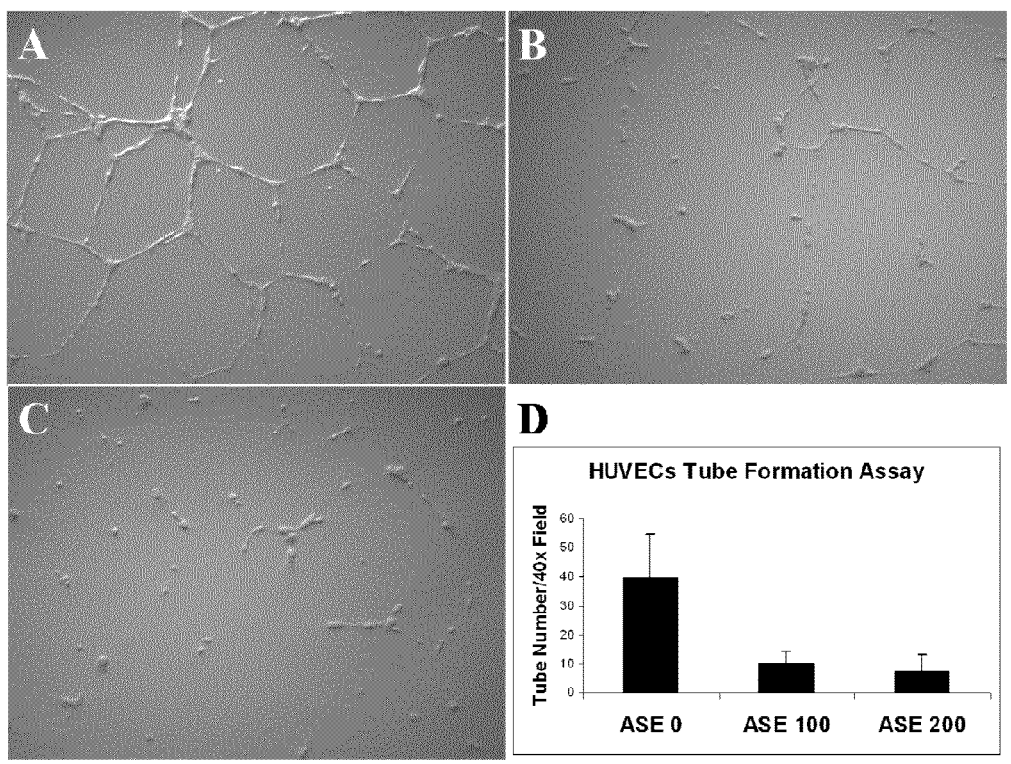
FIG. 25 is a non-limiting example of a panel of microscopic images (A-C) and a bar graph (D) demonstrating that the addition of ASE inhibits tube formation. To perform the in vitro tube formation assay, HUVEC cells were seeded on Matrigel. A: Tube-like formation in the control culture. B: Addition of 100 µg/mL ASE added to the culture inhibited tube formation. C: Addition of 200 µg/mL ASE added to the culture inhibited tube formation. D: Bar graph quantitating the number of tubes formed per field from A, B, and C.

As described herein, the anti-angiogenic activity of the AM preparations and purified compositions described herein was demonstrated using soluble protein extracts prepared from the avascular stroma of cryopreserved AM. The AM stromal extract (ASE) was found to have a potent anti-angiogenic action on cultured human umbilical vein endothelial cells (HUVECs) by inhibiting proliferation, inducing apoptosis, attenuating migration, and inhibiting tube formation. Example 8 demonstrates that an amniotic membrane stromal extract (ASE) has anti-angiogenic properties. ASE was found to inhibit HUVEC cell proliferation (FIG. 21). ASE was also found to induce apoptosis in HUVEC cells (FIG. 22). ASE The inhibitory effect of ASE on VEGF-induced cell migration was demonstrated using a transwell assay (FIG. 24). ASE was further found to inhibit tube formation of HUVEC cells (FIG. 25).

Taken together, these results demonstrate that the AM preparations and purified compositions described herein can be useful for treatment of angiogenesis-related diseases. Exemplary angiogenesis-related diseases that can be treated include but are not limited to tumor growth, cancer, and of ophthalmological conditions such as corneal graft rejection, ocular neovascularization, retinal neovascularization including neovascularization following injury or infection, diabetic retinopathy, macular degeneration, retrolental fibroplasia, neovascular glaucoma, retinal ischemia, vitreous hemorrhage, and the like.

Exemplary cancer types that can be treated using the AM preparations and purified compositions described herein include but are not limited to Acute Lymphoblastic Leukemia, Acute Myeloid Leukemia, Adrenocortical Carcinoma, AIDS-Related Cancers, AIDS-Related Lymphoma, Anal Cancer, Astrocytoma, Basal Cell Carcinoma, Bile Duct Cancer, Bladder Cancer, Bladder Cancer, Bone Cancer, Brain Stem Glioma, Brain Tumor, Breast Cancer, Bronchial Adenomas, Burkitt's Lymphoma, Carcinoid Tumor, Carcinoma, Central Nervous System Lymphoma, Cerebellar Astrocytoma, Cervical Cancer, Chronic Lymphocytic Leukemia, Chronic Myelogenous Leukemia, Chronic Myeloproliferative Disorders, Colon Cancer, Colorectal Cancer, Cutaneous T-Cell Lymphoma, Endometrial Cancer, Ependymoma, Esophageal Cancer, Extragonadal Germ Cell Tumor, Eye Cancer, Intraocular Melanoma, Eye Cancer, Retinoblastoma, Gallbladder Cancer, Gastrointestinal Carcinoid Tumor, Gastrointestinal Stromal Tumor (GIST), Germ Cell Tumor (Extracranial), Germ Cell Tumor (Extragonadal), Germ Cell Tumor (Ovarian), Gestational Trophoblastic Tumor, Glioma, Hairy Cell Leukemia, Head and Neck Cancer, Hepatocellular (Liver) Cancer, Hodgkin's Lymphoma, Hypopharyngeal Cancer, Hypothalamic and Visual Pathway Glioma, Intraocular Melanoma, Islet Cell Carcinoma (Endocrine Pancreas), Kaposi's Sarcoma, Kidney (Renal Cell) Cancer, Laryngeal Cancer, Leukemia (Acute Lymphoblastic), Leukemia (Acute Myeloid), Leukemia (Chronic Lymphocytic), Leukemia (Chronic Myelogenous), Lip and Oral Cavity Cancer, Liver Cancer, Lung Cancer (Non-Small Cell), Lung Cancer (Small Cell), Lymphoma, (Cutaneous T-Cell), Lymphoma (Non-Hodgkin's), Malignant Fibrous Histiocytoma of Bone/Osteosarcoma, Medulloblastoma, Melanoma, Merkel Cell Carcinoma, Mesothelioma, Metastatic Squamous Neck Cancer with Occult Primary, Multiple Endocrine Neoplasia Syndrome, Multiple Myeloma/Plasma Cell Neoplasm, Mycosis Fungoides, Myelodysplastic Syndromes, Myelodysplastic/Myeloproliferative Diseases, Myelogenous Leukemia, Myeloid Leukemia, Myeloproliferative Disorders, Nasal Cavity and Paranasal Sinus Cancer, Nasopharyngeal Cancer, Neuroblastoma, Oral Cancer, Oropharyngeal Cancer, Osteosarcoma/Malignant Fibrous Histiocytoma of Bone, Ovarian Cancer, Ovarian Epithelial Cancer, Ovarian Germ Cell Tumor, Ovarian Low Malignant Potential Tumor, Pancreatic Cancer, Parathyroid Cancer, Penile Cancer, Pheochromocytoma, Pineoblastoma and Supratentorial Primitive Neuroectodermal Tumors, Pituitary Tumor, Plasma Cell Neoplasm/Multiple Myeloma, Pleuropulmonary Blastoma, Prostate Cancer, Rectal Cancer, Retinoblastoma, Rhabdomyosarcoma, Salivary Gland Cancer, Sarcoma (Kaposi's), Sarcoma (uterine), Sezary Syndrome, Skin Cancer (non-Melanoma), Skin Cancer (Melanoma), Skin Carcinoma (Merkel Cell), Small Intestine Cancer, Soft Tissue Sarcoma, Squamous Cell Carcinoma, Stomach (Gastric) Cancer, T-Cell Lymphoma, Testicular Cancer, Thymoma, Thyroid Cancer, Trophoblastic Tumor, Gestational, Urethral Cancer, Uterine Cancer, Endometrial, Uterine Sarcoma, Vaginal Cancer, Visual Pathway and Hypothalamic Glioma, Vulvar Cancer, Waldenström's Macroglobulinemia, Wilms' Tumor, and the like.

The compositions and methods described herein are provided further detail in the following examples. These examples are provided by way of illustration and are not intended to limit the invention in any way.

EXAMPLES

Example 1

Suppressive Activities of Various Amniotic Membrane Preparations

Hyaluronidase Digestion

AM total water-soluble extracts (AME) prepared from frozen AM were mixed with or without 10 units/ml hyaluronidase (Sigma #H1136) in the reaction buffer (50 mM HEPES, pH7.5, 0.1M NaCl, 1% Triton X-100, 0.1% BSA supplemented with the above protease and phosphatase inhibitors for 2 hours at 37° C. using a positive control of high MW HA (cat# H1876, Sigma) purified from human umbilical cords.

Cell Culture and TGF-β1 Promoter Suppression

When human corneal fibroblasts cultured on 100 mm plastic dish in DMEM/10% FBS reached 80% confluency (~1.0× $10^6$ cells), cells were washed twice with DMEM/10% FBS. Adenoviruses-TGF-β1 promoter-luciferase (MOI=37.5) and Adeno-CMV-beta-gal (MOI=30) were added to the culture plates with 10 ml of the fresh DMEM/10% FBS and cells were incubated at 37° C. for 4 hours, and trypsinized for 5 minutes using 4 ml prewarmed trypsin/EDTA. After trypsin/EDTA activity was neutralized with 8 ml of DMEM/10% FBS, cells were collected into a 15 ml tube and centrifuged at 1,500 rpm (~600×g) for 5 min. After decanting the medium, cells were resuspended in 15 ml DMEM/10% FBS, and cell viability was measured by trypan blue stain. Viable $3\times10^4$ cells were seeded on a plastic 24 well or on the stromal surface of AM inserts. A total of 4 wells or inserts were prepared. Cells were then incubated at 37° C. in a $CO_2$ incubator for 48 hours.

After carefully removing the growth medium from each well, cells were rinsed with 0.5 ml PBS at lease twice, taking care not to dislodge attached cells. After removing as much as PBS in the well, 100 μl 1× lysis buffer was added to cover the cells, and cells were mechanically scraped and transferred to a microcentrifuge tube placed on ice. Cell lysates were collected by vortexing for 10-15 sec and centrifuging at 12,000×g for 15 sec at room temperature. The supernatant designated as cell lysate was stored at −80° C. prior to assaying for luciferase activities.

Suppression of TGF-β1 Promoter Activity by Different AM Extracts

In FIG. 1, compared to the plastic control (PL), both the placental portion and the fetal portion of frozen amniotic membrane (FRO/P and FRO/F, respectively) showed significant suppression of TGF-β1 promoter activity (each P<0.01). For the fresh placenta, the placental portion of amniotic membrane (FRE/P) also exhibited a significant suppression of TGF-β1 promoter activity (P<0.05). Nevertheless, the fetal portion of the fresh amniotic membrane (FRE/F) did not show any suppressive effect (P=0.5). These results indicated that the fetal portion of the fresh amniotic membrane does not have the same anti-scarring effect as the frozen counterpart. For the frozen amniotic membrane, the suppressive effect by the placental portion (FRO/P) was not significantly different from that by the fetal portion (P=0.3). For the fresh amniotic membrane, the suppressive effect by the fetal portion (FRE/F) was not significantly from the placental portion (FRE/P) (P=0.1). For the placental portion, the suppressive effect by the frozen amniotic membrane (FRO/P) was significantly better than the fresh amniotic membrane (FRE/P) (P<0.05). In the fetal portion, however, the suppressive effect by the frozen amniotic membrane (FRO/F) was not significantly different than the suppressive effect of the fresh amniotic membrane (FRE/F) (P=0.1).

Figure 2:
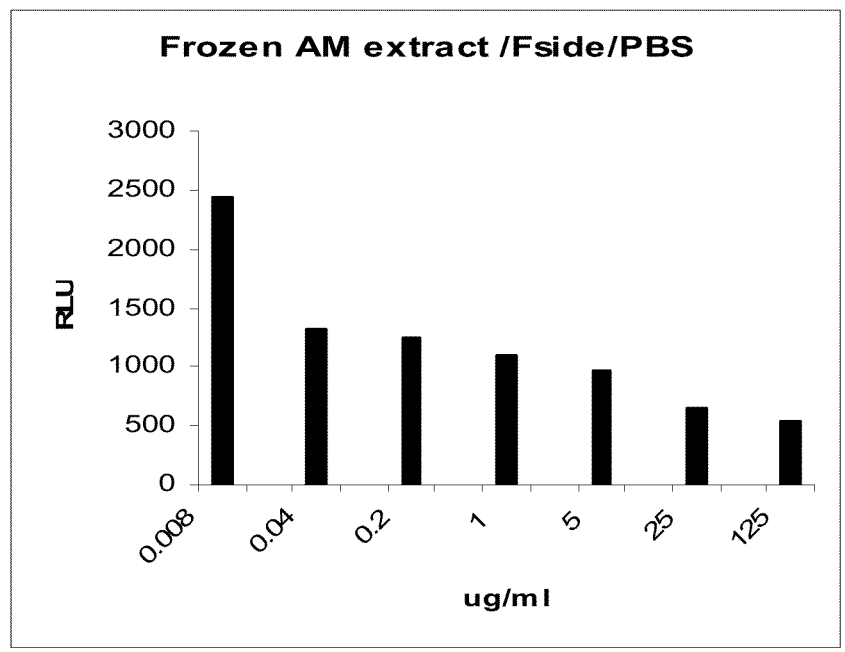
FIG. 2 is a non-limiting example of a bar graph showing the dose response curve of TGF-$\beta$1 promoter activity suppression. RLU: Relative luciferase units.

Suppression of TGF-β1 Promoter Activity is Dose-dependent and Lost after Digestion with Hyaluronidase The suppression of TGF-β1 promoter activity by total water-soluble AM extracts prepared from frozen AM obeyed a dose-responsive curve from 0.04 to 125 μg/ml (FIG. 2). As shown by the promoter activity of TGF-β1 and TGF-βRII, the suppressive effect of 25 μg/ml of total water-soluble AM extracts prepared from frozen AM was lost when pre-treated with hyaluronidase, indicating that such a suppressive effect was mediated by an HA-related complex (FIG. 3). It should be noted that 25 μg/ml AM extracts contained less than 0.78 μg/ml HA.

Lost Suppressive Effect from Hyaluronidase Cannot be Recovered by Addition of HA Although 100 μg/ml high MW HA alone showed a mild suppressive activity, its magnitude was still significantly less than 25 μg/ml AM extracts. Taken together, these data suggest that the suppressive effect of AM extracts was mediated by HA-linked complex, i.e., HA-IαI complex.

Soluble AME and Jelly Extracts Derived after Centrifugation do not Change the Suppressive Effect on TGF-β1 Promoter Activities Compared to the PBS control, HA, AM (Total, Low Speed, High speed) and Jelly (Total, Low Speed, High Speed) showed suppression of TGF-β1 promoter activation when normalized with beta-galatosidase activity. P value indicated there was not statistically significant due to the variation among the control group (data not shown). By comparing total AME and two conditions of centrifuged soluble AME, results suggested that there was no significant difference. However, without centrifugation of AME showed less suppression compare with low or high soluble AME. Likewise, Jelly/T indicated less TGF-β suppression activities in comparison with Jelly/HS (FIG. 5).

Lyophilization Enhanced the Suppressive Effect of AME and Jelly Extract

Human corneal fibroblasts showed no change in cell morphology in the control, HA alone, and low concentrations of AME or jelly extracts (Data not shown). However, cells showed a marked change to slender and small cells after the treatment with high concentration of AME and L/AME, as early as 18 hrs after seeding (FIG. 6). Furthermore, the cell density also decreased. The above changes were even more dramatic in lyophilized AME or L/AME than their non-lyophilized counterparts in AME or Jelly extracts, respectively (FIG. 6).

Figure 7:
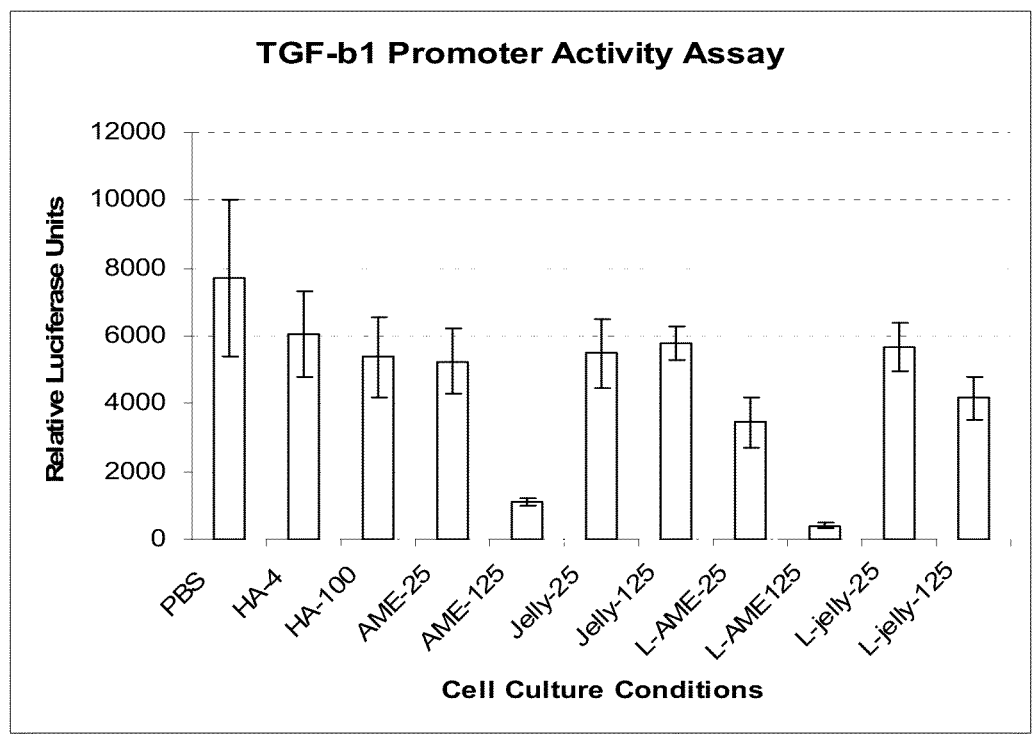
FIG. 7 is a non-limiting example of a bar graph demonstrating the effect of AME (at 25 or 125 µg/ml), with or without lyophilized (L), on the suppression of TGF$\beta$1 activity. The activity is measured in relative luciferase units (RLU).

To examine whether the TGF-beta promoter was suppressed during AME treatment, luciferase assays were performed. Beta-galatosidase assay was used as the transfection control. The result indicated that AME-125, L-AME-25, L-AME-125, L-Jelly-125 showed a significant differences in inhibiting TGF-beta 1 promoter activities, the percentage of inhibitions were 86% ($P<0.01$), 55% ($P<0.1$), 95% ($P<0.01$), and 46% ($P<0.1$), respectively (FIG. 7). The data suggests that lyophilized form of AME or Jelly at a high concentration of 125 μg/ml was more effective than the non-lyophilized AME form. Although the lowest concentration of commercial HA (4 μg/ml) was close to the concentration HA (3.8 μg/ml) in AME/125, the effectiveness suppression in AME/125 is far more potent than HA. (Data not shown). Furthermore, the AME form overall illustrated a better TGF-beta suppression than the Jelly form.

Suppression of TGF-β1 Promoter Activity by AM Extracts Mixed with Collagen Gel or HA A mixture of native type 1 collagen gel and water-soluble AM extract was then prepared. To prepare this mixture, collagen gel was first prepared by diluting a 4 mg/ml stock collagen solution prepared from rat tail tendon (BD Biosciences, San Jose, Calif.) with 0.1N acetic acid and mixing it with a 1/20 volume ratio of 20×DMEM and 1 N NaOH. A collagen gel formed after incubation at 37° C. Next, water-soluble AM extract (prepared as described herein) was diluted in DMEM to a concentration of 25 μg/ml and then mixed with the collagen gel. The suppressive effect of AM extract mixed in type 1 collagen gel was similar to that of AM extracts (AME) used alone, when compared to the control which was added with BSA alone (FIG. 8, $p<0.01$). Although collagen gel alone (Col) also showed a similar suppressive activity when compared to the plastic control (FIG. 8, $p<0.01$), addition of AME in collagen gel (Col+AME) resulted in further suppression (FIG. 8, $p<0.01$). When water-soluble AM extracts (AME) were mixed in HA gel, the suppressive effect on TGF-β1 promoter activity was better preserved as compared to HA alone (mixed with BSA as a control) (FIG. 5, $p<0.01$) similar to that exerted by AME alone (FIG. 9). Accordingly, an AM extract composition, or its combination with collagen can be useful to suppress TGF-β activity in eye tissue.

Example 2

Characterization of Amniotic Membrane Components

Material and Methods

The concentration of proteins in each extract was quantitated by the BCA Protein Assay Kit (Pierce, Rockford, Ill.). The concentration of hyaluronic acid (HA) in each extracts was assayed with Hyaluronic Acid (HA) Quantitative Test Kit (Corgenix, Westminster, Colo.) based on ELISA using a standard curve provided by the manufacturer prepared by serial dilution of HA.

HA Molecular Weight Range Analysis by Hyaluronidase Digestion

The HA molecular weight ranges of the extracts were analysed by agarose gel electrophoresis according to the method described by Lee and Cowman (Lee H. G. and Cowman, M. K. An Agarose Gel Electrophoretic Method for Analysis of Hyaluronan Molecular Weight Distribution. Analytical Biochemistry, 1994, 219, 278-287). The samples were subjected to 0.5% agarose gel electrophoresis followed by staining using 0.005% Stains-All (Sigma, cat#23096-0) in 50% ethanol. The gel was stained overnight under a light-protective cover at room temperature (Shorter staining periods of 3-4 hr can also give acceptable results). HA was visualized as blue bands after destaining by transferring the gel to $H_2O$ and exposed to the room light for approximately 6 hr. The molecular weight standards included lamda DNA-BstE II digested restriction fragments (cat# D9793, Sigma) ranging in MW from 0.9 to $5.7 \times 10^6$. The authenticity of HA was further verified by incubation of the extract with or without 10 units/ml hyaluronidase (Sigma #H1136) in the reaction buffer (50 mM Tris-HCl, pH7.5, 0.1 M NaCl, 1% Triton X-100, 0.1% BSA supplemented with the above protease and phosphotase inhibitors) for 2 h at 37° C. using a positive control of high MW HA (cat# H1876, Sigma) purified from human umbilical cords.

Western Blot Analyses

The above extracts were electrophoresized on 4-15% denatured acrylamide gels and transferred to the nitrocellulose membrane, and then immunoblotted with a rabbit anti-human inter-α-trypsin inhibitor (rabbit polyclonal antibody (cat# A0301, DAKO at 1:1000), a rabbit anti-human TSG-6 polyclonal antibody (provided by Dr. Tony Day at 1:1000 dilution), a rat monoclonal anti-PTX3 antibody (Alexis Biochemicals, ALX-804-464, 1 μg/ml), an anti-thrombospondin-1 antibody obtained from Calbiochem (Cat# BA24), and a goat anti-human Smad 7 antibody (AF2029, 1:1000, R & D Systems). Immunoreactive protein bands were detected by Western LightingTMChemiluminesence Reagent (PerkinElmer).

Results

Experiments showed that the observed suppressive effect on the TGF-β1 promoter activity was abolished when water-soluble AM extracts were pre-heated at 90° C. for 10 minutes, suggesting that the responsible component(s) most likely contained protein(s), of which the conformation is important.

Quantitation of HA and Proteins in AM Extracts

The results summarized in the Table below showed that all AM and jelly extracts contained both HA and proteins. In general, the weight ratio between proteins and HA was high in the Total Extract than the supernatant (e.g., L and H for PBS, and A for Buffer A) after centrifugation for AM, suggesting that most protein-containing materials were eliminated by centrifugation. However, this trend was not noted in AM Jelly, suggesting that AM extracts contained more proteins than Jelly (see T under PBS and T under A/B/C). The ratio between proteins and HA was also increased from Extract A to Extracts B and C for both AM and AM jelly, further supporting that HA was mostly present in the soluble form, and vice versa proteins were found more in the water-insoluble components. Furthermore, HA was largely removed from AM Jelly after centrifugation in A/B/C.

Tumor Necrosis Factor-Stimulated Gene 6 (TSG-6) is also Present in AM Extracts

Figure 14:
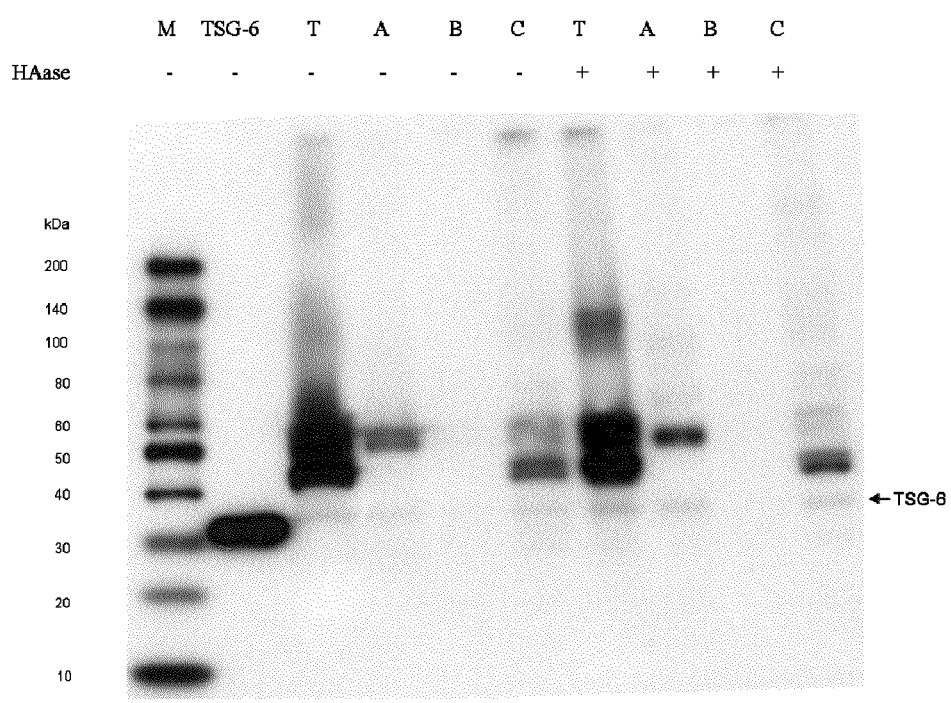
FIG. 14 is a non-limiting example of an immunoblot of TSG-6 (Tumor Necrosis Factor-Stimulated Gene 6), either with (+) or without (−) hyaluronidase treatment. The samples included total AM extract without centrifugation (T), AM Extract after extraction in isotonic low salt buffer (buffer A); high salt buffer (B); or 4 M guanidine HCl (C); as detailed in Example 2. TSG-6 was present in the total extract, buffer A extract, and buffer C extract. The addition of hyaluronidase did not appear to alter the TSG-6 level in the extracts.
Figure 15:
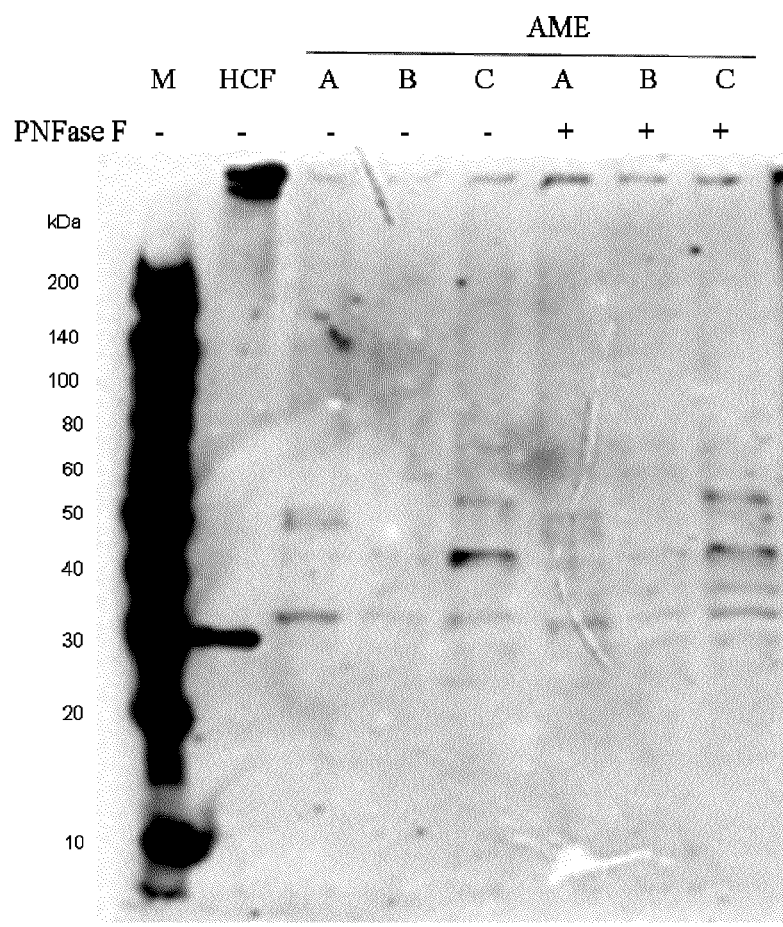
FIG. 15 is a non-limiting example of an immunoblot analysis of the deglycosylation of TSG-6 in AM. AM extract A, B, and C were treated with (+) or without 20 units/ml PNGase F at 37° C. for 3 hours. Glycosylation of TSG-6 in AM was then analyzed by western blot. The cell lysate of human corneal fibroblast (HCF) was used as a positive control.
Figure 16:
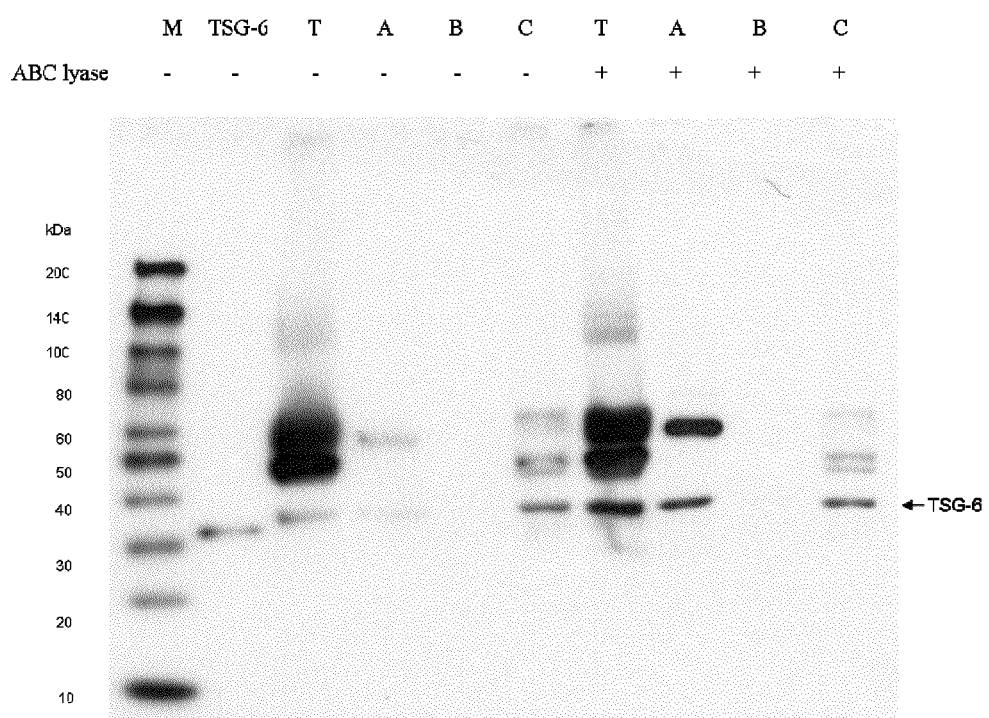
FIG. 16 is a non-limiting example of an immunoblot analysis of potential TSG-6 complexes in AM by digestion with Chondroitin Sulfate ABC lyase. AM extract A, B, and C were treated without (−) or with (+) 1 unit/ml ABC lyase at 37° C. for 2 hours. The possible disruption of TSG-6 complexes was then analyzed by western blot using an anti-TSG-6 antibody RAH-1:1:1000.
Figure 17:
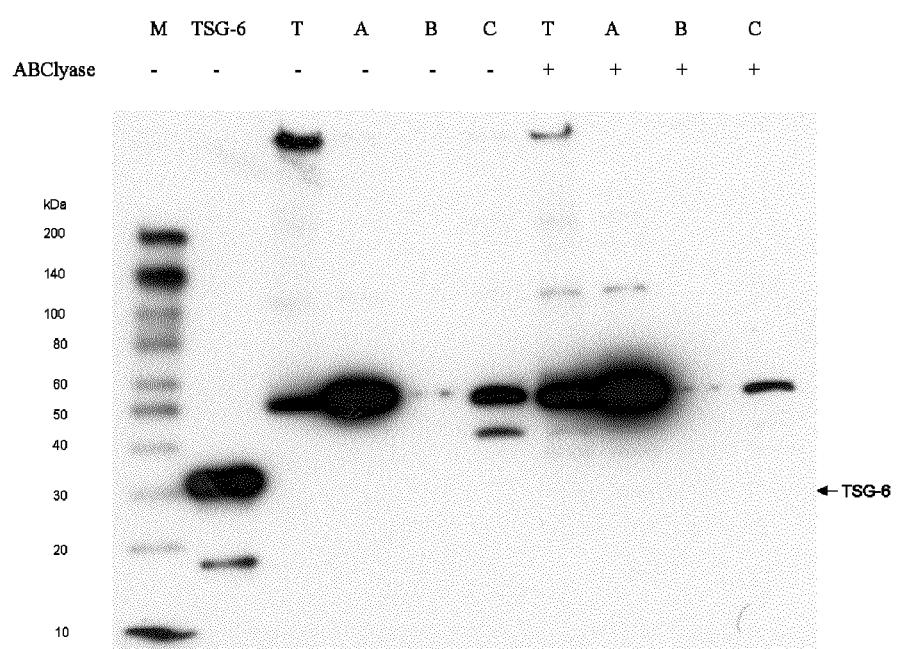
FIG. 17 is a non-limiting example of an immunoblot of potential TSG-6 complexes in AM by digestion with Chondroitin Sulfate ABC lyase. This is the same experiment as shown in FIG. 16 except that a different TSG-6 antibody was used. Here, the anti-TSG-6 antibody was obtained from R & D Systems (cat# MAB2104).

FIG. 14 showed that TSG-6 (~38 kDa) was present in Total, Extract A and Extract C. In Extract A, there was a band of ~38 kDa migrated close to that of the purified TSG-6 (35 kD). The identity of other bands of ~45 and 55 kDa was unknown. Total AM extract (without centrifugation) "T" showed two bands (both above 35 kD), and the higher one (55 kD) that were found in Extract A (after centrifugation), while the lower one (45 kD) was found in Extract C. All of these bands were not significantly altered when samples were treated with hyaluronidase (FIG. 14) or with F-glycosidase (FIG. 15). However, digestion with chondroitin sulfate ABC lyase resulted in more noticeable 38 kD band using antibody RAH-1 (FIG. 16) but not using antibody MAB2104 (FIG. 17).

Figure 18:
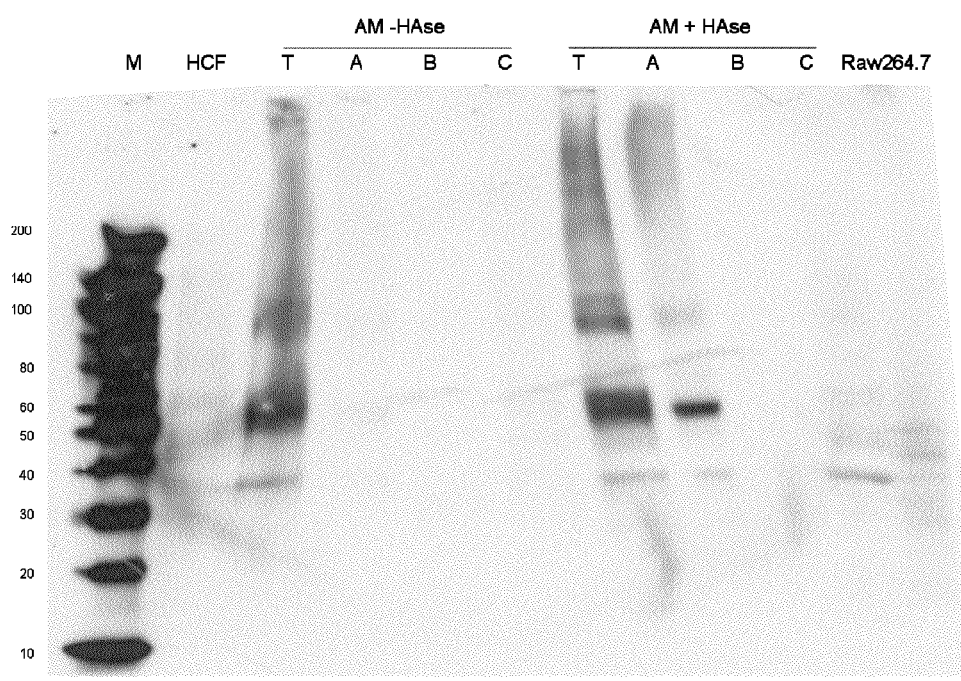
FIG. 18 is a non-limiting example of an immunoblot demonstrating the presence of Pentraxin (PTX3) in AM, using a rat monoclonal anti-PTX3 antibody obtained from Alexis Biochemicals. HCF: human corneal fibroblast, T, A, B, C: AM extract Total, A, B, C, respectively; HAse, Hyaluronidase.

Pentraxin (PTX-3) is Exclusively Present in Water-Soluble AM Extracts and Forms a Complex with HA FIG. 18 showed that PTX3 could also be present in AM extracts and is complexed with HA in the water soluble extract A only.

TABLE 1

| | Tissue | | | | | | | | | | | | | |
|---|---|---|---|---|---|---|---|---|---|---|---|---|---|---|
| | AM | | | | | | | Jelly | | | | | | |
| | | | | Buffer | | | | | | | | | | |
| | PBS | | | A/B/C | | | | PBS | | | A/B/C | | | |
| | | | | | Fraction | | | | | | | | | |
| | T | L | H | T | A | B | C | T | L | H | T | A | B | C |
| Protein (µg/ml) | 8645 | 1370 | 1467 | 8645 | 2731 | 930 | 2698 | 3836 | 3645 | 3589 | 3836 | 3893 | 527 | 1364 |
| HA (µgml) | 75 | 62 | 44 | 60 | 74 | 7 | 35 | 80 | 90 | 96 | 129 | 94 | 2 | 7 |
| Protein/HA | 115 | 22 | 33 | 144 | 37 | 133 | 77 | 48 | 41 | 37 | 30 | 41 | 264 | 195 |

[Note]:
T: Total, L: the supernatant following the low speed centrifugation of the total extract, H: the supernatant following the low speed centrifugation of the total extract, A, B, C: Extracts, see text.

Figure 10:
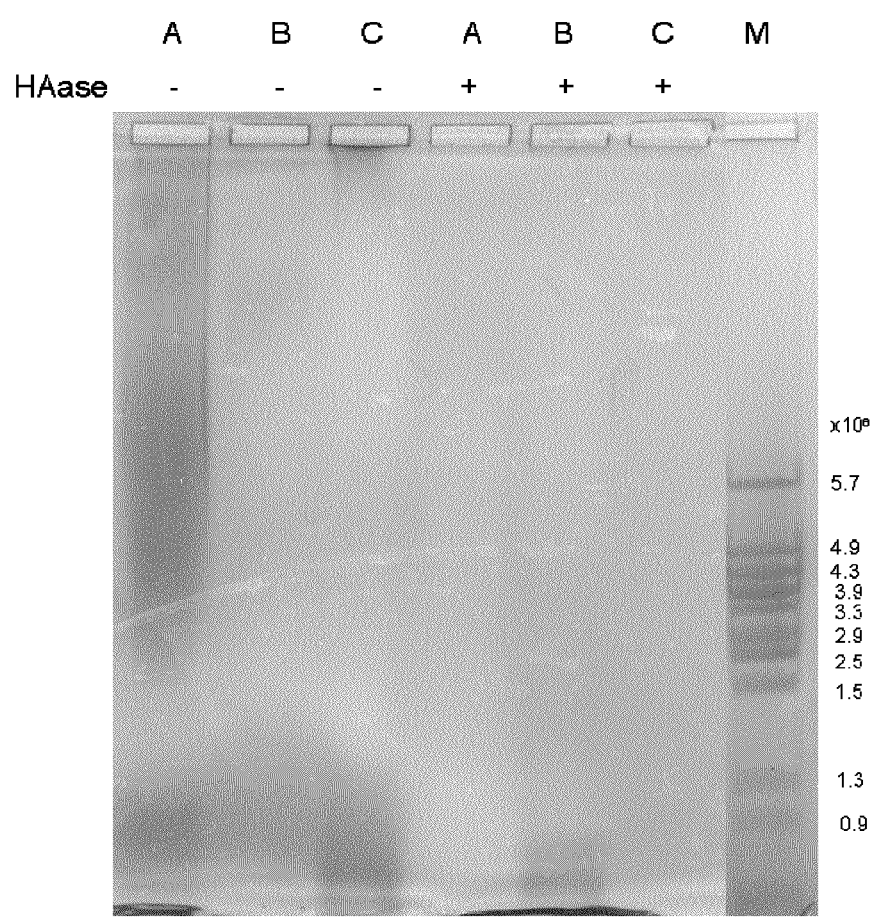
FIG. 10 is a non-limiting example of an analysis of hyaluronan MW Ranges in AM Extracts of various AM extracts, separated by agarose gel electrophoresis. Amniotic membrane extracted by buffer A, B, C were treated with or without hyaluronidase and electrophoretically separated by a 0.5% agarose gel.
Figure 11:
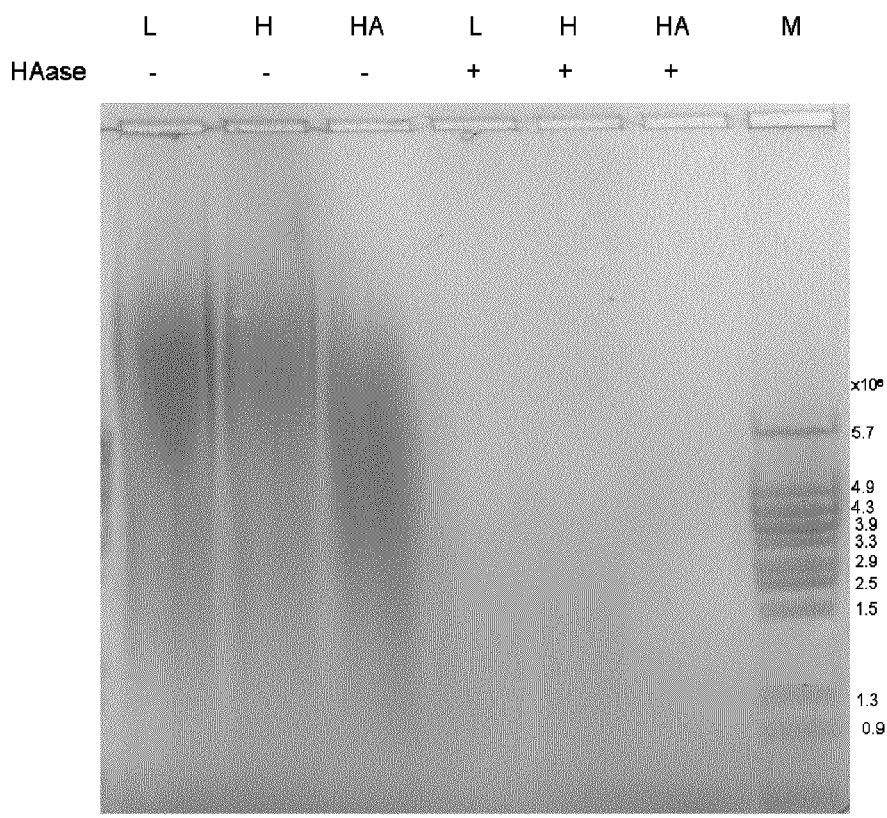
FIG. 11 is a non-limiting example of an analysis of hyaluronan MW Ranges in AM Extracts of various AM extracts, separated by agarose gel electrophoresis. Amniotic membrane extracted by buffer PBS were treated with or without hyaluronidase (10 units/ml in Tris-HCl, pH 7.5, 150 mM NaCl) for 2 hr at 37° C. and run through 0.5% agarose gels. HA: positive hyaluronic acid control; L: AM extract after low speed centrifugation; H: AM extract after high speed centrifugation.

HA in Different AM Extracts have Molecular Weights Greater than One Million Daltons High molecular weight (>$10^6$ daltons) of HA was present in the total extracts and Extract A (FIG. 10). However, even higher MW of HA was present in Extract B, while HA was found in a narrow band with even higher MW in Extract C (FIG. 10). All of the HA-containing components disappeared after hyaluoridase digestion, confirming that they indeed contained HA. Compared to the positive control of HA obtained from Sigma (cat# H1136), a similar high molecular weight (>$10^6$ daltons) of HA was also found in both supernatants obtained after low and high speeds of centrifugation (FIG. 11). Again these HA-containing bands disappeared after hyaluronidase digestion. A similar result was obtained for AM jelly (not shown).

Figure 12:
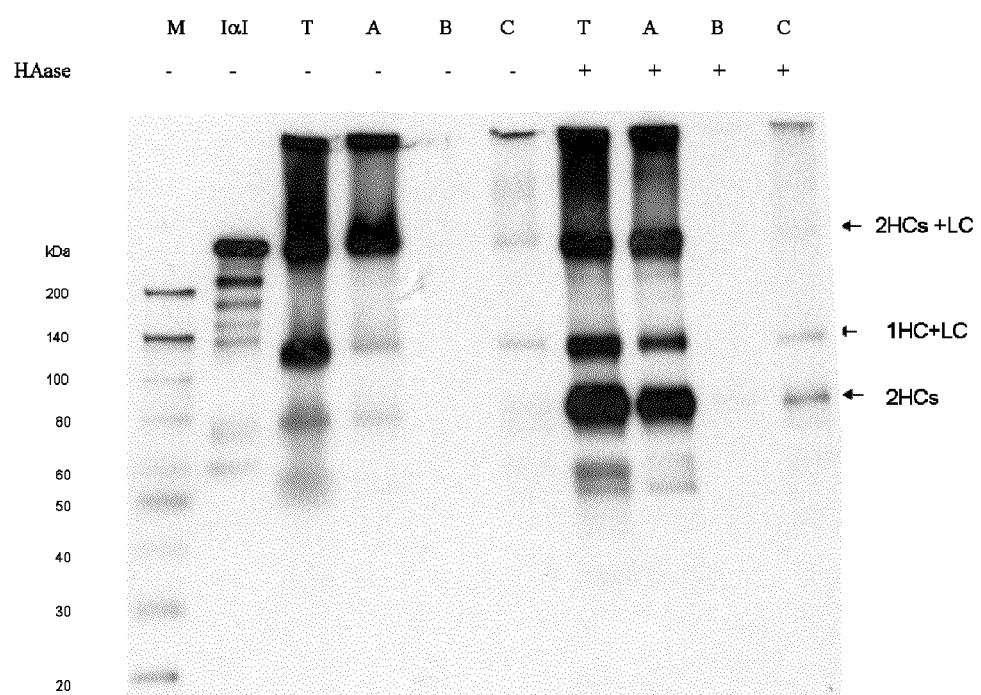
FIG. 12 is a non-limiting example of a photograph of a western blot demonstrating that the inter-$\alpha$-trypsin inhibitor (IαI) is present in AM Extracts. IαI was present in AM extract A and C although the signal of bikunin was very weak (~39 kDa). Prior to transfer to the western blot, the extract was separated on a 4-15% denatured acrylamide gel.
Figure 13:
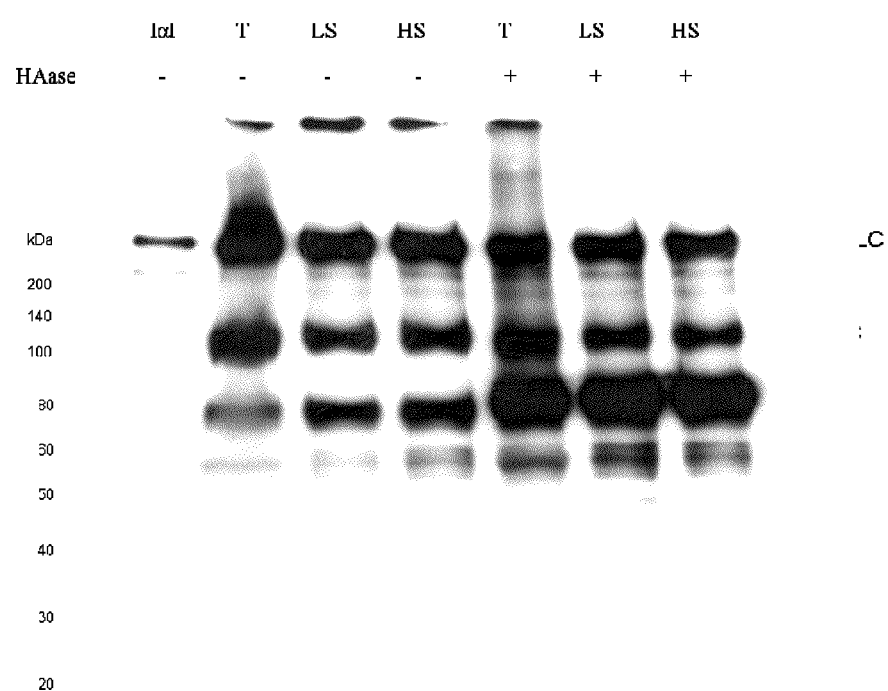
FIG. 13 is a non-limiting example of an immunoblot demonstrating that the inter-α-trypsin inhibitor (IαI) is present in the AM extracts even after low (LS) or high speed (HS) centrifugation.

Inter-α-Trypsin Inhibitor (IαI) is Present in Different AM Extracts and its Heavy Chains (HCs) are Covalently Linked with HA FIG. 12 showed that before digestion with hyaluronidase, free heavy chains were present in different complexes, and a small amount of light chain was also present (UTI or bikunin). However, in all extracts, i.e., total and Extracts A, B, and C, there was also a covalently linked complex between HA and heavy chains of IαI as the latter was released only after hyaluronidase digestion. The same result was obtained in Extracts H and L obtained by two different speeds of centrifugation (FIG. 13).

Thrombospondin (TSP-1) is Present in Different AM Extracts

Figure 19:
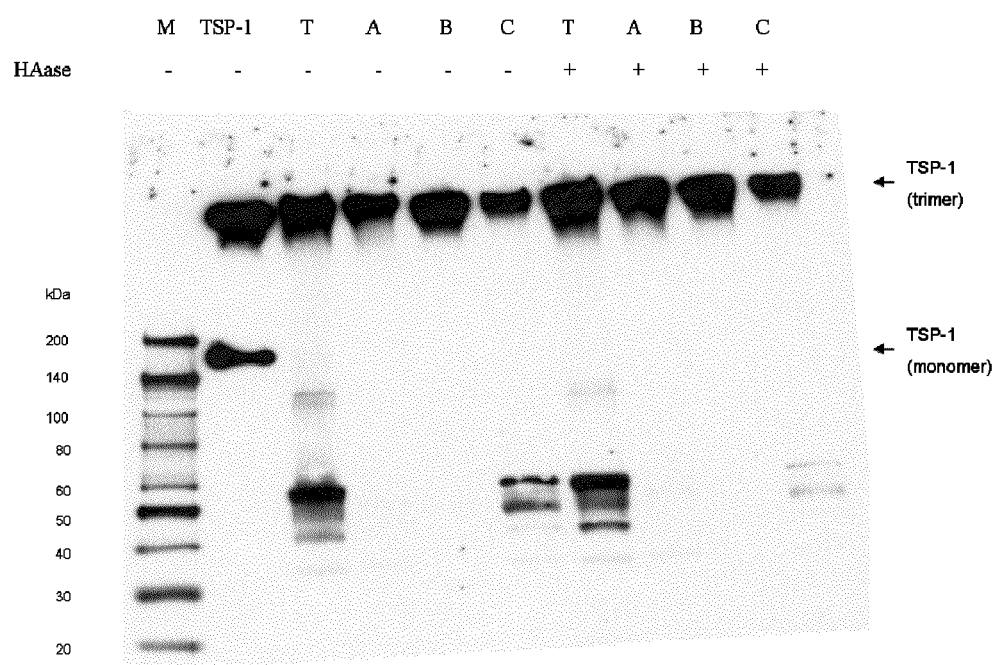
FIG. 19 is a non-limiting example of an immunoblot demonstrating the presence of TSP-1 in AM. The monomeric TSP-1 (180 kDa) and the putative trimeric TSP-1 (540 kDa) are indicated. The positive control, TSP-1, was purified from human platelets (Calbiochem, Cat#605225) and loaded as 100 ng/lane.

FIG. 19 showed that all AM extracts had a high molecular weight band of TSP-1 while the total extract (T) and Extract C also had some bands between 35-120 kDa. Hyaluronidase digestion did not change the reactive pattern except some bands became a little stronger or weaker.

Smad7 is Present in Mostly in Water-Insoluble AM Extracts

Figure 20:
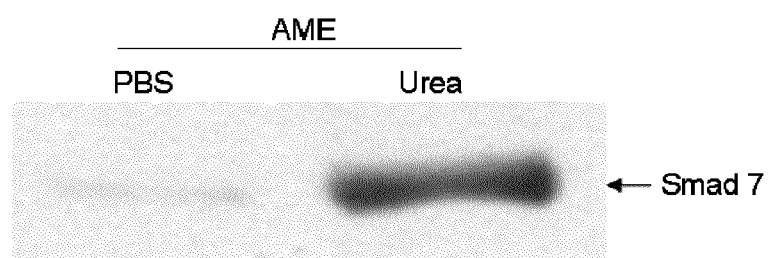
FIG. 20 is a non-limiting example of an immunoblot demonstrating the presence of Smad 7 in AM. AM was extracted with PBS or urea (2M urea in 50 mM Tris-HCl, pH 7.5). 20 µg of total protein was loaded for each extract. Smad 7 was detected with goat anti-human Smad 7 (AF2029, 1:1000, R & D Systems). Smad 7 migrated as a band of ~51 kDa.

Smad 7 was found in both PBS extracts and urea extracts of AM (FIG. 20).

Example 3

Water-Soluble AM Extracts Prevent Cell Death of Corneal Epithelial Cells (Basal Cells and Keratocytes) Induced by Storage and by Injuries Caused by Mechanical and Enzymatic Means Results To demonstrate that AM extracts can prevent apoptosis in injured tissues, the following experiment was performed using a murine model. A total of 22 mouse eye balls were enucleated, two of which were immediately embedded in OCT for frozen sections as a pretreatment control. The remaining of 20 eye balls were subdivided into three subgroups, namely, 1) mechanical scraping (n=8), 2) dispase digestion (enzymatic) (n=6), and 3) without treatment control (n=6). For each group, equal numbers of eye balls were preincubated at 4° C. for 24 h in the presence (+) or absence (−) of 125 μg/ml AM extracts in keratinocyte serum-free medium (KSFM) with defined supplement (Gibco, Carlsbad, Calif.) prior to the treatments. At the end of the first 24 h of incubation in KSFM+/−AM extract (prepared as described herein), 8 eyeballs in Subgroup 1 were then subjected to mechanical scraping with a surgical blade, and were further divided into two groups (n=4 each) and incubated at 37° C. in KSFM+/−AM extract. Six eye balls in Subgroup 2 were subjected to enzymatic digestion with 10 mg/ml Dispase II in KSFM+/−AM extract (n=3 each) for 18 h at 4° C. One eye ball from each group was embedded in OCT for frozen sections. The remaining two eye balls from each group were incubated in KSFM+/−AM extract for another 24 h before analysis. For the non-treatment control (n=6), 3 eye balls each were incubated in KSFM+/−AM extract at 37° C. continuously for two days; one eye ball was removed at the end of the first day while two eye balls were removed at the end of 2 days.

The frozen sections from these eyeballs were subjected to TUNEL staining. In short, terminal deoxyribonucleotidyl transferase-mediated FITC-linked dUTP nick-end DNA labeling (TUNEL) assay was performed using DeadEnd™ fluorometric TUNEL system obtained from Promega (Madison, Wis.) according to the manufacturer's instructions. Sections were fixed in 4% formaldehyde for 20 min at room temperature and permeabilized with 1% Triton X-100. Samples were then incubated for 60 min at 37° C. with exogenous TdT and fluorescein-conjugated dUTP for repair of nicked 3'-hydroxyl DNA ends. Cells were treated with DNase I as the positive control, while the negative control was incubated with buffer lacking rTdT enzyme. The apoptotic nuclei were labeled with green fluorescence, and the nuclei were counterstained with DAPI as red fluorescence.

The water-soluble form of AM extract was prepared by the method for preparing water-soluble AM extract. A BCA assay (Pierce, Rockford, Ill.) was used to quantitate the total protein in the AM extract.

The normal mouse eye ball showed a minimal amount of apoptosis only in the superficial layer of the corneal epithelium of the uninjured control before incubation in KSFM; no apoptosis was noted in the stromal keratocytes. However, after 24 h incubation at 4° C. in KSFM, there was a mild increase of apoptosis in keratocytes of the superficial stroma. Such an increase of keratocyte apoptosis was suppressed by AM extract.

The AM extract was also shown to reduce apoptosis after mechanical damage to the cells. After mechanical scraping, the mouse eye ball showed a significant increase of keratocyte apoptosis. However, incubation with AM extract following mechanical scraping resulted in a decrease in keratocyte apoptosis.

The mouse eyes were also treated enzymatically to damage the cells. Dispase digestion at 4° C. for 18 h in KSFM resulted in a significant amount of apoptosis in not only keratocytes but also in epithelial cells; for the latter apoptosis was found to be present not only in the superficial epithelial cells, but also in the basal epithelial cells. The extent of epithelial and keratocyte apoptosis was far greater than that noted after mechanical scraping. Incubation of AM extract during dispase digestion significantly reduced apoptosis of both epithelial cells and keratocytes. This is significant because dispase treatment mimics the surgical (e.g., excimer ablation in PRK) and pathological insults (e.g., recurrent corneal erosion) that can be directed to the basement membrane. The results of this experiment demonstrate that the application of AM extract to tissues with damaged cells can be used to reduce or prevent cellular damage.

Example 4

Comparing the Relative Potency of Using Collagen or HA as a Vehicle to Deliver Two Different AM Extracts To determine the optimal concentration of the water-soluble and lyophilized forms of AM extracts (prepared by the methods described herein for preparing water-soluble and lyophilized forms of AM extracts, respectively) and compare the relative potency between the two different vehicles containing an appropriate concentration of each form of AM extracts in suppressing TGF-β promoter activity and in promoting macrophage apoptosis, respectively, these two forms of AM extracts are compared by serial dilution in either type I collagen gel or HA and their protein concentrations are monitored accordingly. For type I collagen gel, the protein concentration varies from 0.05 to 2 mg/ml; for HA gel, the concentration varies from 0.05 to 10 mg/ml. These serially diluted solutions or gels of these two forms of AM extracts are pre-coated on plastic dishes before human corneal fibroblasts are seeded or added directly in DMEM with 10% FBS while cells are seeded on the plastic. The anti-scarring effect is measured by assaying the promoter activity of TGF-β1, β2, β3 and RII and comparing the promoter activity to the positive or negative controls where cells are seeded on plastic with or without a given form of AM extracts (without the vehicle), respectively. The positive control, in which cells were seeded on plastic with DMEM plus 10% FBS, showed a high promoter activity. In contrast, the negative control, in which cells were seeded on plastic with DMEM plus 10% FBS but added with 25 μg/ml AM extracts, showed at least 50% reduction of the promoter activity. Based on these control values, the experimental groups using different concentrations of AM extracts mixed in either collagen gel or HA can be measured.

Once the most effective concentration of these two forms of AM extracts in either collagen or HA is determined, the results are verified by repeating the experiment in serum-free DMEM with ITS added with 10 pg/ml to 5 ng/ml TGF-β1. The anti-scarring effect is further correlated with suppression of Smad-mediated signaling by immunocytolocalization of Smads 2, 3 and 4 and α-smooth muscle actin (α-SMA), a marker for myofibroblasts (Gabbiani G., J. Pathol. 200:500-503, 2003; Jester and Petroll, Prog Retin Eye Res. 18:311-356, 1999). Another positive control is performed by adding 10 μg/ml neutralizing antibody to all three isoforms of TGF-β. The anti-inflammatory effect is similarly tested in murine macrophages with or without activation by 200 U/ml IFN-γ in DMEM with ITS by measuring the extent of apoptosis using Cell Death Detection ELISAPLUS kit (Roche, Mannheim, Germany), and correlating the data with those obtained by cell morphology, LIVE/DEAD assay (Molecular Probes, Carlsbad, Calif.), Hoechst-33342 nuclear staining, and TUNEL assay (Promega, Madison, Wis.) as recently reported (Li et al., Exp Eye Res. 2005, In Press).

Example 5

Amniotic Membrane Stromal Extract has Anti-Angiogenic Properties

Materials and Methods

Materials

HUVECs and endothelial cell growth medium were from PromoCell GmbH (Heidelberg, Germany). Cell proliferation kit I (MTT) was from Roche (Penzberg, Germany). BCA™ protein assay kit was from Pierce (Rockford, Ill.). Dulbecco's modified Eagle's medium (DMEM), Ham's/F12 medium, HEPES buffer, Hank's balanced salt solution (HBSS), phosphate-buffered saline (PBS), amphotericin B, gentamicin, fetal bovine serum (FBS), vascular endothelial growth factor (VEGF), epidermal growth factor (EGF), basic fibroblast growth factor (bFGF), 0.25% trypsin/0.53 mM EDTA, LIVE/DEAD assay reagent were purchased from Invitrogen (Carlsbad, Calif.). Propidium iodide, Hoechst-33342 dye, triton X-100, bovine serum albumin (BSA), insulin, hydrocortisone, formaldehyde, crystal violet, FITC conjugated anti-mouse, goat, and rat IgG were from Sigma (St. Louis, Mo.). Transwell inserts were from Corning Incorporated (Corning, N.Y.). Matrigel was from BD Biosciences (Bedford, Mass.).

Cell Culture

HUVECs were cultured in the endothelial cell growth medium supplemented by 2% fetal calf serum, 0.1 ng/mL EGF, 1 μg/mL hydrocortisone, and 1 ng/mL basic fibroblast growth factor (bFGF). Human corneoscleral tissues were obtained from the Florida Lions Eye Bank (Miami, Fla.), from which corneal fibroblasts (HCFs) were harvested and cultured in DMEM containing 10% FBS. Passage 2 cells were used for the experiments. SV40-immortalized rabbit corneal epithelial cells (RCEs), kindly provided by Dr. Peter Reinach (Department of Biological Science, College of Optometry, State University of New York, N.Y.), were grown in DMEM/F12 containing 10% FBS, 5 ng/mL insulin, and 5 ng/mL EGF.

Preparation of Water-Soluble AM Stromal Extracts

Using aseptic techniques, frozen human AM obtained from Bio-Tissue, Inc. (Miami, Fla.) was briefly washed 2-3 times with HBSS to remove the original storage medium. The AM stroma was scraped by spatula, frozen in the air phase of liquid nitrogen and grounded to fine particles by BioPulverizer (Biospec Products, Inc., Bartlesville, Okla.) followed by homogenization on ice with Tissue Tearor (Biospec Products, Inc., Dremel, Wis.) in PBS, pH 7.4, for 1 min. The homogenate was mixed by rotation for 1 h and centrifuged at 14,000×g for 30 min at 4° C. The supernatant in PBS was then collected, and stored in aliquots at −80° C. The protein concentration was determined by BCA assay. This water-soluble protein extract, designated as amniotic stromal extract (ASE), was used for experiments described herein.

Cell Proliferation Assay

Cells were seeded in 96-well plates (n=6) in the respective growth medium mentioned above at the density of 2,000 cells per well with increasing concentrations of ASE and cultured for 48 h. The cell growth was determined by the MTT (3-[4,5-dimethylthiazol-2-yl]-2,5-dephenyl tetrazolium bromide)-based cell proliferation assay according to a protocol recommended by the manufacturer.

Apoptosis Assay

LIVE/DEAD assay and Hoechst-33342 staining were used for detecting apoptotic cells. Briefly, after 48 h of culturing, each respective growth medium was removed from the culture, added with 200 μl of the combined LIVE/DEAD assay reagents, and incubated for 15 min at room temperature. Live cells are distinguished by green fluorescence staining of the cell cytoplasm, while dead cells are stained with red fluorescence in the nuclei. To characterize the nuclear morphology as a means to assess apoptosis, Hoechst-33342 dye was added to each respective growth medium at a final concentration of 10 μg/mL, and incubated at 37° C. for 15 min. Hoechst-33342 stains the nuclei of live cells and identifies apoptotic cells by the increased fluorescence and nuclear fragmentation or condensation.

Migration Assay

The inhibitory effect of ASE on VEGF-induced chemotaxis was tested on HUVECs using the transwell assay. HUVECs were grown in the complete growth medium for 36 h. After trypsinization, washing, and resuspension of cells in the incomplete growth medium supplemented with 0.5% FBS, 60,000 cells in 200 μL were seeded on the inside of the transwell inserts (8 mm in diameter), which is separated by a polycarbonate membrane of 8-μm pore size, with or without 200 μg/mL of ASE. The growth medium in the volume of 800 μL supplemented with 1% FBS and 10 ng/mL VEGF was added as a chemotactant directly in 24-well plate outside of the transwell insert. The growth medium supplemented with 0.5% FBS was added directly in 24-well plate as the negative control. After incubation at 37° C. with 5% $CO_2$ and 95% humidity for 4.5 h, non-migrated cells were aspirated, while the membrane was washed with PBS, fixed in 4% formaldehyde in PBS, stained with crystal violet, and observed under the microscope. Cells migrating to the other side of the membrane were counted.

Endothelial Tube Formation Assay

Matrigel was added in 320 μL to each well of a 24-well plate and allowed to polymerize at 37° C. for 30 min. HUVECs (50,000 cells/well) in the endothelial cell culture medium with 10% FBS were seeded on Matrigel in the presence of different concentrations of ASE. Control cells were incubated with BSA at the same concentration. Cells were incubated for 24 h at 37° C. and photographed under a microscope (Nikon, Japan). Ten random 40× fields were photographed for each well, and tubes were counted, averaged, and compared.

Statistical Analysis

All experiments described above were repeated three times, each in triplicate or more. Group means were compared using the appropriate version of Student's unpaired t-test. Test results were reported as two-tailed p values, where $p<0.05$ was considered statistically significant. Summary data are reported as means±S.D.

Results

ASE Preferentially Inhibited Proliferation of HUVEC Cells

Figure 23:
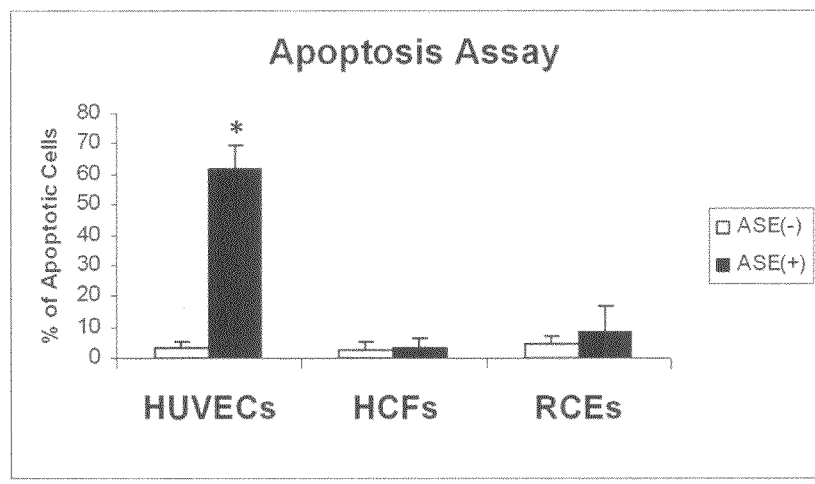
FIG. 23 is a non-limiting example of a bar graph demonstrating that the addition of ASE increases the number of apototic HUVEC cells.

We first tested whether ASE added to the culture medium would inhibit cellular proliferation. As compared to the control without addition of ASE, proliferation of HUVECs was significantly inhibited by 50 to 200 μg/mL of ASE (FIG. 21A, $p<0.001$). However, proliferation of RCEs and HCFs was significantly inhibited by ASE only at the concentration of 200 μg/mL (FIGS. 21B and 21C, respectively, each $p<0.01$). This result indicated that ASE preferentially inhibited proliferation of HUVECs ASE Induced Apoptosis in HUVEC Cells Phase contrast images showed that HUVEC cells shrank from a spindle shape to a small and round shape and the cell density was notably reduced when treated with 200 μg/mL of ASE for 48 h. In contrast, cell morphology and density of HCF and RCE cells were not changed when treated with 200 μg/mL of ASE for 48 h (Data not shown). To determine whether such a change in HUVEC cells caused by 200 μg/mL of ASE was accompanied by cell death, the LIVE/DEAD assay and Hoechst-33342 staining were performed after incubation with 200 μg/mL of ASE for 48 h. The results showed that HUVEC cells were alive in the control without addition of ASE (FIG. 22Aa) but showed pronounced cell death after ASE treatment (FIG. 22Ad). In contrast, both HCF and RCE cells did not reveal any notable cell death in cultures without (FIGS. 22Ab and 22Ac, respectively) or with (22Ae and 22Af, respectively) ASE treatment. Hoechst-33342 staining showed that ASE-treated HUVECs had 61.6±7.7% of condensed and fragmented nuclei (FIG. 22Bd), which was significantly higher than 3.1±1.8% of the control without ASE treatment (FIG. 22Ba, also see 2C, p<0.001). In contrast, there was no obvious apoptosis in either HCFs or RCEs without (FIGS. 22Bb and 22Bc, respectively) or with (FIGS. 22Be and 22Bf, respectively) ASE treatment (also see FIG. 23, p=0.84 and 0.30, respectively). These results indicated that ASE inhibited proliferation of HUVECs by inducing apoptosis.

ASE Inhibited Migration of HUVEC Cells with or without VEGF Stimulation

We then tested whether ASE could inhibit HUVEC migration stimulated by VEGF. Some cells migrated through pores of the polycarbonate membrane in the control without VEGF as a chemoattractant during the 4.5 h testing period (FIG. 24A). Cell migration increased dramatically when treated with VEGF as a chemoattractant (FIG. 24B, p<0.001). However, when HUVECs were treated with 200 μg/mL of ASE, the magnitude of cell migration under the influence of VEGF was significantly retarded (FIG. 24C) when compared to either the positive control with VEGF (p<0.001) or the negative control without VEGF (p<0.01). These results indicated that ASE not only abrogated the chemokine function of VEGF, but also inhibited migration intrinsically present in HUVECs.

ASE Inhibited Tube Formation of HUVEC Cells

To further investigate the anti-angiogenic action of ASE, we performed the in vitro tube formation assay. When HUVECs were seeded on Matrigel, a solid gel of basement membrane proteins, they rapidly aligned and formed hollow tube-like structures after 24 h (FIG. 25A). In contrast, when ASE was added to the culture, tube formation of HUVECs was significantly inhibited at the concentration of either 100 μg/mL (FIG. 25B) or 200 μg/mL (FIG. 25C) (both p<0.001). The difference between these two doses of ASE was not statistically significant (FIG. 25D). Collectively, these results indicated that ASE also exerted its anti-angiogenic action by inhibiting the tube formation during the angiogenic process.

Example 6

Skin Lotion Composition Containing AM Extract

A skin lotion is prepared by the following method. 0.25 g methyl hydroxybenzoate and 7.5 g glycerin are dissolved in 75 ml of water at 150° F. 0.7 g sorbitan monolaurate, 0.7 g polysorbate 20, and 1.0 g cetostearyl alcohol are melted at 150° F. and are then compounded into the solution. The mixture is allowed to cool while mixing. When the mixture reaches a temperature below approximately 90° F., 4 ml of AM preparations and purified compositions described herein is added while mixing. A trace amount of fragrance is also added while mixing. The lotion is packaged into 10 ml aliquots and stored at room temperature.

Example 7

Ophthalmic Solution Composition and Treatment of an Eye Disease

An opthalmic eye drop solution is prepared by mixing 100 mg of ground, lyophilized AM extract with 0.9 g of NaCl in 100 mL of purified water and filtered using a 0.2 micron filter. The resulting isotonic solution is then incorporated into ophthalmic delivery units, such as eye drop containers, which are suitable for ophthalmic administration. Two drops of the composition is applied to a burn-damaged eye 4 times per day. By use of this method, the eye returns to normal health.

Example 8

Eye Ointment Composition and Treatment of Eye Disease Using Same

A sterile eye ointment composition is prepared by compounding 90 grams white petrolatum, 10 grams liquid petrolatum, and 0.5 grams lyophilized AM powder. The mixture is pasteurized and packaged into individual tube containers of 2.0 g each.

To treat an eye disease using the composition, an aliquot of approximately 0.1 g is gently applied directly from the tube to the inner edge of the bottom eye lid. The ointment is applied 4 times per day. The patient progress is monitored every other week by an opthamologist. By use of this method, the eye disease improves.

Example 9

Treatment of Human Eye Disease Using AM Preparation

An individual with burn damage to the eye is identified. A preparation of 1% AM, 0.5% collagen in DMEM is prepared. The individual is treated 4× per day with 2 drops of the composition. By use of this method, the eye damage improves as compared to a non-treated burn damaged eye.

Example 10

Treatment of Human Skin Disease Using AM Preparation

An individual with psoriasis is identified. The individual is treated with a 5% preparation of reconstituted AM, supplemented with 1 mg/ml purified Smad7 derived from a commercial source. The formulation is dissolved in a lotion composition. The treatment is administered 2 times per day. By use of this method, the psoriasis is alleviated or disappears.

Example 11

Rectal Gel Composition Containing AM Extract

A rectal gel composition is prepared by combining 100 mg of commercially available HA and TSG-6 (purified) with 5 ml sterile AM extract prepared from frozen AM membrane material as described in Example 1. To this mixture is added 2.5 g of methylcelluose (1500 mPa), 100 mg of methylparapen, 5 g of glycerin and 95 mL of purified water. The resulting gel mixture is then incorporated into rectal delivery units, such as syringes, which are suitable for rectal administration.

What is claimed is:
1. A method of inhibiting angiogenesis in an individual in need thereof, comprising administering a ground or pulverized amniotic membrane derived from a frozen or previously frozen placental material.
2. The method of claim 1, wherein the ground or pulverized amniotic membrane is in the form of a homogenate.

3. The method of claim 1, wherein the ground or pulverized amniotic membrane is in the form of a dry powder, liquid or suspension.

4. The method of claim 1, wherein the placental material is placenta.

5. The method of claim 1, wherein the amniotic membrane is human amniotic membrane, bovine amniotic membrane, or porcine amniotic membrane.

6. A method of inhibiting angiogenesis in an individual in need thereof, comprising administering a pharmaceutical composition comprising a ground or pulverized amniotic membrane derived from a frozen or previously frozen placental material.

7. The method of claim 6, wherein the placental material is placenta.

8. The method of claim 6, wherein the composition further comprises a pharmaceutically-acceptable excipient.

9. The method of claim 6, wherein the composition is a non-solid dosage form.

10. The method of claim 9, wherein the composition is a solution, suspension, paste, ointment, oil, emulsion, cream, lotion, gel, patch, stick, balm, or shampoo.

11. The method of claim 6, wherein the composition is an ophthalmic composition.

12. The method of claim 6, wherein the composition is a topical composition.

\* \* \* \* \*